(12) United States Patent
Chang et al.

(10) Patent No.: US 12,319,752 B2
(45) Date of Patent: *Jun. 3, 2025

(54) HEPARIN-BINDING CATIONIC PEPTIDE SELF-ASSEMBLING PEPTIDE AMPHIPHILES USEFUL AGAINST DRUG-RESISTANT BACTERIA

(71) Applicant: Northeastern University, Boston, MA (US)

(72) Inventors: Run Chang, Brighton, MA (US); Keerthana Subramanian, Boston, MA (US); Mian Wang, Malden, MA (US); Thomas J. Webster, Barrington, RI (US)

(73) Assignee: Northeastern University, Boston, MA (US)

( * ) Notice: Subject to any disclaimer, the term of this patent is extended or adjusted under 35 U.S.C. 154(b) by 586 days.

This patent is subject to a terminal disclaimer.

(21) Appl. No.: 17/525,354

(22) Filed: Nov. 12, 2021

(65) Prior Publication Data
US 2022/0227810 A1 Jul. 21, 2022

Related U.S. Application Data

(63) Continuation of application No. 15/832,194, filed on Dec. 5, 2017, now Pat. No. 11,174,288.

(60) Provisional application No. 62/430,906, filed on Dec. 6, 2016.

(51) Int. Cl.
| C07K 7/08 | (2006.01) |
| A61P 31/04 | (2006.01) |
| C07H 5/06 | (2006.01) |
| C07H 5/10 | (2006.01) |

(52) U.S. Cl.
CPC ............... *C07K 7/08* (2013.01); *A61P 31/04* (2018.01); *C07H 5/06* (2013.01); *C07H 5/10* (2013.01)

(58) Field of Classification Search
CPC .................................. C07K 7/08; A61P 31/04
See application file for complete search history.

(56) References Cited

U.S. PATENT DOCUMENTS

| 3,948,882 A | 4/1976 | Umezawa et al. |
| 3,992,528 A | 11/1976 | Graham et al. |
| 4,102,877 A | 7/1978 | Nutt |
| 4,128,542 A | 12/1978 | Atherton et al. |
| 4,237,045 A | 12/1980 | Failli et al. |
| 4,250,085 A | 2/1981 | Atherton et al. |
| 4,351,828 A | 9/1982 | Failli et al. |
| 4,396,543 A | 8/1983 | Debono |
| 4,399,067 A | 8/1983 | Debono |
| RE32,310 E | 12/1986 | Debono |
| RE32,311 E | 12/1986 | Debono |
| 4,816,559 A | 3/1989 | Harada et al. |
| 4,994,270 A | 2/1991 | Boeck et al. |
| 5,028,590 A | 7/1991 | Fukuda et al. |
| 5,034,510 A | 7/1991 | Shiba et al. |
| 5,041,644 A | 8/1991 | Morita et al. |
| 5,045,531 A | 9/1991 | Berkowitz et al. |
| 5,080,936 A | 1/1992 | Cerwen |
| 5,208,220 A | 5/1993 | Berkowitz |
| 5,215,896 A | 6/1993 | Keck et al. |
| 5,217,956 A | 6/1993 | Zasloff et al. |
| 5,221,664 A | 6/1993 | Berkowitz et al. |
| 5,221,732 A | 6/1993 | Chen et al. |
| 5,225,529 A | 7/1993 | Butelman et al. |
| 5,254,535 A | 10/1993 | Zasloff et al. |
| 5,302,526 A | 4/1994 | Keck et al. |
| 5,304,631 A | 4/1994 | Stewart et al. |
| 5,330,902 A | 7/1994 | Keck et al. |
| 5,336,757 A | 8/1994 | Gulavita et al. |
| 5,338,682 A | 8/1994 | Sasaki et al. |
| 5,408,036 A | 4/1995 | Ghadiri |
| 5,446,023 A | 8/1995 | Pavia et al. |
| 5,458,874 A | 10/1995 | Pereira et al. |
| 5,459,237 A | 10/1995 | Berkowitz et al. |
| 5,464,819 A | 11/1995 | Suzuki |
| 5,470,950 A | 11/1995 | Maloy et al. |
| 5,482,723 A | 1/1996 | Sasaki et al. |
| 5,484,885 A | 1/1996 | Pereira et al. |
| 5,503,776 A | 4/1996 | Murase et al. |
| 5,508,182 A | 4/1996 | Schneider et al. |
| 5,516,755 A | 5/1996 | Gulavita et al. |
| 5,550,109 A | 8/1996 | Schonwetter et al. |
| 5,589,364 A | 12/1996 | Williams et al. |
| RE35,492 E | 4/1997 | Berkowitz et al. |
| 5,635,479 A | 6/1997 | Jacob et al. |
| 5,637,564 A | 6/1997 | Pavia et al. |
| 5,646,014 A | 7/1997 | Hara |
| 5,650,393 A | 7/1997 | Pavia et al. |
| 5,654,273 A | 8/1997 | Gallo et al. |
| 5,654,274 A | 8/1997 | Kari |
| 5,656,738 A | 8/1997 | Schonwetter et al. |
| 5,670,483 A | 9/1997 | Zhang et al. |

(Continued)

OTHER PUBLICATIONS

Bahar and Ren, Pharmaceuticals 2013, 6, 1543-1575 (Year: 2013).*
International Journal for Parasitology: Parasites and Wildlife 4 (2015) 80-87, Serge Morand (Year: 2015).*
R. Poulin et al.,Journal of Sea Research 113 (2016) 3-10 (Year: 2016).*
Shimazaki, 1998 J Dairy Sci 81:2841-2849 (Year: 1998).*
Sweet and Bateman, Jl. Sea Rsch, 113 (2016) 28-44 (Year: 2016).*
Meng, Langmuir 2012, 28, 5017-5022 (Year: 2012).*

(Continued)

*Primary Examiner* — Melissa L Fisher
*Assistant Examiner* — Joseph Fischer
(74) *Attorney, Agent, or Firm* — Foley Hoag LLP; Dana M. Gordon; Lawrence P. Tardibono

(57) ABSTRACT

Disclosed are peptides comprising an amphiphilic backbone and a cationic heparin-binding motif peptide. The peptides can be used in methods of antimicrobial treatment.

13 Claims, 33 Drawing Sheets

Specification includes a Sequence Listing.

(56) References Cited

U.S. PATENT DOCUMENTS

| | | |
|---|---|---|
| 5,686,563 A | 11/1997 | Kari |
| 5,707,855 A | 1/1998 | Hancock et al. |
| 5,783,689 A | 7/1998 | Miller et al. |
| 5,849,490 A | 12/1998 | Schonwetter et al. |
| 5,858,971 A | 1/1999 | Fujiwara et al. |
| 5,861,376 A | 1/1999 | Henderson et al. |
| 5,863,897 A | 1/1999 | Gallo et al. |
| 5,912,226 A | 6/1999 | Baker et al. |
| 5,936,063 A | 8/1999 | Kim et al. |
| 5,955,343 A | 9/1999 | Holmes et al. |
| 6,111,067 A | 8/2000 | Debono et al. |
| 6,127,336 A | 10/2000 | Bulet et al. |
| 6,331,522 B1 | 12/2001 | Bulet et al. |
| 6,348,445 B1 | 2/2002 | Kari et al. |
| 6,476,189 B1 | 11/2002 | Yamakawa et al. |
| 6,548,048 B1 | 4/2003 | Cuthbertson et al. |
| 6,548,630 B1 | 4/2003 | Zhang et al. |
| 6,630,171 B1 | 10/2003 | Huille et al. |
| 6,632,922 B1 | 10/2003 | Deming et al. |
| 6,677,431 B2 | 1/2004 | DeGrado et al. |
| 6,686,446 B2 | 2/2004 | Deming et al. |
| 6,734,165 B2 | 5/2004 | Chiosis et al. |
| 6,800,481 B1 | 10/2004 | Holmes et al. |
| 6,849,660 B1 | 2/2005 | Jefferson et al. |
| 6,875,611 B2 | 4/2005 | Mahato et al. |
| 7,001,983 B1 | 2/2006 | Shai et al. |
| RE39,071 E | 4/2006 | Baker et al. |
| 7,084,248 B2 | 8/2006 | Summerton |
| 7,098,028 B2 | 8/2006 | Holmes et al. |
| 7,255,855 B2 | 8/2007 | Sung et al. |
| 7,319,088 B2 | 1/2008 | Lazzarini et al. |
| 7,320,890 B2 | 1/2008 | Mahato et al. |
| 7,329,727 B2 | 2/2008 | Deming |
| 7,351,687 B2 | 4/2008 | Lazzarini et al. |
| 7,439,228 B2 | 10/2008 | Svendsen et al. |
| 7,452,679 B2 | 11/2008 | Stupp et al. |
| 7,452,856 B2 | 11/2008 | Nagaoka et al. |
| 7,491,690 B2 | 2/2009 | Stupp et al. |
| 7,544,661 B2 | 6/2009 | Stupp et al. |
| 7,554,021 B2 | 6/2009 | Stupp et al. |
| 7,563,764 B2 | 7/2009 | Lu |
| 7,589,216 B2 | 9/2009 | Kapa et al. |
| 7,671,011 B2 | 3/2010 | Shai et al. |
| 7,723,468 B2 | 5/2010 | Daffre et al. |
| 7,790,694 B2 | 9/2010 | Geller et al. |
| 7,807,176 B2 | 10/2010 | Nishikawa et al. |
| 7,838,491 B2 | 11/2010 | Stupp et al. |
| 7,968,519 B2 | 6/2011 | Deming et al. |
| 8,080,262 B2 | 12/2011 | Lee et al. |
| 8,080,402 B2 | 12/2011 | Sung et al. |
| 8,084,399 B2 | 12/2011 | Yu et al. |
| 8,124,583 B2 | 2/2012 | Stupp et al. |
| 8,138,140 B2 | 3/2012 | Stupp et al. |
| 8,143,211 B2 | 3/2012 | Svendsen et al. |
| 8,206,735 B2 | 6/2012 | Li et al. |
| 8,242,082 B2 | 8/2012 | Nagaoka et al. |
| 8,268,961 B2 | 9/2012 | Bracci et al. |
| 8,394,760 B2 | 3/2013 | Yang et al. |
| 8,410,046 B2 | 4/2013 | Hahm et al. |
| 8,431,528 B2 | 4/2013 | Lu et al. |
| 8,440,794 B2 | 5/2013 | Bracci et al. |
| 8,445,636 B2 | 5/2013 | Shai et al. |
| 8,580,923 B2 | 11/2013 | Stupp et al. |
| 8,637,267 B2 | 1/2014 | Keiler et al. |
| 8,658,763 B2 | 2/2014 | Rapaport |
| 8,758,833 B2 | 6/2014 | Garnier et al. |
| 8,809,036 B2 | 8/2014 | Qiao et al. |
| 8,840,915 B2 | 9/2014 | Li et al. |
| 8,877,203 B2 | 11/2014 | Bae et al. |
| 8,877,738 B2 | 11/2014 | Giuliani et al. |
| 8,883,718 B2 | 11/2014 | Warenius et al. |
| 8,889,430 B2 | 11/2014 | Yang et al. |
| 8,921,308 B2 | 12/2014 | Pini et al. |
| 8,921,309 B2 | 12/2014 | Boyce et al. |
| 8,980,844 B2 | 3/2015 | Chung et al. |
| 9,012,404 B2 | 4/2015 | Spirio et al. |
| 9,024,005 B2 | 5/2015 | McArthur |
| 9,067,084 B2 | 6/2015 | Hauser et al. |
| 9,073,967 B2 | 7/2015 | Cheng et al. |
| 9,120,841 B2 | 9/2015 | Hauser et al. |
| 9,133,246 B2 | 9/2015 | Chung et al. |
| 9,180,203 B2 | 11/2015 | Cui et al. |
| 9,233,084 B2 | 1/2016 | Rana et al. |
| 9,371,363 B2 | 6/2016 | O'Neil |
| 9,457,056 B2 | 10/2016 | Rapaport |
| 9,463,214 B2 | 10/2016 | Park et al. |
| 9,475,843 B2 | 10/2016 | Wang et al. |
| 9,511,112 B2 | 12/2016 | de Paoli Ambrosi |
| 9,562,257 B2 | 2/2017 | Keiler et al. |
| 9,669,101 B2 | 6/2017 | McArthur |
| 9,670,249 B2 | 6/2017 | Rapaport |
| 9,682,140 B2 | 6/2017 | Holms et al. |
| 9,695,231 B2 | 7/2017 | Wang et al. |
| 9,725,734 B2 | 8/2017 | Stover et al. |
| 9,732,120 B2 | 8/2017 | Lim et al. |
| 9,737,584 B2 | 8/2017 | Isanaka |
| 9,745,348 B2 | 8/2017 | Lu et al. |
| 9,754,040 B2 | 9/2017 | Saha et al. |
| 9,757,472 B2 | 9/2017 | Diehnelt et al. |
| 9,862,749 B2 | 1/2018 | Park |
| 9,974,861 B2 | 5/2018 | Johnsson et al. |
| 9,987,370 B2 | 6/2018 | Cui et al. |
| 9,994,615 B2 | 6/2018 | Langer et al. |
| 10,004,689 B2 | 6/2018 | Freund et al. |
| 10,071,183 B2 | 9/2018 | Hauser et al. |
| 10,086,108 B2 | 10/2018 | Schneider et al. |
| 10,138,282 B2 | 11/2018 | Kao et al. |
| 10,150,795 B2 | 12/2018 | Kim et al. |
| 10,265,408 B2 | 4/2019 | Chmielewski et al. |
| 10,285,938 B2 | 5/2019 | Isanaka et al. |
| 10,301,354 B2 | 5/2019 | Park |
| 10,316,079 B2 | 6/2019 | Wang et al. |
| 10,350,299 B2 | 7/2019 | McArthur |
| 10,428,137 B2 | 10/2019 | Schiller et al. |
| 10,456,227 B2 | 10/2019 | Hussain et al. |
| 10,517,920 B2 | 12/2019 | Hussein |
| 10,532,105 B2 | 1/2020 | Homan et al. |
| 10,570,262 B2 | 2/2020 | Wu et al. |
| 10,576,123 B2 | 3/2020 | Takamura et al. |
| 10,596,225 B2 | 3/2020 | Takamura et al. |
| 10,597,735 B2 | 3/2020 | Keiler et al. |
| 10,632,172 B2 | 4/2020 | Kumar et al. |
| 11,174,288 B2 | 11/2021 | Chang et al. |
| 2001/0038824 A1 | 11/2001 | Horii et al. |
| 2001/0048940 A1 | 12/2001 | Tousignant et al. |
| 2001/0049117 A1 | 12/2001 | Axelrod et al. |
| 2002/0032309 A1 | 3/2002 | Deming et al. |
| 2002/0058020 A1 | 5/2002 | Rozenberg et al. |
| 2002/0132766 A1 | 9/2002 | DeGrado et al. |
| 2003/0026840 A1 | 2/2003 | Plank et al. |
| 2003/0125372 A1 | 7/2003 | Chiosis et al. |
| 2003/0143266 A1 | 7/2003 | Tousignant et al. |
| 2003/0148936 A1 | 8/2003 | Svendsen et al. |
| 2003/0175755 A1 | 9/2003 | Abiko et al. |
| 2003/0186854 A1 | 10/2003 | Daffre et al. |
| 2004/0018961 A1 | 1/2004 | Stupp et al. |
| 2004/0022799 A1 | 2/2004 | Rozenberg et al. |
| 2004/0028702 A1 | 2/2004 | Maletic et al. |
| 2004/0034888 A1 | 2/2004 | Liu et al. |
| 2004/0063123 A1 | 4/2004 | Abiko et al. |
| 2004/0087013 A1 | 5/2004 | Holmes et al. |
| 2004/0132958 A1 | 7/2004 | Deming et al. |
| 2004/0180814 A1 | 9/2004 | Chiosis et al. |
| 2004/0242488 A1 | 12/2004 | Ribeiro De Paiva et al. |
| 2005/0032722 A1 | 2/2005 | Mahato et al. |
| 2005/0191720 A1 | 9/2005 | Sung et al. |
| 2005/0203005 A1 | 9/2005 | Lazzarini et al. |
| 2005/0208589 A1 | 9/2005 | Stupp et al. |
| 2005/0209145 A1 | 9/2005 | Stupp et al. |
| 2005/0233952 A1 | 10/2005 | Lazzarini et al. |
| 2005/0261504 A1 | 11/2005 | Kapa et al. |
| 2005/0287671 A1 | 12/2005 | Mahato et al. |
| 2006/0009374 A1 | 1/2006 | Nagaoka et al. |
| 2006/0014667 A1 | 1/2006 | Summerton |

(56) References Cited

U.S. PATENT DOCUMENTS

| | | |
|---|---|---|
| 2006/0084607 A1 | 4/2006 | Spirio et al. |
| 2006/0149036 A1 | 7/2006 | Stupp et al. |
| 2006/0166883 A1 | 7/2006 | Lu |
| 2006/0183673 A1 | 8/2006 | Lazzarini et al. |
| 2006/0241031 A1 | 10/2006 | Akesson et al. |
| 2006/0258596 A1 | 11/2006 | Walsh et al. |
| 2006/0276380 A1 | 12/2006 | Daffre et al. |
| 2007/0060753 A1 | 3/2007 | Slade et al. |
| 2007/0072808 A1 | 3/2007 | Shai et al. |
| 2007/0123699 A1 | 5/2007 | Heckl et al. |
| 2007/0135333 A1 | 6/2007 | Geller et al. |
| 2007/0190603 A1 | 8/2007 | Holmes et al. |
| 2007/0203062 A1 | 8/2007 | Ellis-Behnke et al. |
| 2007/0253935 A1 | 11/2007 | Sung et al. |
| 2007/0281888 A1 | 12/2007 | Nishikawa et al. |
| 2008/0020016 A1 | 1/2008 | Li et al. |
| 2008/0026070 A1 | 1/2008 | Bonnet-Gonnet |
| 2008/0032924 A1 | 2/2008 | East et al. |
| 2008/0102128 A1 | 5/2008 | Constancis et al. |
| 2008/0125581 A1 | 5/2008 | Deming et al. |
| 2008/0145432 A1 | 6/2008 | Kakizawa et al. |
| 2008/0234333 A1 | 9/2008 | Kang et al. |
| 2008/0242597 A1 | 10/2008 | Liu et al. |
| 2008/0287346 A1 | 11/2008 | Svendsen et al. |
| 2008/0312134 A1 | 12/2008 | Hirt et al. |
| 2009/0028839 A1 | 1/2009 | Tchikindas et al. |
| 2009/0053151 A1 | 2/2009 | Bracci et al. |
| 2009/0074864 A1* | 3/2009 | Schmidtchen ..... C07K 14/8128 424/45 |
| 2009/0087493 A1 | 4/2009 | Dai et al. |
| 2009/0118515 A1 | 5/2009 | Slade et al. |
| 2009/0123365 A1 | 5/2009 | Yang et al. |
| 2009/0143241 A1 | 6/2009 | Keiler et al. |
| 2009/0149632 A1 | 6/2009 | Nagaoka et al. |
| 2009/0156505 A1 | 6/2009 | Stupp et al. |
| 2009/0186811 A1 | 7/2009 | Schwartz |
| 2009/0196831 A1 | 8/2009 | Yang et al. |
| 2009/0239939 A1 | 9/2009 | Plank et al. |
| 2009/0269847 A1 | 10/2009 | Stupp et al. |
| 2010/0015197 A1 | 1/2010 | Rapaport |
| 2010/0047186 A1 | 2/2010 | O'Neil |
| 2010/0143504 A1 | 6/2010 | Spirio et al. |
| 2010/0160213 A1 | 6/2010 | Shai et al. |
| 2010/0168421 A1 | 7/2010 | Kang et al. |
| 2010/0172961 A1 | 7/2010 | Lee et al. |
| 2010/0173796 A1 | 7/2010 | Yu et al. |
| 2010/0184683 A1 | 7/2010 | Eckert et al. |
| 2010/0221224 A1 | 9/2010 | Stupp et al. |
| 2010/0234280 A1 | 9/2010 | Geller et al. |
| 2010/0249018 A1 | 9/2010 | Bae et al. |
| 2010/0297096 A1 | 11/2010 | Rapaport |
| 2010/0311821 A1 | 12/2010 | Geng |
| 2011/0002880 A1 | 1/2011 | Takamura et al. |
| 2011/0046747 A1 | 2/2011 | Yeung et al. |
| 2011/0053834 A1 | 3/2011 | Hahm et al. |
| 2011/0105385 A1 | 5/2011 | Lu et al. |
| 2011/0150837 A1 | 6/2011 | Chan et al. |
| 2011/0158956 A1 | 6/2011 | Warenius et al. |
| 2011/0190198 A1 | 8/2011 | Bracci et al. |
| 2011/0201541 A1 | 8/2011 | Takamura et al. |
| 2011/0223111 A1 | 9/2011 | Rana et al. |
| 2011/0224129 A1 | 9/2011 | Boyce et al. |
| 2011/0230367 A1 | 9/2011 | Yu et al. |
| 2011/0288008 A1 | 11/2011 | Keiler et al. |
| 2011/0300071 A1 | 12/2011 | Woodard et al. |
| 2011/0300094 A1 | 12/2011 | Dimitrova |
| 2012/0009625 A1 | 1/2012 | Qiao et al. |
| 2012/0058936 A1 | 3/2012 | Andremont et al. |
| 2012/0088848 A1 | 4/2012 | Deming et al. |
| 2012/0121623 A1 | 5/2012 | Giuliani et al. |
| 2012/0121725 A1 | 5/2012 | Garnier et al. |
| 2012/0122769 A1 | 5/2012 | Iversen |
| 2012/0237476 A1 | 9/2012 | Li et al. |
| 2012/0264912 A1 | 10/2012 | Stupp et al. |
| 2013/0023460 A1 | 1/2013 | Hauser et al. |
| 2013/0059775 A1 | 3/2013 | McArthur |
| 2013/0109834 A1 | 5/2013 | Cheng et al. |
| 2013/0130969 A1 | 5/2013 | Pini et al. |
| 2013/0203654 A1 | 8/2013 | Sekimizu et al. |
| 2013/0210707 A1 | 8/2013 | Chung et al. |
| 2013/0281547 A1 | 10/2013 | Spirio et al. |
| 2013/0296239 A1 | 11/2013 | Takamura et al. |
| 2014/0038909 A1 | 2/2014 | Takamura et al. |
| 2014/0093473 A1 | 4/2014 | Hauser et al. |
| 2014/0105993 A1 | 4/2014 | Constancis et al. |
| 2014/0113875 A1 | 4/2014 | Cui et al. |
| 2014/0187443 A1 | 7/2014 | Keiler et al. |
| 2014/0187743 A1 | 7/2014 | Chung et al. |
| 2014/0219981 A1 | 8/2014 | Rapaport |
| 2014/0286904 A1 | 9/2014 | Ross et al. |
| 2014/0294982 A1 | 10/2014 | Freund et al. |
| 2014/0309162 A1 | 10/2014 | Park |
| 2014/0329914 A1 | 11/2014 | Kobayashi et al. |
| 2015/0025005 A1 | 1/2015 | Langer et al. |
| 2015/0057217 A1 | 2/2015 | Lu et al. |
| 2015/0126452 A1 | 5/2015 | Schiller et al. |
| 2015/0196652 A1 | 7/2015 | McArthur |
| 2015/0225454 A1 | 8/2015 | Beuerman et al. |
| 2015/0231199 A1* | 8/2015 | Chandra Shekhar ... A61P 31/10 514/2.7 |
| 2015/0258166 A1 | 9/2015 | Spirio et al. |
| 2015/0297673 A1 | 10/2015 | Park et al. |
| 2015/0344547 A1 | 12/2015 | Wang et al. |
| 2015/0367028 A1 | 12/2015 | Hauser et al. |
| 2016/0022832 A1 | 1/2016 | Diehnelt et al. |
| 2016/0030629 A1 | 2/2016 | Sun et al. |
| 2016/0084829 A1 | 3/2016 | Lim et al. |
| 2016/0168224 A1 | 6/2016 | Braga et al. |
| 2016/0184404 A1 | 6/2016 | Heini et al. |
| 2016/0220691 A1 | 8/2016 | Cui et al. |
| 2016/0257718 A1 | 9/2016 | Wang et al. |
| 2016/0271178 A1 | 9/2016 | Hauser et al. |
| 2016/0287744 A1 | 10/2016 | Kobayashi et al. |
| 2016/0312241 A1 | 10/2016 | Stover et al. |
| 2016/0317607 A1 | 11/2016 | Spirio et al. |
| 2016/0326218 A1 | 11/2016 | Park |
| 2016/0346383 A1 | 12/2016 | Holms et al. |
| 2016/0367651 A1 | 12/2016 | Shiku et al. |
| 2017/0014473 A1 | 1/2017 | Rapaport |
| 2017/0042959 A1 | 2/2017 | Isanaka |
| 2017/0081378 A1 | 3/2017 | Kao et al. |
| 2017/0096717 A1 | 4/2017 | Keiler et al. |
| 2017/0189334 A1 | 7/2017 | Sun et al. |
| 2017/0202783 A1 | 7/2017 | Chang et al. |
| 2017/0204138 A1 | 7/2017 | Cooper et al. |
| 2017/0240926 A1 | 8/2017 | McQualter |
| 2017/0246240 A1 | 8/2017 | Hussein |
| 2017/0253638 A1 | 9/2017 | Ross et al. |
| 2017/0258735 A1 | 9/2017 | Rapaport et al. |
| 2017/0260259 A1 | 9/2017 | Wang et al. |
| 2017/0290770 A1 | 10/2017 | Isanaka et al. |
| 2017/0340745 A1 | 11/2017 | McArthur |
| 2018/0000983 A1 | 1/2018 | Schneider et al. |
| 2018/0125620 A1 | 5/2018 | Hussain et al. |
| 2018/0170965 A1 | 6/2018 | Kim et al. |
| 2018/0179251 A1 | 6/2018 | Park |
| 2018/0179255 A1 | 6/2018 | Chang et al. |
| 2018/0325821 A1 | 11/2018 | Freund et al. |
| 2018/0327643 A1 | 11/2018 | Lee et al. |
| 2018/0346524 A1 | 12/2018 | Diep et al. |
| 2018/0346526 A1 | 12/2018 | Benjdia et al. |
| 2018/0353428 A1 | 12/2018 | Sun et al. |
| 2019/0038759 A1 | 2/2019 | Chmielewski et al. |
| 2019/0076544 A1 | 3/2019 | Homan et al. |
| 2019/0083654 A1 | 3/2019 | Guan et al. |
| 2019/0175741 A1 | 6/2019 | Chmielewski et al. |
| 2019/0247459 A1 | 8/2019 | Qiao et al. |
| 2019/0248956 A1 | 8/2019 | Chen et al. |
| 2019/0248971 A1 | 8/2019 | Wu et al. |
| 2019/0298841 A1 | 10/2019 | McArthur |
| 2019/0315806 A1 | 10/2019 | Cui et al. |
| 2019/0328903 A1 | 10/2019 | Choi et al. |
| 2019/0374599 A1 | 12/2019 | Chung et al. |
| 2019/0382746 A1 | 12/2019 | Green |

(56) References Cited

U.S. PATENT DOCUMENTS

| | | |
|---|---|---|
| 2019/0388494 A1 | 12/2019 | Falciani et al. |
| 2020/0000875 A1 | 1/2020 | Kumar et al. |
| 2020/0040035 A1 | 2/2020 | Kim et al. |
| 2020/0046800 A1 | 2/2020 | Afonina et al. |
| 2020/0071358 A1 | 3/2020 | Afonina et al. |
| 2020/0123328 A1 | 4/2020 | Qiao et al. |

OTHER PUBLICATIONS

Andersson et al., "Antimicrobial activities of heparin-binding peptides," Eur J Biochem 271:1219-1226 (2004).
Bahar et al., "Antimicrobial Peptides," Pharmaceuticals, 6: 1543-1575 (2013).
Brogden, "Antimicrobial Peptides: Pore Formers or Metabolic Inhibitors in Bacteria?," Nat Rev Micro., 3:238-250 (2005).
Cardin et al., "Molecular Modeling of Protein-Glycosaminoglycan Interactions," Arterioscler Thromb Vasc Biol., 9(1):21-32 (1989).
Chang et al., "Enhanced Antibacterial Properties of Self-Assembling Peptide Amphiphiles Functionalized with Heparin-Binding Cardin-Motifs," Applied Materials and Interfaces, 9:22350-22360 (2017).
Chen et al., "Antibacterial Activities of Short Designer Peptides: A Link between Propensity for Nanostructuring and Capacity for Membrane Destabilization," Biomacromolecules, 11(2):402-411 (2010).
Chen et al., "pH-Controlled Hierarchical Self-Assembly of Peptide Amphiphile," Macromolecules, 48(8):2647-2653 (2015).
Chu-Kung et al., "Chain Length Dependence of Antimicrobial Peptide-Fatty Acid Conjugate Activity," J. Colloid Interface Sci., 345(2):160-167 (2010).
Cui et al., "Invited Review Self-Assembly of Peptide Amphiphiles: From Molecules to Nanostructures to Biomaterials", Peptide Sci 94(1):1-18 (2010).
Dehsorkhi et al., "Self-assembling amphiphilic peptides," Journal of Peptide Science, 20(7):453-467 (2014).
Delcour, "Outer Membrane Permeability and Antibiotic Resistance," Biochim Biophys Acta, 1794(5):808-816 (2009).
Domingues et al., "Comparative Study of the Mechanism of Action of the Antimicrobial Peptide Gomesin and Its Linear Analogue: The Role of the ?—Hairpin Structure," Biochimica et Biophysica Acta, 1848:2414-2421 (2015).
Geilich et al., "Silver Nanoparticle-Embedded Polymersome Nanocarriers for the Treatment of Antibiotic-Resistant Infections," Nanoscale, 7:3511-3519 (2015).
GenBank: EFE14510.1, published Aug. 4, 2012, directed to the sequence of Can protein B-type domain protein of *Clostridium* sp. M62/1 (2012).
Hancock et al., "Peptide Antibiotics," Antimicrob Agents Chemother, 43:1317-1323 (1999).
Juba et al., "Helical cationic antimicrobial peptide length and its impact on; membrane disruption," Biochimica et Biophysica Acta, 1848:1081-1091 (2015).
Kim et al., "Fast Detection and Quantification of *Escherichia coli* Using the Base Principle of the Microbial Fuel Cell," J Environ Manage, 130:267-275 (2013).
Kim et al., "Membrane Damage of Bacteria by Silanols Treatment," *Electron. J. Biotechnol.*, 10(2):252-259 (2007).
Li et al., "Effect of a denture base acrylic resin containing silver nanoparticles on Candida albicans adhesion and biofilm formation," Gerodontology, 33(2):209-216 (2016).
Luo et al., "Self-Assembly of Collagen-Mimetic Peptide Amphiphiles into Biofunctional Nanofiber," *ACS Nano*, 5(10):7739-7747 (2011).
Malmsten et al., "Highly Selective End-Tagged Antimicrobial Peptides Derived from PRELP," *PLoS One*, 6:1-13 (2011).
Manzo et al., "Enhanced Amphiphilic Profile of a Short Beta-Stranded Peptide Improves Its Antimicrobial Activity," PloS one, 10:e0116379 (2015).
Meng et al., "Tunable Self-Assembled Peptide Annphiphile Nanostructures," Langmuir 28:5017-5022 (2012).

Mohri et al., "Novel Synthetic Peptides From the C-terminal Heparin Binding Domain of Fibronectin With Heparin Binding Activity," Peptides, 17(6): 1079-1081 (1996).
Morand., "(macro-) Evolutionary ecology of parasite diversity: From determinants of parasite species richness to host diversification," International Journal for Parasitology: Parasites and Wildlife, 4: 80-87 (2015).
Newcomb et al., "Cell Death Versus Cell Survival Instructed by Supramolecular Cohesion of Nanostructures," Nat. Commun, 5:3321 (2014).
Ong et al., "Short Synthetic β-Sheet Forming Peptide Amphiphiles as Broad Spectrum Antimicrobials with Antibiofilm and Endotoxin Neutralizing Capabilities," Adv. Funct. Mater., 23:3682-3692 (2013).
Ong et al., "Strategies Employed in the Design and Optimization of Synthetic Antimicrobial Peptide Amphiphiles with Enhanced Therapeutic Potentials," Adv Drug Deliv Rev, 78:28-45 (2014).
Poulin et al., "Integrating parasitology and marine ecology: Seven challenges towards greater synergy," Journal of Sea Research, 113: 3-10 (2016).
Pulido et al., "A Novel Rnase 3/Ecp Peptide for Pseudomonas Aeruginosa Biofilm Eradication That Combines Antimicrobial, Lipopolysaccharide Binding, and Cell-Agglutinating Activities," *Antimicrob. Agents Chemother*, 60:6313-6325 (2016).
Ramanathan et al., "Amphiphile Nanoarchitectonics: From Basic Physical Chemistry to Advanced Applications," Phys. Chem. Chem. Phys., 15:10580-10611 (2013).
Ringstad et al., "Effect of Peptide Length on the Interaction between Consensus Peptides and DOPC/DOPA Bilayers," Langmuir, 22:5042-5050 (2006).
Schmieder et al., "Insights into Antibiotic Resistance through Metagenomic Approaches," *Future Microbiol*, 7(1):73-89 (2011).
Shao et al., "Controllable Peptide-Dendron Self-Assembly: Interconversion of Nanotubes and Fibrillar Nanostructures," Angew. Chem. Int. Ed., 48:2525-2528 (2009).
Shimazaki et al., "Properties of a Heparin-binding Peptide Derived from Bovine Lactoferrin," Journal of Dairy Science, 81(11): 2841-2849 (1998).
Stahlberg et al., "Oligomeric Structure of the Bacillus Subtilis Cell Division Protein Diviva Determined by Transmission Electron Microscopy," Mol Microbiol, 52(5):1281-1290 (2004).
Stephanopoulos et al., "Self-Assembly for the Synthesis of Functional Biomaterials," *Acta Mater*, 61(3):912-930 (2013).
Sweet et al., "Reprint of 'Diseases in marine invertebrates associated with mariculture and commercial fisheries'," Journal of Sea Research, 113: 28-44 (2016).
Teixeira et al., "Role of lipids in the interaction of antimicrobial peptides with membranes," Progress in Lipid Research, 51:149-177 (2012).
Torrent et al., "Eosinophil Cationic Protein High-Affinity Binding to Bacteria-Wall Lipopolysaccharides and Peptidoglycans," Biochemistry, 47(11):3544-3555 (2008).
Webber et al., "Supramolecular Nanofibers of Peptide Amphiphiles for Medicine," Isr. J. Chem., 53(8):530-554 (2013).
Welsh et al., "Self-Assembled Multivalent RGD-Peptide Arrays—Morphological Control and Integrin Binding," Org. Biomol. Chem., 11:3177-3186 (2013).
Yin et al., "Roles of Hydrophobicity and Charge Distribution of Cationic Antimicrobial Peptides Peptide-Membrane Interactions," J. Biol. Chem., 287(10):7738-7745 (2012).
Yount et al., "Advances in Antimicrobial Peptide Immunobiology," J. Pept. Sci., 84:435-458 (2006).
Zasloff, "Antimicrobial Peptides of Multicellular Organisms," *Nature*, 415:389-395 (2002).
Zhang et al., "Self-Assembled Cationic Amphiphiles as Antimicrobial Peptides Mimics: Role of Hydrophobicity, Linkage Type, and Assembly State," Nanomed, 13(2):343-352 (2016).
Zhang et al., "Self-assembly of surfactant-like peptides and their applications," Science China Chemistry, 57(12): 1634-1645 (2014).

* cited by examiner

HEPARIN-BINDING CATIONIC PEPTIDE SELF-ASSEMBLING PEPTIDE AMPHIPHILES USEFUL AGAINST DRUG-RESISTANT BACTERIA

RELATED APPLICATIONS

This application is a continuation of U.S. patent application Ser. No. 15/832,194, filed Dec. 5, 2017; which claims the benefit of priority to U.S. Provisional Application for Patent Ser. No. 62/430,906, filed Dec. 6, 2016.

SEQUENCE LISTING

The instant application contains a Sequence Listing which has been submitted electronically in ASCII format and is hereby incorporated by reference in its entirety. Said ASCII copy, created on Apr. 7, 2022, is named NEX-02702_SL.txt and is 6,622 bytes in size.

BACKGROUND

Bacterial antibiotic resistance has become a critical threat to global health and the worldwide economy. According to the Center for Disease Control and Prevention (CDC), over 2 million cases of illness, and 23,000 deaths, are caused each year by bacterial drug-resistance in the United States [1]. Moreover, bacteria can develop resistance to a new antibiotic within a few years. Therefore, rather than continually developing new antibiotics that may be ineffective within a short time, there remains a need to develop novel antibacterial agents that target a broad range of bacteria without inducing bacterial drug-resistance.

SUMMARY

In one aspect, the disclosure provides a polypeptide comprising an amphiphilic backbone and a cationic heparin-binding motif peptide.

In another aspect, the disclosure provides a method of antimicrobial treatment, comprising:
  providing a sample comprising a plurality of microorganisms;
  adding to the sample a polypeptide comprising an amphiphilic backbone and a cationic heparin-binding motif peptide;
  thereby killing or inhibiting the growth of at least a portion of the plurality of microorganisms in the sample.

In another aspect, the disclosure provides a method of preventing or suppressing microbial growth on a surface, comprising:
  applying to the surface a polypeptide comprising an amphiphilic backbone and a cationic heparin-binding motif peptide;
  thereby preventing or suppressing microbial growth on the surface.

In another aspect, the disclosure provides a method of preparing self-assembled nanorods comprising the steps of:
  dissolving a plurality of lyophilized polypeptides comprising an amphiphilic backbone and a cationic heparin-binding motif peptide in a solvent to form a mixture;
  mixing the mixture; and
  storing the mixture to allow for supramolecular self-assembly
  thereby preparing self-assembled nanorods. ,

DETAILED DESCRIPTION

Overview

Figure 1A:
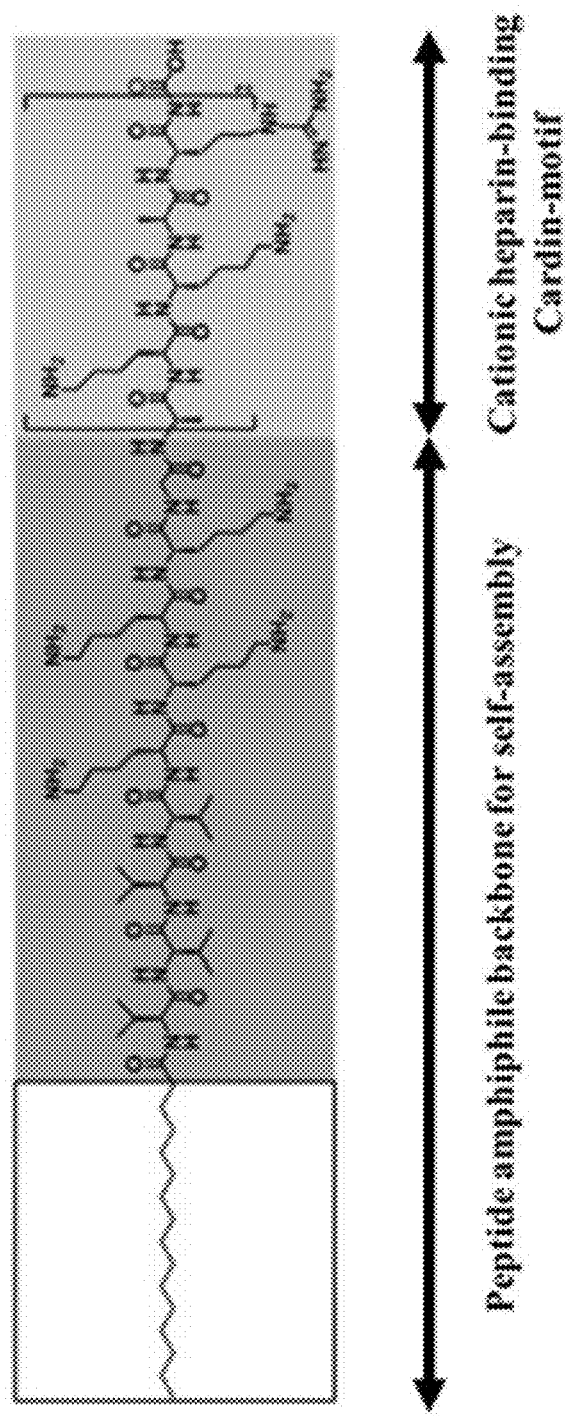
FIG. 1A depicts a schematic illustration of a molecular structure of an exemplary peptide, ACA-PA.

There are four major pathways to the development of bacterial drug resistance: i) alteration in the target site of antimicrobial agents to reduce binding affinity; ii) reducing drug accessibility via increased efflux or decreased influx within the cell; iii) drug inactivation; and iv) tolerance that results in the survival of bacteria during inhibited bacteria growth [2].

Antibiotic-resistance continues to be one of the biggest threats to global health. Antimicrobial peptides (AMPs) have been explored as therapeutic agents to treat antibiotic resistant microbes. Naturally-occurring AMPs can be found in many living organisms, where they serve as defense components in the innate immune system against a broad range of pathogens, including bacteria, viruses, and fungi [3-5]. Unlike conventional antibiotics that mostly rely on receptor-specific pathways to display antibacterial activity, AMPs bind to negatively charged bacteria cell membranes by non-specific physical interactions with bacterial membranes, leading to cell death via membrane disruption. Moreover, AMPs possesses highly selective toxicity in bacteria compared to mammalian cells, which is ascribed to the considerable differences in lipid composition between prokaryotic and eukaryotic cells. In bacterial membranes, the negatively-charged hydroxylated phospholipids, such as phosphatidylglycerol (PG), cardiolipin (CL) and phosphatidylserine (PS), are abundantly present, while mammalian cell membranes are exclusively enriched by more electrically-neutral zwitterionic phospholipids and cholesterol that reduce peptide binding as well as membrane-thinning effects of AMPs [6]. Although some AMPs isolated from natural sources have shown early success as alternatives to antibiotics, their therapeutic applications are limited by their high costs due to long sequences, limited supply, low stability to enzymatic degradation in vivo, and off-target cytotoxicity [7, 8].

To overcome these challenges, sequence and structural features of naturally-occurring AMPs can be leveraged to develop strategies for the design of synthetic AMPs with wider therapeutic windows [9, 10]. Characteristics of natural AMPs (such as cationicity, amphipathicity, and the ability to fold into secondary structures) can be retained in synthetic AMPs, which are key factors for their membrane permeation and mechanisms of antibacterial action. Most AMPs carry a positive net charge from +2 to +9. Once the cationic domain of a peptide initiates attachment with the anionic membrane surface, the hydrophobic domain drives peptide partitioning into the non-polar regions of lipid bilayer to disrupt the membrane [6, 11]. Conjugation of cationic peptides with fatty acids [12] or hydrophobic amino acid residues [13] has been shown to mediate their antimicrobial activity. In addition, AMPs with β-sheet conformation can penetrate bacterial cell membranes via transmembrane channels and display potent antibacterial properties [7]. For instance, a series of short peptides that adopt β-sheet secondary structures on bacterial cell membranes have been shown to exhibit effective antibacterial properties against a broad range of clinically pathogenic bacteria strains, and possessed in vivo efficacy to treat fungal keratitis [9, 14]. β-sheet forming short peptides that can form highly packed nanorods showed enhanced antibacterial activity, which provides significant evidence for the future of self-assembled peptides and their clinical use [15].

A type of self-assembling peptide amphiphile (PA) has been designed to be effective against antibiotic-resistant bacteria. Self-assembly of these PA systems into high aspect ratio and highly organized nanostructures is driven by non-covalent intermolecular interactions [18]. Cylindrical supramolecular structures of PA can be constructed by oligopeptide building blocks containing hydrocarbon chains, β-sheet forming groups via hydrogen bonding, and charged amino acids. These self-assembled nanostructures can be engineered for specific biological functions with a short peptide sequence displayed on the surface. In recent decades, PA systems have been extensively studied for applications including regenerative medicines as well as drug delivery vehicles.

Figure 1B:
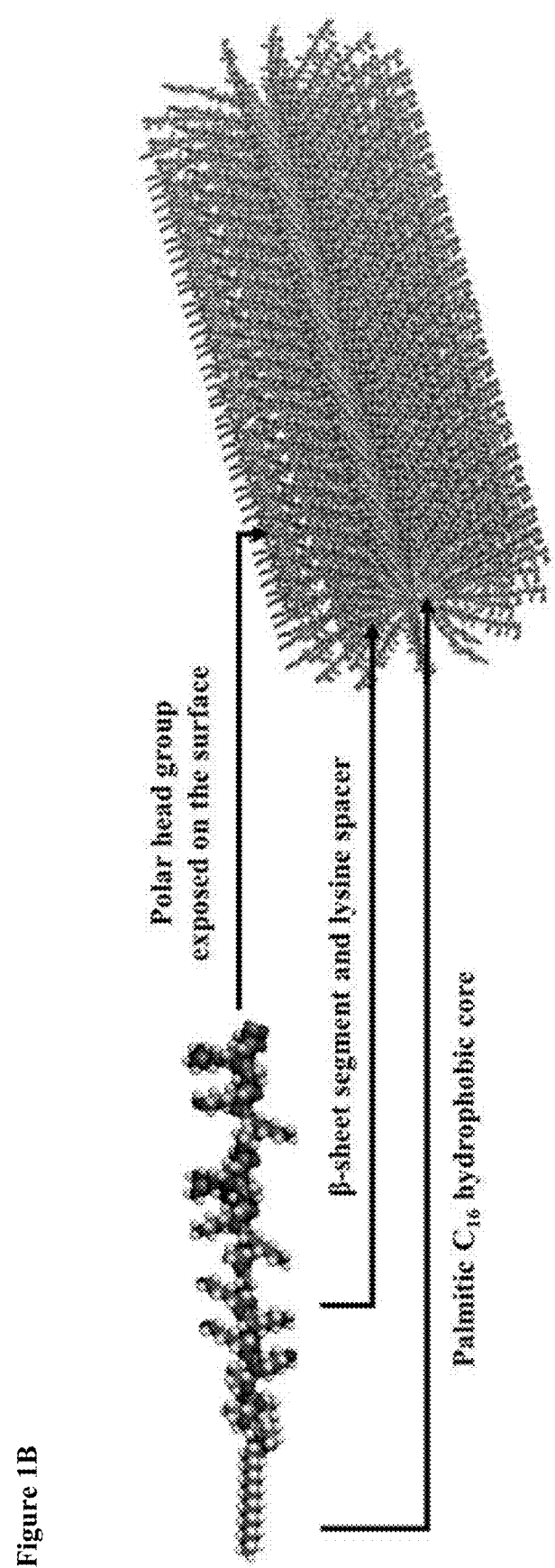
FIG. 1B depicts a schematic illustration of the self-assembly process of an exemplary peptide, ACA-PA, into cylindrical structures in aqueous solution.

Nonetheless, few studies have investigated the potential use of self-assembling PA as therapeutics to treat drug-resistant bacteria. Here, amphiphilic Cardin-motif antimicrobial peptides (ACA-PA) were designed to self-assemble into cylindrical supramolecular structures. For example, this peptide self-assembly is driven by hydrophobic interactions of the hydrophobic palmitic (16 carbon) tail groups, and directed by the β-sheet forming $V_4K_4$ (SEQ ID NO: 1)

peptide backbones into cylindrical shapes. The serial lysine groups act as a spacer and ensure water solubility of the peptide amphiphiles [19, 20]. The ACA-PA was functionalized with the heparin-binding (AKKARA)$_2$ (SEQ ID NO: 2) Cardin-Weintraub motif [21] to initiate attachment with the anionic bacterial cell membranes (FIGS. 1A and 1B). Self-assembling properties of the ACA-PA and the secondary structures were characterized. Antibacterial activity of the peptide was tested on Gram-positive MRSA as well as Gram-negative multi-drug resistant *Escherichia coli* (MDR *E. coli*), which possess resistance to beta-lactam antibiotics [24]. Furthermore, mechanisms for the antibacterial activity, bacterial membrane penetrating effects and cytotoxicity of ACA-PA were examined.

Self-Assembling Peptide Amphiphiles

Herein, self-assembling peptide amphiphiles (PAs) functionalized with heparin-binding Cardin-motifs (SEQ ID NO: 2, (AKKARA)$_2$, where A, K, and R represent alanine, lysine and arginine, respectively) have been designed to combat the drug-resistance of both Gram-positive and Gram-negative bacteria. These cationic amphiphilic Cardin-motif antimicrobial (ACA) peptides could self-assemble in water into nanorods 10 nm in diameter. Unlike typical small molecule antibiotics, the self-assembled ACA nanorods were shown to damage the bacterial cell membrane and cause bacterial cell lysis. Such non-specific interactions can reduce the development of drug-resistance, as the entire bacterial cell membrane is the target site of the self-assembled ACA nanorods. In contrast, free (AKKARA)$_2$ peptides (SEQ ID NO: 2, without the self-assembly property) showed little antibacterial activity. Therefore, the unique self-assembled ACA nanorods with heparin-binding Cardin-motif sequences are promising antibacterial agents to treat antibiotic-resistant bacteria.

In some embodiments, PAs functionalized with the Cardin-motif can self-assemble into nanorods. In some embodiments, PAs functionalized with the Cardin-motif can self-assemble into nanofibers. In some embodiments, PAs functionalized with the Cardin-motif can self-assemble into bundled and elongated nanofibers.

In some embodiments of the self-assembling peptide amphiphiles disclosed herein, the PA is a polypeptide comprising an amphiphilic backbone and a cationic heparin-binding motif peptide. In some embodiments, the amphiphilic backbone comprises a hydrophobic portion and a beta-sheet forming segment.

In some embodiments of the self-assembling peptide amphiphiles disclosed herein, the polypeptide is represented by:

$R^1$-$y^1$-$y^2$ wherein $R^1$-$y^1$ is an amphiphilic backbone; and $y^2$ is a cationic heparin-binding motif peptide.

In some embodiments, $R^1$ is an alkyl group or an alkenyl group. In some embodiments, $R^1$ is a $C_{10}$-$C_{22}$ alkyl group or a $C_{10}$-$C_{22}$ alkenyl group. In some embodiments, $R^1$ is a $C_{12}$-$C_{22}$ alkyl group or a $C_{12}$-$C_{22}$ alkenyl group. In some embodiments, $R^1$ is selected from the group consisting of $C_{12}$, $C_{14}$, $C_{16}$, C16:1, $C_{18}$, C18:1, C18:2, C18:3, $C_{20}$, C20:1, C20:4, C20:5, $C_{22}$, C22:1, and C22:6. In some embodiments, $R^1$ is a $C_{16}$ alkyl group.

In some embodiments, $y^1$ is a hydrophilic polypeptide. In some embodiments, $y^1$ has the following sequence (SEQ ID NO: 3):

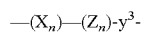

wherein, independently for each occurrence:

X is I, L, or V;

Z is K or R;

n is 2, 3, 4, 5, 6, 7, 8, 9, or 10; and $y^3$ is absent, A, or G.

In some embodiments of $y^1$ disclosed herein, each X is I, L, or V. In some embodiments, X is I. In some embodiments, X is L. In some embodiments, X is V.

In some embodiments, each Z is K or R. In some embodiments, Z is K. In some embodiments, Z is R.

In some embodiments, each n is 2, 3, 4, 5, 6, 7, 8, 9, or 10. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, $y^3$ is absent, A, or G. In some embodiments, $y^3$ is absent. In some embodiments, $y^3$ is A. In some embodiments, $y^3$ is G.

In some embodiments, $y^1$ has the following sequence $V_4K_4$ (SEQ ID NO: 1) or $V_4K_4G$ (SEQ ID NO: 4).

In some embodiments, $y^2$ is a cationic heparin-binding motif peptide. In some embodiments, $y^2$ has the following sequence (SEQ ID NO: 5):

wherein, independently for each occurrence:

W is A or G;

Z is K or R; and m is 2, 3, 4, 5, 6, 7, 8, 9, or 10.

In some embodiments of $y^2$ disclosed herein, each W is A or G. In some embodiments, W is A. In some embodiments, W is G.

In some embodiments, each Z is K or R. In some embodiments, Z is K. In some embodiments, Z is R.

In some embodiments, m is 2, 3, 4, 5, 6, 7, 8, 9, or 10. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10.

In some embodiments, $y^2$ is -(AKKARA)$_m$ (SEQ ID NO: 6).

In some embodiments, each of these PAs contains a hydrophobic portion (e.g., a C16 hydrocarbon group), a beta-sheet forming segment (e.g., SEQ ID NO: 1, V4K4), and a cationic heparin-binding functional group (e.g., SEQ ID NO: 2, (AKKARA)$_2$).

In some embodiments of the PAs disclosed herein, the PA has the following sequence $C_{16}$-$V_4K_4G$(AKKARA)$_2$ (SEQ ID NO: 7).

In some embodiments, the self-assembled nanorods are formed by non-covalent forces including hydrogen bonds and hydrophobic interactions, and display the cationic Cardin-motif on the surface.

In some embodiments of the polypeptides disclosed herein, the polypeptide is incorporated into an article. In some embodiments, for example, the article is selected from filters (e.g., hand-held water filters), membranes, packing materials (e.g., for foods, agriculture, paints, etc.), flow cells, filter gaskets, gloves, masks, garments, wound dressings, implants, catheters, and other medical devices. In some embodiments, the article is sterile.

Methods of Use

In some embodiments, PAs exhibited promising antibacterial properties.

In some embodiments, the addition of self-assembling peptide amphiphilic backbones to cationic heparin-binding peptides significantly improves the antibacterial properties of the peptides, while the free heparin-binding peptides only have little antibacterial effects.

In some embodiments, self-assembly of the PAs is important to the antibacterial effects. For example, once the nanorods are self-assembled, the bactericidal effects towards Gram-negative bacteria are significantly more pronounced.

In some embodiments, the self-assembled ACA nanorods can be easily prepared by dissolving the lyophilized peptides in water. Since the self-assembly is driven by non-covalent intermolecular interactions, complex chemical synthesis is not required for the preparation of the nanorods.

In some embodiments, these self-assembled ACA nanorods can kill a broad range of bacteria including the antibiotic-resistant strains. In contrast, many current antibiotics are only effective to either Gram-negative or Gram-positive bacteria. For example, ciprofloxacin and ofloxacin specifically target the DNA enzyme in Gram-negative bacteria, and moxifloxacin and gatifloxacin are more effective against Gram-positive bacteria.

In some embodiments, the cationic self-assembled nanorods can attach on the negatively charged bacterial membranes by electrostatic interactions, so the target side of the nanorods is the whole bacterial membrane, which makes it more challenging for the bacteria to develop resistance.

In some embodiments, ACA nanorods may cause the formation of transmembrane pores on the surface of cell membranes, resulting in cytoplasmic leakage followed by cell lysis.

Since peptide-based self-assembled materials are biodegradable, these ACA nanorods can be degraded after displaying their antibacterial effects by proteolysis. Otherwise, undesirable retention of particles (such as synthetic polymeric and liposome materials) can cause systemic toxicity in liver, spleen and kidney.

In another aspect, the disclosure provides a method of antimicrobial treatment, comprising:

- providing a sample comprising a plurality of microorganisms;
- adding to the sample a plurality of polypeptides comprising an amphiphilic backbone and a cationic heparin-binding motif peptide, thereby killing or inhibiting the growth of at least a portion of the plurality of microorganisms in the sample.

In some embodiments, at least a portion of the plurality of microorganisms is killed. In some embodiments, the growth of at least a portion of the plurality of microorganisms is inhibited.

In another aspect, the disclosure provides a method of preventing or suppressing microbial growth on a surface, comprising:

- applying to the surface a plurality of polypeptides comprising an amphiphilic backbone and a cationic heparin-binding motif peptide, thereby preventing or suppressing microbial growth on the surface.

In some embodiments, microbial growth on the surface is prevented. In some embodiments, microbial growth on the surface is suppressed.

In some embodiments of the methods disclosed herein, the surface coating is on an article. In some embodiments, for example, the article is selected from filters (e.g., hand-held water filters), membranes, packing materials (e.g., for foods, agriculture, paints, etc.), flow cells, filter gaskets, gloves, masks, garments, wound dressings, implants, catheters, and other medical devices. In some embodiments, the article is sterile.

In some embodiments of the methods disclosed herein, the sample further comprises water.

In some embodiments of the methods disclosed herein, the plurality of polypeptides comprising an amphiphilic backbone and a cationic heparin-binding motif peptide is any one of the self-assembling peptide amphiphiles disclosed herein. In some embodiments, the amphiphilic Cardin-motif antimicrobial (ACA) peptides self-assemble.

In some embodiments, the microorganism is a bacterium, a virus, a fungus, or a parasite. In some embodiments, the microorganism is antibiotic-resistant.

In some embodiments, the microorganism is a Gram-negative bacterium. In some embodiments, the microorganism is a Gram-positive bacterium. In some embodiments, for example, the microorganism is at least one bacterium selected from anthrax, *Bacilli, Bordetella, Borrelia*, botulism, *Brucella, Burkholderia, Campylobacter, Chlamydia*, cholera, *Clostridium, Gonococcus, Corynebacterium*, diptheria, *Enterobacter, Enterococcus, Erwinia, Escherichia, Francisella, Haemophilus, Heliobacter, Klebsiella, Legionella, Leptospira, leptospirosis, Listeria*, Lyme's disease, meningococcus, *Mycobacterium, Mycoplasma, Neisseria, Pasteurella, Pelobacter*, plague, *Pneumonococcus, Proteus, Pseudomonas, Rickettsia, Salmonella, Serratia, Shigella, Staphylococcus, Streptococcus*, tetanus, *Treponema, Vibrio, Yersinia* and *Xanthomonas*. In some embodiments, the microorganism is *Staphylococcus aureus* (*S. aureus*) or methicillin-resistant *S. aureus* (MRSA). In some embodiments, the microorganism is *Escherichia coli* (*E. coli*) or multidrug-resistant *E. coli* (MDR *E. coli*).

In some embodiments, for example, the microorganism is at least one virus selected from *Adenoviridae, Papillomaviridae, Polyomaviridae, Herpesviridae, Poxviridae, Hepadnaviridae, Parvoviridae, Astroviridae, Caliciviridae, Picornaviridae, Coronoviridae, Flaviviridae, Retroviridae, Togaviridae, Arenaviridae, Bunyaviridae, Filoviridae, Orthomyxoviridae, Paramyxoviridae, Rhabdoviridae*, and *Reoviridae*. In certain embodiments, the virus may be arboviral encephalitis virus, adenovirus, herpes simplex type I, herpes simplex type 2, Varicella-zoster virus, Epstein-burr virus, cytomegalovirus, herpesvirus type 8, papillomavirus, BK virus, coronavirus, echovirus, JC virus, smallpox, Hepatitis B, bocavirus, parvovirus B19, astrovirus, Norwalk virus, coxsackievirus, Hepatitis A, poliovirus, rhinovirus, severe acute respiratory syndrome virus, Hepatitis C, yellow fever, dengue virus, West Nile virus, rubella, Hepatitis E, human immunodeficiency virus (HIV), human T-cell lymphotropic virus (HTLV), influenza, guanarito virus, Junin virus, Lassa virus, Machupo virus, Sabia virus, Crimean-Congo hemorrhagic fever virus, ebola virus, Marburg virus, measles virus, molluscum virus, mumps virus, parainfluenza, respiratory syncytial virus, human metapneumovirus, Hendra virus, Nipah virus, rabies, Hepatitis D, rotavirus, orbivirus, coltivirus, vaccinia virus, and Banna virus.

In some embodiments, for example, the microorganism is at least one fungus selected from *Aspergillus* (*fumigatus, niger*, etc.), *Basidiobolus* (*ranarum*, etc.), *Blastomyces dermatitidis, Candida* (*albicans, krusei, glabrata, tropicalis*, etc.), *Coccidioides immitis, Cryptococcus* (*neoformans*, etc.), eumycetoma, *Epidermophyton* (*floccosum*, etc.), *Histoplasma capsulatum, Hortaea werneckii, Lacazia loboi, Microsproum* (*audouinii, nanum* etc.), *Mucorales* (*mucor, absidia, rhizophus*), *Paracoccidioides brasiliensis, Rhino-*

*sporidium seeberi*, *Sporothrix schenkii*, and *Trichophyton* (*schoeleinii*, *mentagrophytes*, *rubrum*, *verrucosum*, etc.).

In some embodiments, for example, the microorganism is at least one parasite selected from *Acanthamoeba*, *Babesia microti*, *Balantidium coli*, *Entamoeba hystolytica*, *Giardia lamblia*, *Cryptosporidium muris*, *Trypanosomatida gambiense*, *Trypanosomatida rhodesiense*, *Trypanosoma brucei*, *Trypanosoma cruzi*, *Leishmania mexicana*, *Leishmania braziliensis*, *Leishmania tropica*, *Leishmania donovani*, *Toxoplasma gondii*, *Plasmodium vivax*, *Plasmodium ovale*, *Plasmodium malariae*, *Plasmodium falciparum*, *Pneumocystis carinii*, *Trichomonas vaginalis*, *Histomonas meleagridis*, *Secementea*, *Trichuris trichiura*, *Ascaris lumbricoides*, *Enterobius vermicularis*, *Ancylostoma duodenale*, *Naegleria fowleri*, *Necator americanus*, *Nippostrongylus brasiliensis*, *Strongyloides stercoralis*, *Wuchereria bancrofti*, *Dracunculus medinensis*, blood flukes, liver flukes, intestinal flukes, lung flukes, *Schistosoma mansoni*, *Schistosoma haematobium*, *Schistosoma japonicum*, *Fasciola hepatica*, *Fasciola gigantica*, *Heterophyes heterophyes*, and *Paragonimus westermani*.

Formulations

In another aspect, the disclosure provides a method of preparing self-assembled nanorods comprising the steps of:
dissolving a plurality of lyophilized polypeptides comprising an amphiphilic backbone and a cationic heparin-binding motif peptide in a solvent to form a mixture;
mixing the mixture; and
storing the mixture for a period of time to allow for supramolecular self-assembly, thereby preparing self-assembled nanorods.

In some embodiments, the solvent is selected from the group consisting of water, acetone, dimethylsulfoxide, ethanol, methanol, isopropanol, and mixtures thereof. In some embodiments, the solvent is water.

In some embodiments, the mixture is mixed by vortexing, shaking, or agitating. In some embodiments, the mixture is mixed by vortexing.

In some embodiments, the mixture is stored at a temperature below room temperature. In some embodiments, the mixture is stored at a temperature between about −5° C. and about 25° C. In some embodiments, the mixture is stored at a temperature between about 0° C. and about 20° C. In some embodiments, the mixture is stored at a temperature selected from the group consisting of about 20° C., about 19° C., about 18° C., about 17° C., about 16° C., about 15° C., about 14° C., about 13° C., about 12° C., about 11° C., about 10° C., about 9° C., about 8° C., about 7° C., about 6° C., about 5° C., about 4° C., about 3° C., about 2° C., about 1° C., and about 0° C. In some embodiments, the mixture is stored at a temperature of about 4° C.

In some embodiments, the mixture is stored for a period of time of at least 1 h. In some embodiments, the mixture is stored for a period of time of at least 5 h. In some embodiments, the mixture is stored for a period of time of at least 10 h. In some embodiments, the mixture is stored for a period of time of at least 15 h. In some embodiments, the mixture is stored for a period of time of at least 20 h. In some embodiments, the mixture is stored for a period of time of at least 24 h. In some embodiments, the mixture is stored for a period of time of at least 30 h. In some embodiments, the mixture is stored for a period of time of at least 36 h. In some embodiments, the mixture is stored for a period of time of at least 40 h. In some embodiments, the mixture is stored for a period of time of at least 45 h. In some embodiments, the mixture is stored for a period of time of at least 48 h. In some embodiments, the mixture is stored for a period of time selected from the group consisting of about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h, about 25 h, about 26 h, about 27 h, about 28 h, about 29 h, about 30 h, about 31 h, about 32 h, about 33 h, about 34 h, about 35 h, about 36 h, about 37 h, about 38 h, about 39 h, about 40 h, about 41 h, about 42 h, about 43 h, about 44 h, about 45 h, about 46 h, about 47 h, and about 48 h.

In some embodiments, the ACA nanorods in solution can be aimed to serve as antibacterial agents to treat eye infections. In some embodiments, the nanoparticles can be applied directly to the eye as eye drops in solution. In some embodiments, the nanoparticles in solution can be used as a rinsing solution for contact lenses.

The building block peptides of the ACA nanorods can be efficiently produced by a cGMP process at a large scale with low cost. Bioprocessing that produces peptides and proteins from recombinant DNA transfected mammalian cells and bacteria has been widely used by many industrial pharmaceutical companies. Since the peptide amphiphiles of ACA nanorods are short peptides, a gene that encodes this peptide sequence can be transfected into cells or bacteria, and the living organisms are incubated and able to generate the desired peptides exogenously.

Solid-phase peptide synthesis may also be used to produce large quantities of the peptides. Solid-phase peptide synthesis (SPPS), pioneered by Robert Bruce Merrifield, is the standard method for synthesizing peptides and proteins in the lab. SPPS allows for the synthesis of natural peptides which are difficult to express in bacteria, the incorporation of unnatural amino acids, peptide/protein backbone modification, and the synthesis of D-proteins, which consist of D-amino acids.

Small porous beads are treated with functional units ('linkers') on which peptide chains can be built. The peptide will remain covalently attached to the bead until cleaved from it by a reagent, such as anhydrous hydrogen fluoride or trifluoroacetic acid. The peptide is thus 'immobilized' on the solid-phase and can be retained during a filtration process while liquid-phase reagents and by-products of synthesis are flushed away.

The general principle of SPPS is one of repeated cycles of deprotection-wash-coupling-wash. The free N-terminal amine of a solid-phase attached peptide is coupled to a single N-protected amino acid unit. This unit is then deprotected, revealing a new N-terminal amine to which a further amino acid may be attached. The superiority of this technique partially lies in the ability to perform wash cycles after each reaction, removing excess reagent with all of the growing peptide of interest remaining covalently attached to the insoluble resin.

Liquid-phase peptide synthesis is a classical approach to peptide synthesis. It has been replaced in most labs by solid-phase synthesis; however, it retains usefulness in large-scale production of peptides for industrial purposes.

Definitions

Unless otherwise defined herein, scientific and technical terms used in this application shall have the meanings that are commonly understood by those of ordinary skill in the art. Generally, nomenclature used in connection with, and techniques of, chemistry described herein, are those well-known and commonly used in the art.

The term "acyl" is art-recognized and refers to a group represented by the general formula hydrocarbylC(O)—, preferably alkylC(O)—.

The term "acyloxy" is art-recognized and refers to a group represented by the general formula hydrocarbylC(O)O—, preferably alkylC(O)O—.

The term "alkoxy" refers to an alkyl group, having an oxygen attached thereto. Representative alkoxy groups include methoxy, trifluoromethoxy, ethoxy, propoxy, tert-butoxy and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Typically, a straight chained or branched alkenyl group has from 1 to about 20 carbon atoms, preferably from 1 to about 10 unless otherwise defined. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. In some embodiments, the alkyl group has from 1 to 8 carbon atoms, from 1 to 6 carbon atoms, from 1 to 4 carbon atoms, or from 1 to 3 carbon atoms. Examples of straight chained and branched alkyl groups include methyl, ethyl, n-propyl, iso-propyl, n-butyl, sec-butyl, tert-butyl, pentyl, hexyl, pentyl and octyl.

Moreover, the term "alkyl" as used throughout the specification, examples, and claims is intended to include both "unsubstituted alkyls" and "substituted alkyls", the latter of which refers to alkyl moieties having substituents replacing a hydrogen on one or more substitutable carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$," when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylthio", as used herein, refers to a thiol group substituted with an alkyl group and may be represented by the general formula alkylS—.

The term "amide", as used herein, refers to a group

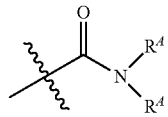

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

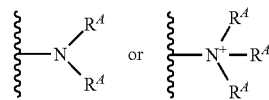

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 20-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle", and "carbocyclic", as used herein, refers to a saturated or unsaturated ring in which each atom of the ring is carbon. Preferably, a carbocyclic group has from 3 to 20 carbon atoms. The term carbocycle includes both aromatic carbocycles and non-aromatic carbocycles. Non-aromatic carbocycles include both cycloalkane rings, in which all carbon atoms are saturated, and cycloalkane rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Preferably, a cycloalkyl group has from 3 to 20 carbon atoms. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carboxy", as used herein, refers to a group represented by the formula —$CO_2H$.

The term "ester", as used herein, refers to a group —$C(O)OR^4$ wherein $R^4$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "heteroaryl" and "hetaryl" include substituted or unsubstituted aromatic single ring structures, preferably 5- to 20-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 20-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Moieties that may be substituted can include any appropriate substituents described herein, for example, acyl, acylamino, acyloxy, alkoxy, alkoxyalkyl, alkenyl, alkyl, alkylamino, alkylthio, arylthio, alkynyl, amide, amino, aminoalkyl, aralkyl, carbamate, carbocyclyl, cycloalkyl, carbocyclylalkyl, carbonate, ester, ether, heteroaralkyl, heterocyclyl, heterocyclylalkyl, hydrocarbyl, silyl, sulfone, or thioether. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfonate" is art-recognized and refers to the group $SO_3H$, or a pharmaceutically acceptable salt thereof.

The term "sulfone" is art-recognized and refers to the group $—S(O)_2—R^A$, wherein $R^A$ represents a hydrocarbyl.

The term "thioether", as used herein, is equivalent to an ether, wherein the oxygen is replaced with a sulfur.

EXEMPLIFICATION

The invention now being generally described, it will be more readily understood by reference to the following, which is included merely for purposes of illustration of certain aspects and embodiments of the present invention, and is not intended to limit the invention.

Example 1: Preparation of the Self-Assembled Peptide Amphiphile Supramolecules All of the peptides were synthesized by and purchased from Biomatik (Ontario, Canada). The peptides had purity>95% by HPLC. The sequences of ACA peptide amphiphiles (ACA-PA) and Bi-Cardin peptides are listed in Table 1. For the self-assembling ACA-PAs, the self-assembly is understood to be driven by hydrophobic interactions of the hydrophobic palmitic (16 carbon) tail groups, and also directed by the β-sheet forming V3K3 (SEQ ID NO: 8) peptide backbones into cylindrical shapes. With the rationally designed peptide backbones, the ACA-PAs can self-assemble into rod-like structures with cationic heparin-binding Cardin motifs exposed on the surface. ACA-PA contain palmitic tail groups and β-sheet forming sequence with hydrophobic oligopeptide blocks, thereby allowing the peptide amphiphiles to self-assemble into elongated structures with high aspect ratios. Heparin-binding Cardin motif peptide sequence was incorporated in the C-terminus of the peptide to potentiate antibacterial activities against a broad spectrum of bacteria.

To prepare the self-assembled supramolecules of the peptide amphiphiles, lyophilized ACA-PA powders were resuspended in deionized water (DI water, Milli-Q system). Peptide amphiphile solutions were vortexed, and then stored at 4° C. for at least 18 h to allow for supramolecular self-assembly. The solutions of the CVK peptide and Bi-Cardin peptide were also prepared by the same method. In all the experiments, the peptides were dissolved in autoclaved deionized water.

TABLE 1

Peptide Sequences and Molecular Weights of Exemplary Peptides.

| Peptide Name | Sequence | Molecular Weight (Da) | CMC (µM) |
|---|---|---|---|
| ACA-PA | $C_{16}$-$V_4K_4G(AKKARA)_2$ (SEQ ID NO: 7) | 2475.28 | 45.7 |
| CVK-PA | $C_{16}$-$V_4K_4$ (SEQ ID NO: 1) | 1165.67 | 50.1 |
| Bi-Cardin | $(AKKARA)_2$ (SEQ ID NO: 2) | 1269.57 | N/A |

Figure 2A:
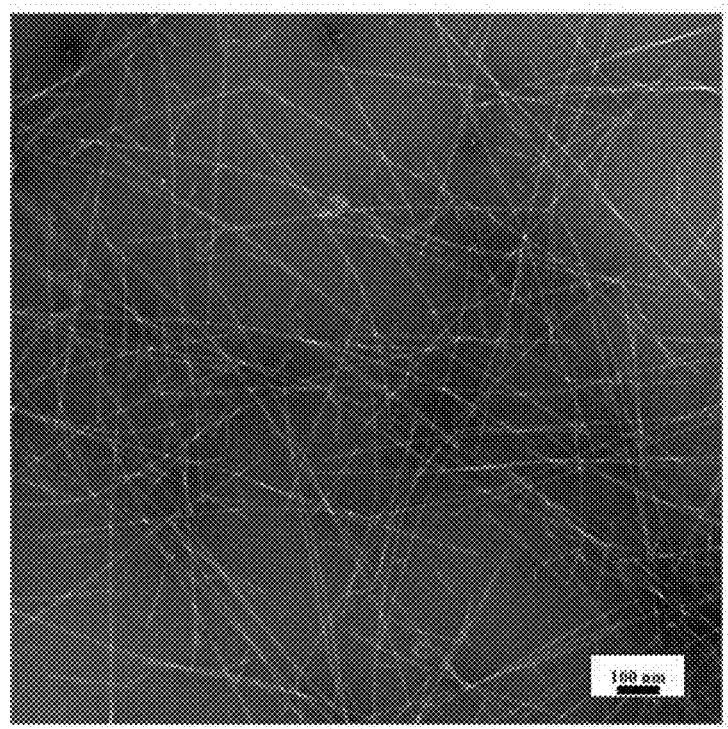
FIG. 2A depicts a transmission electron microscope (TEM) image of the self-assembled morphology of a peptide, CVK-PA.
Figure 2B:
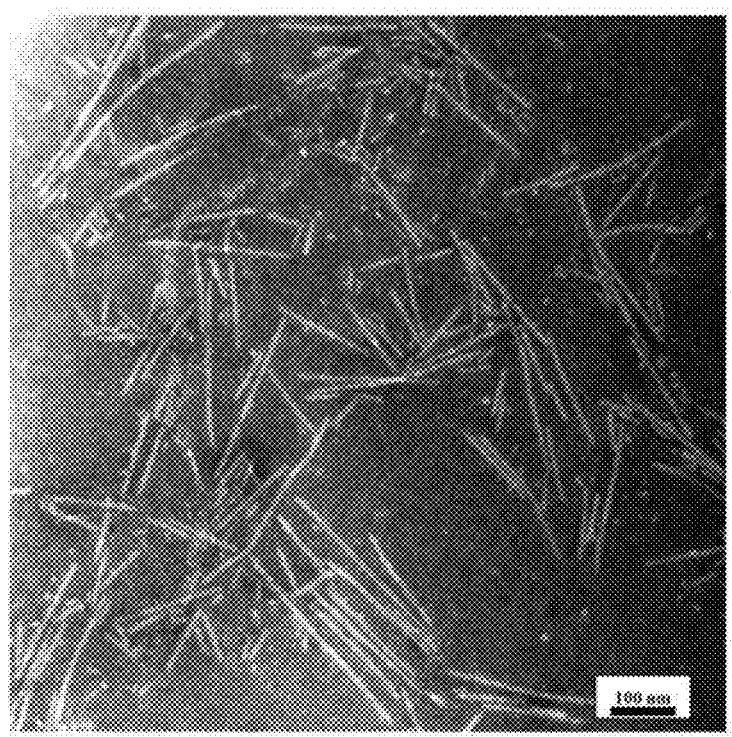
FIG. 2B depicts a TEM image of the self-assembled morphology of an exemplary peptide, ACA-PA, at 1 mg/mL.
Figure 2C:
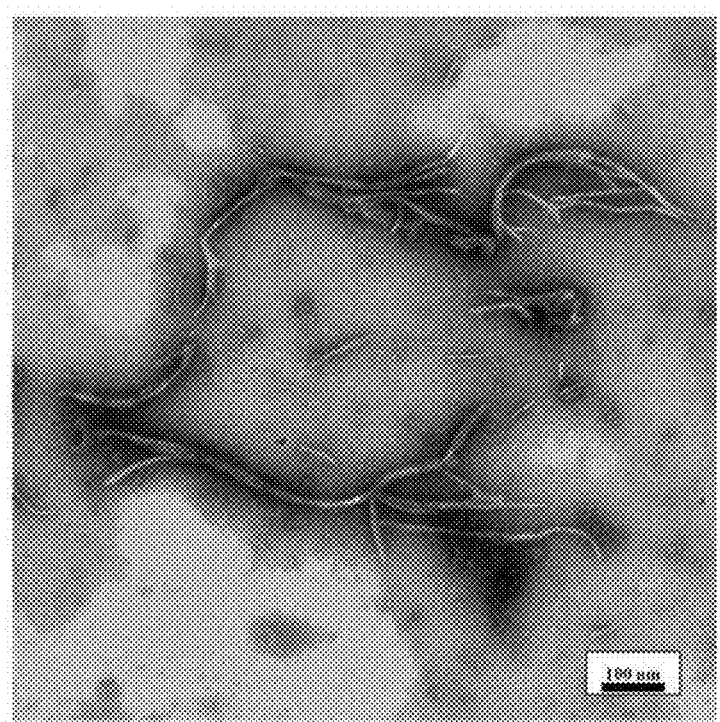
FIG. 2C depicts a TEM image of the self-assembled morphology of an exemplary peptide, ACA-PA, at 2 mg/mL.

Example 2: Transmission Electron Microscopy (TEM) Characterization of the Self-Assembled Structures The self-assembled structure of each PA was observed by TEM. As FIG. 2A shows, the CVK-PA formed into uniform nanofibers with length in microns, and about 6 nm diameter. On the other hand, the self-assembled structure of ACA-PA can be influenced by concentration. At the concentration of 2 mg/mL TEM revealed bundled and elongated nanofibers of ACA-PA (FIG. 2C), whereas nanorods with diameters from 7 to 10 nm were observed at the concentration of 1 mg/mL (FIG. 2B). The Bi-Cardin peptide that solely contains a heparin-binding group did not form any organized structure in solution.

Morphology characterization using TEM indicated that the formation of long nanofibers for the CVK-PA measuring micrometers in length. The ACA-PA were also able to self-assemble into cylindrical supramolecular structures but with relatively shorter lengths. Without wishing to be bound by any theory, the addition of cationic Cardin-motif groups to the peptide backbone may have inhibited the formation of long nanofibers. Self-assembly is believed to be a result of a dynamic balance between the hydrophobic interactions of the alkyl tail groups and the opposing repulsive forces of the charged head groups. As the PAs aggregate and grow into cylindrical structures, the electrostatic repulsion between like-charged residues may limit the dimensions of the resulting supramolecular structures [17, 26, 27, 29]. Interestingly, the self-assembled structures of ACA-PA exhibited morphology transition from nanorod structures to bundle-like, longer fibers through the increase of concentration.

The self-assembled morphologies of peptide amphiphiles in water were observed by TEM (JEM-1010, Peabody, MA). Each sample was mounted on a 300-mesh copper-coated carbon grid (Electron Microscopy Sciences, Hatfield, PA), and then negatively stained with a 1.5% phosphotungstic acid solution (1.5% PTA). Before imaging, all the samples were air-dried for about 10 minutes. In all cases, samples were characterized at an accelerating voltage at 80 kV.

Example 3: Circular Dichroism (CD) Measurements

As the circular dichroism spectra showed, the self-assembly of these ACA nanorods was directed by the β-sheet secondary structure which resulted from the designed peptide backbones, which plays an important role in insertion of the nanorods into bacterial membranes.

Figure 3A:
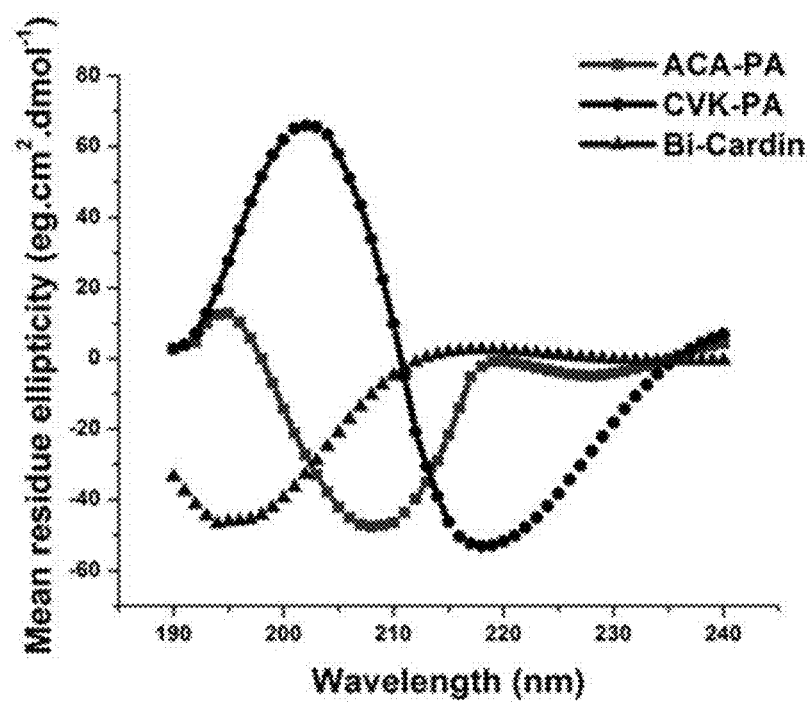
FIG. 3A depicts circular dichroism (CD) spectra showing the secondary structure of exemplary peptides at concentrations of 0.4 mM in water.
Figure 3B:
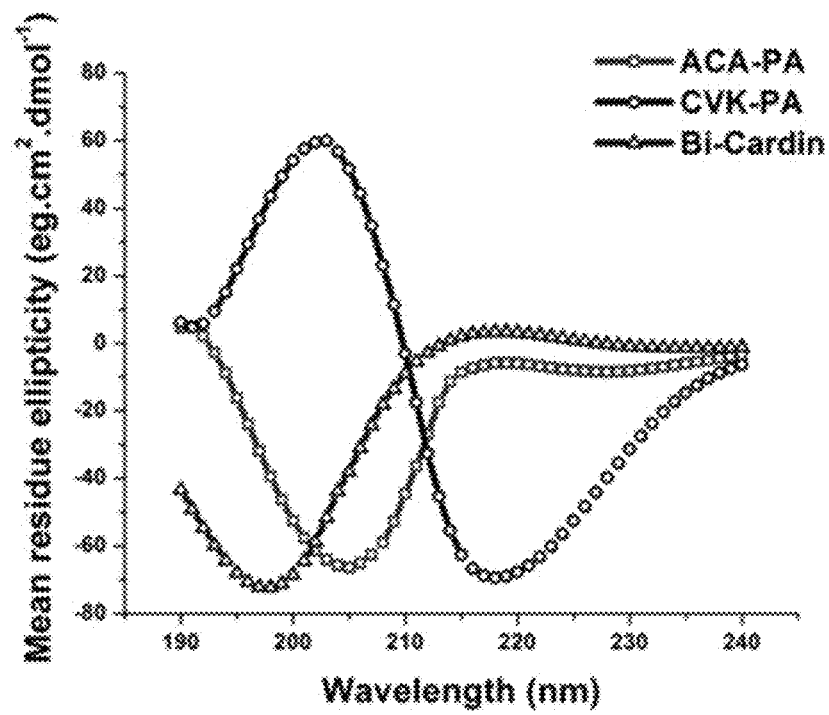
FIG. 3B depicts CD spectra showing the secondary structure of exemplary peptides at concentrations of 0.3 mM in prokaryotic mimicking liposome vesicles.
Figure 3C:
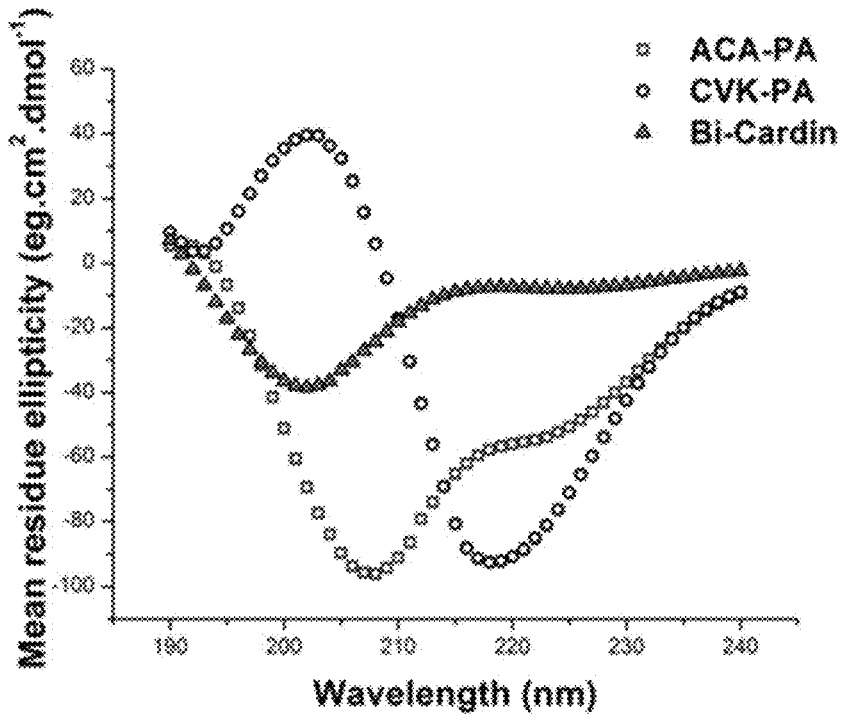
FIG. 3C depicts CD spectra showing the secondary structure of exemplary peptides in 25 mM SDS solution.
Figure 4A:
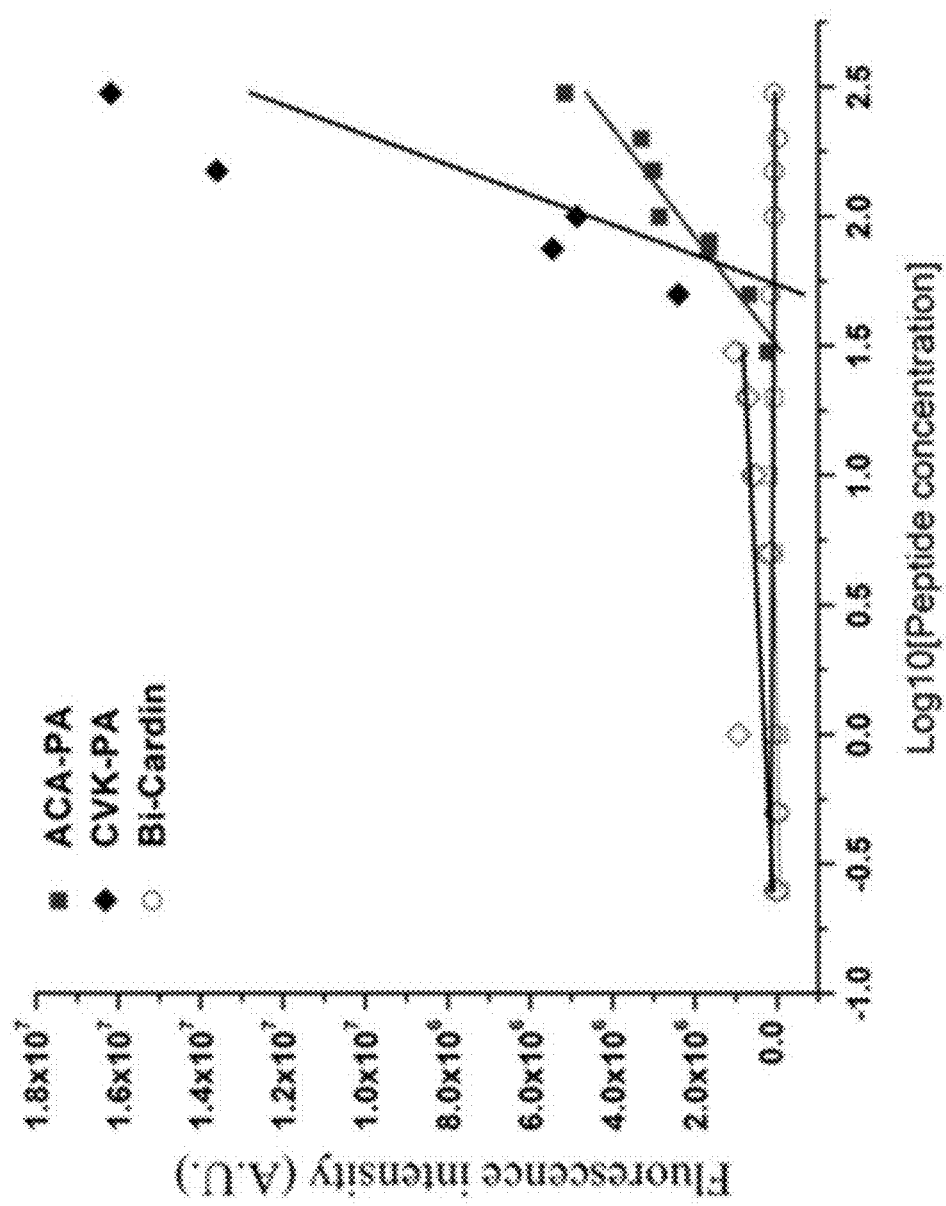
FIG. 4A depicts fluorescence intensity of the Nile Red dye (Ex=550 nm) against $\log_{10}$ values of the peptide concentration.
Figure 4B:
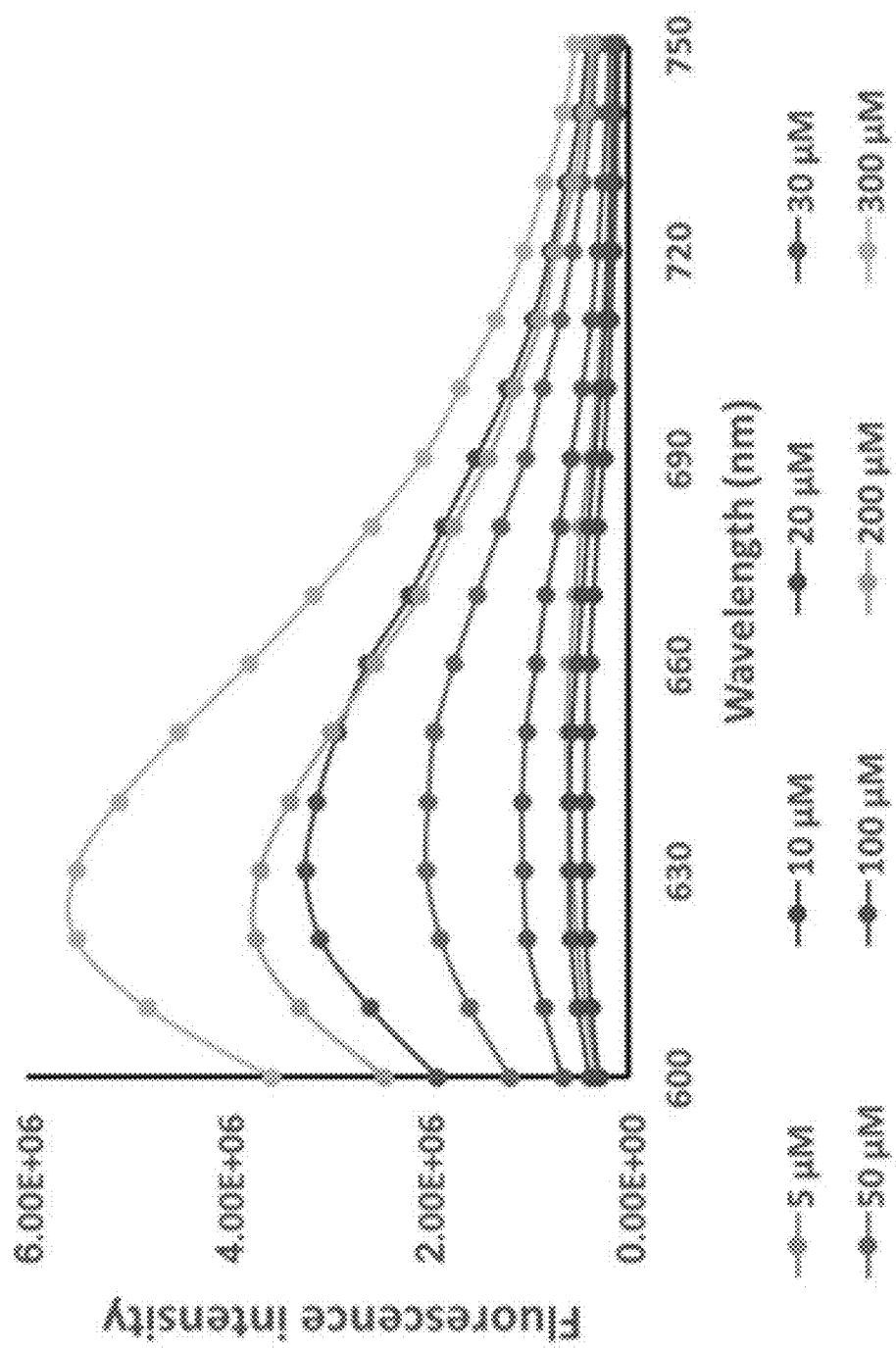
FIG. 4B depicts fluorescence intensity of the Nile Red dye at different concentrations of an exemplary peptide, ACA-PA.
Figure 4C:
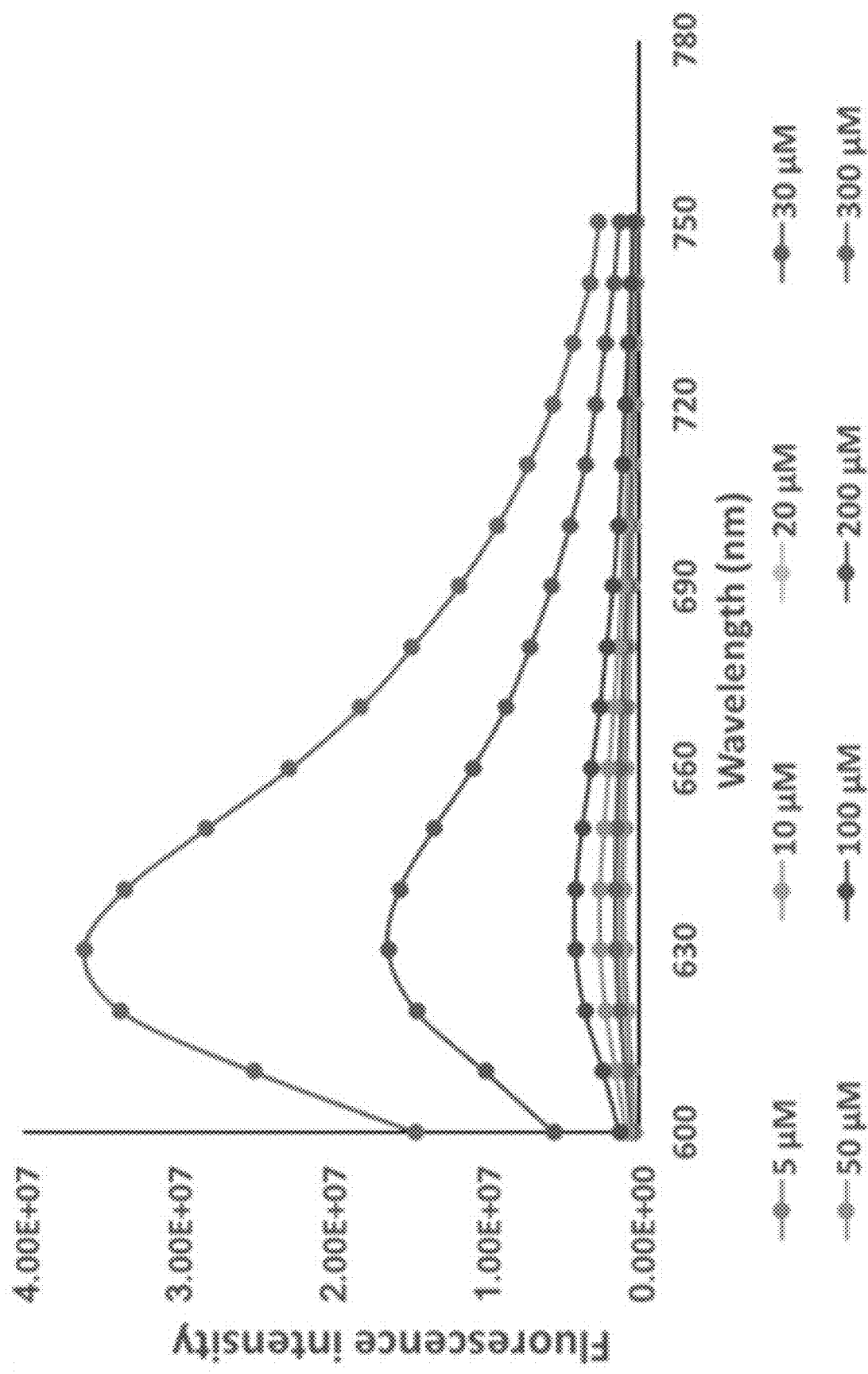
FIG. 4C depicts fluorescence intensity of the Nile Red dye at different concentrations of a peptide, CVK-PA.
Figure 4D:
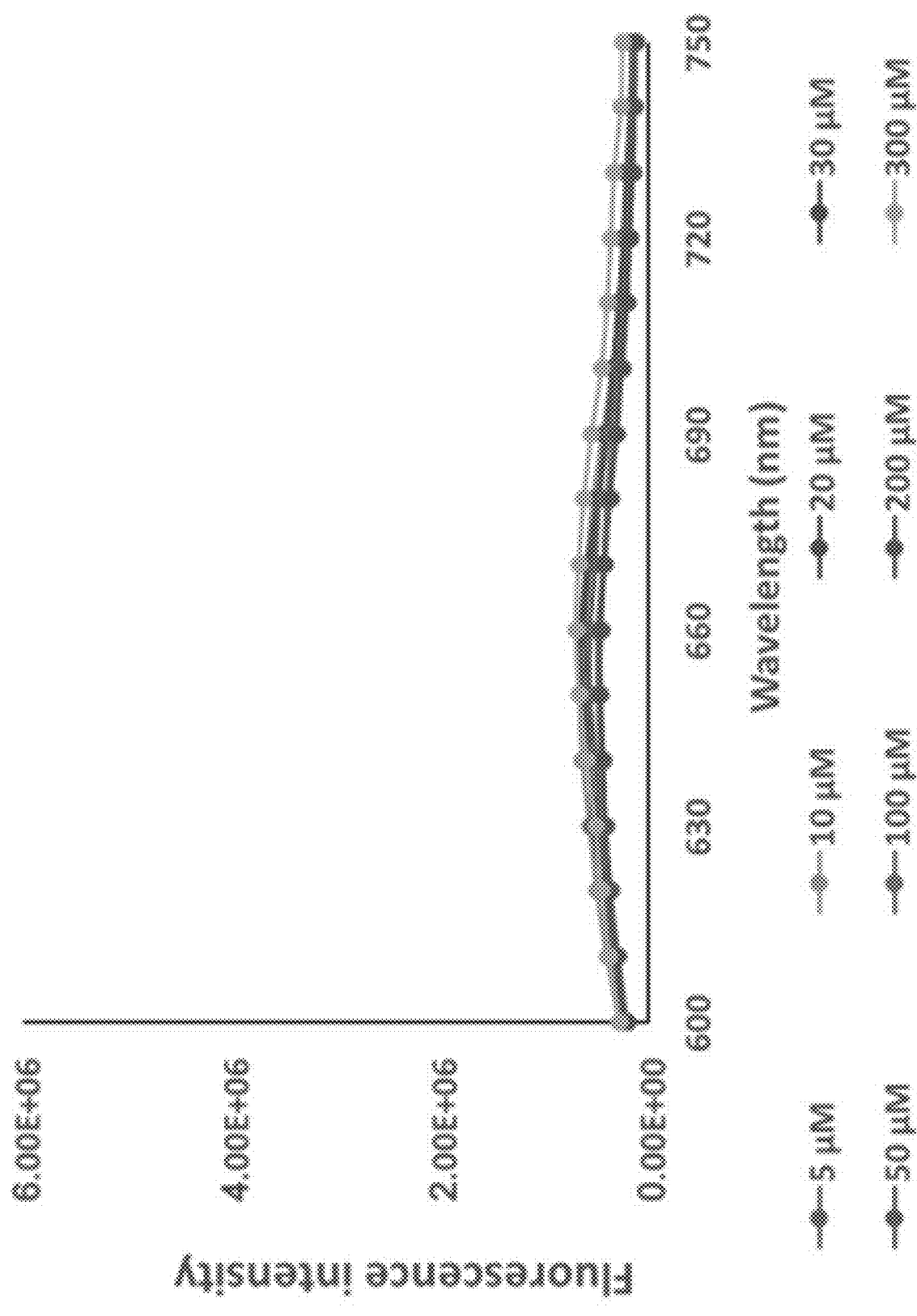
FIG. 4D depicts fluorescence intensity of the Nile Red dye at different concentrations of Bi-Cardin peptide.

In water, the CVK-PA adopted β-sheet secondary structure as FIG. 3A shows a large positive peak at 203 nm and a negative peak at 218 nm. The CD spectra of ACA nanorods underwent a blue-shift, which was characterized by a positive peak at 195 nm with reduced intensity and a large negative peak at 208 nm (FIG. 3A). The CD spectra of the Bi-Cardin peptide indicated the random-coiled structure characterized by a negative peak at around 198 nm (FIG. 3A). In the presence of prokaryotic mimicking lipid vesicles, all the peptide remained their secondary structures as characterized in water (FIG. 3B). In membrane mimetic SDS solution (25 mM), the CVK-PA were able to maintain the β-sheet secondary structure, whereas the ACA-PA showed α-helix secondary structure with two negative peaks at 208 nm and 225 nm (FIG. 3C).

As characterized by CD measurements, spectra of the CVK-PA clearly indicated a well-ordered β-sheet secondary conformation, which can be exerted by the formation of packed hydrophobic cores and β-sheet forming intermolecular hydrogen bonds. Regarding the ACA-PA, functionalization of the cationic heparin-binding sequence caused a blue-shift on the CD spectra, leading to the spectra with 10 nm lower peak wavelengths and reduced ellipticity in the positive peak. Without wishing to be bound by any particular theory, this may be a consequence of increased positively charge and decreased peptide/peptide interactions [34]. The conformational contribution induced by the Cardin-motif groups may be excluded since: i) the Bi-Cardin peptide are unstructured in solution as measured by CD in this work, and ii) the free Cardin-motif peptide possesses low α-helix content [23]. Investigation of peptide secondary structures in lipidic environments suggests that both ACA-PA and CVK-PA can maintain their conformational characteristics in prokaryotic membranes. Interactions with the prokaryotic mimicking liposome vesicles also resulted in higher band intensity in the CD spectra of ACA-PA and CVK-PA, which can be attributed to peptide accumulation on the surface of anionic liposome vesicles [34]. It is also likely that the ACA-PA can exhibit transition to α-helix structure in a micelle-forming and membrane-mimetic SDS solution.

The secondary structures of the peptides were characterized by a J-715 spectropolarimeter (JASCO Analytical Instruments, Easton, MD, USA). The 0.4 mM solutions of each peptide were prepared in degassed DI water.

To study the secondary structures of peptides under membrane-mimetic conditions, each peptide was suspended in either prokaryotic membrane mimicking liposome vesicles or sodium dodecyl sulfate (SDS) solution (Thermo Fisher Scientific, Waltham, MA, USA). Prokaryotic membrane mimicking liposome vesicles were prepared as previously described [12]. 1,2-Dilauroyl-sn-glycero-3-phosphoethanolamine (DLPE) and 1,2-dilauroyl-sn-glycero-3-[phosphor-rac-(1-glycerol)] (DLPG) were dissolved in chloroform to a molar ratio of 7:3. A thin film of lipids was formed by evaporating the solvent under vacuum at room temperature for 3 hours. The thin film was then rehydrated in DI water to a concentration of 2.4 mM, followed by extrusion for 21 times with a 100 nm Millipore polycarbonate filter. Structures of the resulting DLPE/DLPG liposome vesicles were confirmed by TEM characterization. Next, peptide solutions were diluted in liposome vesicle solution or SDS solution. The peptide concentrations were fixed at 0.4 mM, whereas the final concentration of liposome vesicles and SDS solution were 0.3 mM and 25 mM, respectively.

For CD measurements, 200 µL of each sample was transferred into a 1 mm path length quartz cuvette (Hellma, Germany). The CD spectra were collected between wavelengths of 190 nm to 240 nm at a scan rate of 10 nm/min, and expressed as the average of three scans. All the measurements were performed at room temperature.

Example 4: Determination of the Critical Micelle Concentration (CMC)

First, the solvatochromic probe Nile Red was used to examine the threshold concentrations for the spontaneous aggregation induced by hydrophobic collapse of peptides. Once the supramolecular structures of PA self-assemble in water at their CMC, the Nile Red dye can be solubilized in the hydrophobic cores of the PA assemblies, displaying an enhanced fluorescent intensity [28, 29]. Consequently, the fluorescent intensity maxima of Nile Red were at the emission wavelength of 630 nm in the solutions of CVK-PA and ACA-PA, whereas the emission wavelength was located at 660 nm in the Bi-Cardin peptide solutions (FIG. 4A-4D). The CMC of each peptide was also shown in Table 1 and FIG. 4A. Both CVK-PA and ACA-PA assembled at the concentrations of 45 µM and 50.1 µM, respectively, demonstrating the similar aggregation concentrations of these two types of PA. Without wishing to be bound by any theory, ACA-PA have similar CMC as the CVK-PA, which may be the result of consonant hydrophobicity of the identical aliphatic tail groups. The Bi-Cardin peptide did not induce such fluorescent enhancement for all the concentrations tested, so it did not self-assemble.

The solvatochromic Nile Red dye (9-diethylamino-5-benzo[a]-phenoxazinone, Thermofisher, Waltham, MA, USA) was used to determine the CMC of each peptide. This dye is nearly non-fluorescent in polar solvents but undergoes a blue shift emission once incorporated into hydrophobic environments. Briefly, the stock solution of Nile Red (2.5 mM) was prepared in ethanol and then stored in −20° C. before use. 500 µL of the peptide solution ranging from 0.25 to 300 µM were prepared by serial dilution. The dye solution was diluted by 1,000-fold after 0.5 µL of the 2.5 mM Nile Red stock solution was placed into 500 µL of each peptide solution. The solutions were then mixed, and 100 µL of each solution were transferred onto a 96-well plate (each sample was triplicate). The emission spectra of Nile Red in samples was collected from 600 to 750 nm wavelengths at 5 nm intervals with an excitation wavelength of 550 nm using a spectrophotometer (SpectraMax M3, Molecular Devices, Molecular Devices, Sunnyvale, CA, USA). To estimate the CMC of each peptide, the corrected fluorescent intensity ($I_{f,corrected}$) of Nile Red at its emission wavelength for each peptide solution was calculated using equation: $I_{f,corrected} = I_{f,sample} - I_{f,water}$, where $I_{f,sample}$ is the average of the triplicate fluorescent intensity measurements in the sample and $I_{f,water}$ is the fluorescent intensity of Nile Red in water without the peptide. The measurements of the corrected fluorescent intensity were plotted against the log 10 values of concentration of each peptide, then the CMC value was determined at the point of intersection of the plot of log peptide concentration and fluorescent intensity of Nile Red.

Example 5: Assessment of Bacterial Growth Inhibition

Gram-positive (S. aureus and MRSA) and Gram-negative (E. coli and MDR E. coli) bacteria were incubated with peptide concentrations ranging from 20 to 100 µM, and time-lapsed bacterial growth was monitored for 20 hours by determining the optical density at 562 nm (O.D. 562 nm). The ACA-PA remarkably inhibited the proliferation of both drug-susceptible and drug-resistant bacteria, but demonstrated different inhibitory effects between Gram-negative bacteria and Gram-positive bacteria (FIGS. 5A-5D). Gram-positive bacteria treated with ACA nanorods had a prolonged lag phase as the concentration increased. At the highest concentration tested (100 µM), the time to exponential growth phase of *S. aurues* was delayed by about 18 h (FIG. 5B), and was prolonged by almost 13 h for MRSA (FIG. 5A), while bacteria incubated without ACA-PA entered the exponential growth phase within 4 h. Gram-positive bacteria were also susceptible to the ACA-PA even below their CMC.

Figure 5A:
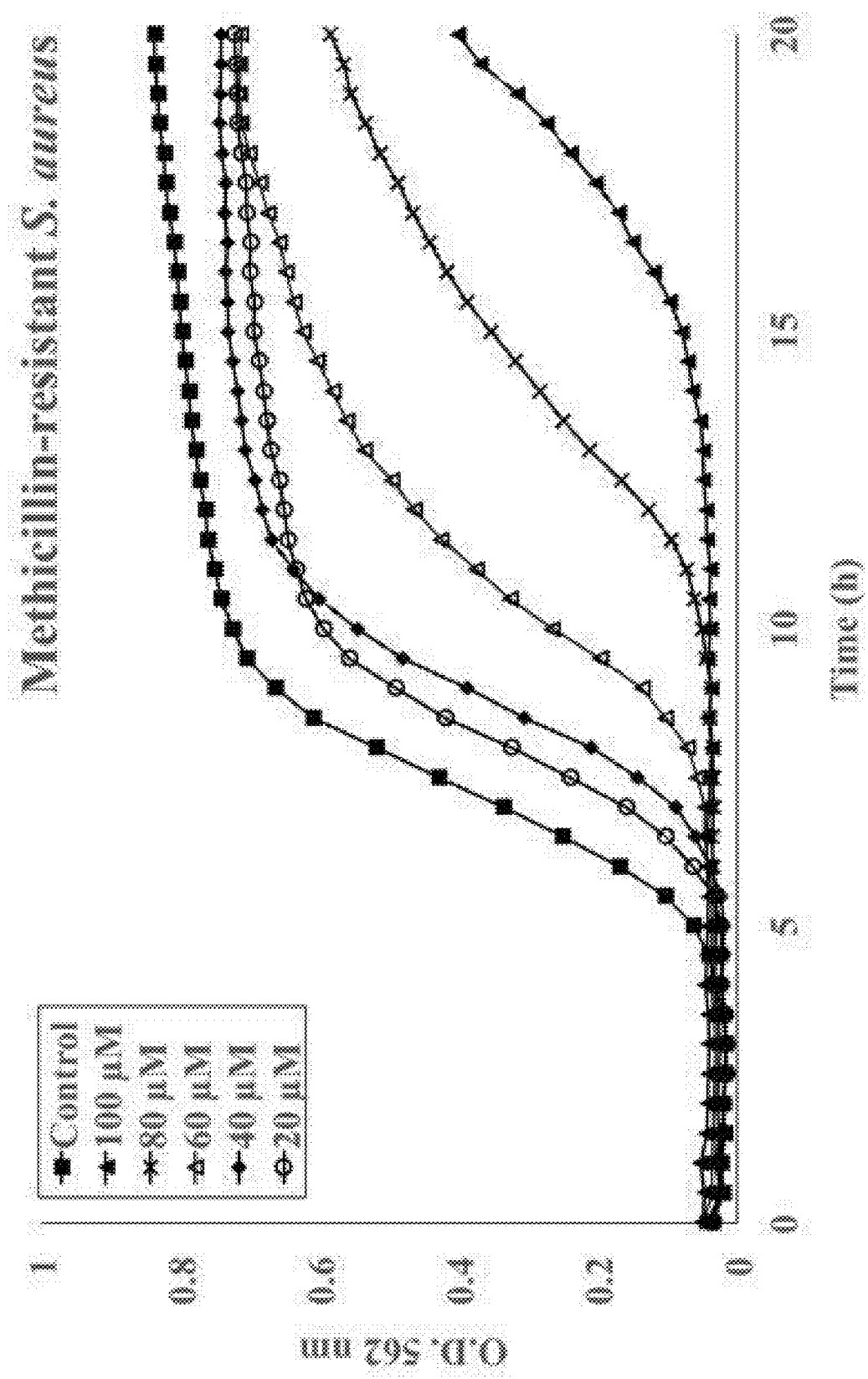
FIG. 5A depicts bacterial growth inhibition induced by an exemplary peptide, ACA-PA, against Gram-positive MRSA.
Figure 5B:
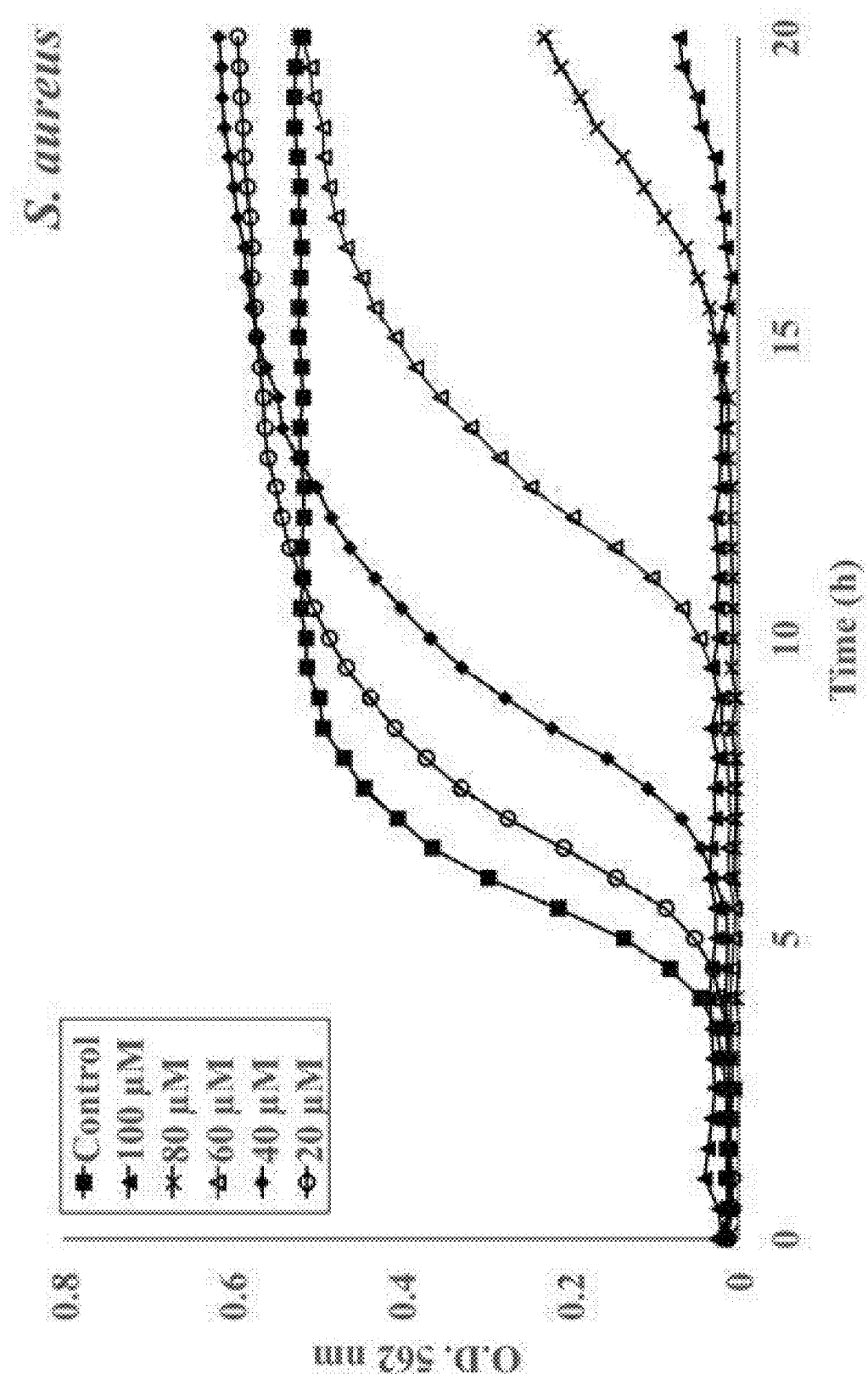
FIG. 5B depicts bacterial growth inhibition induced by an exemplary peptide, ACA-PA, against Gram-positive S. aureus.
Figure 5C:
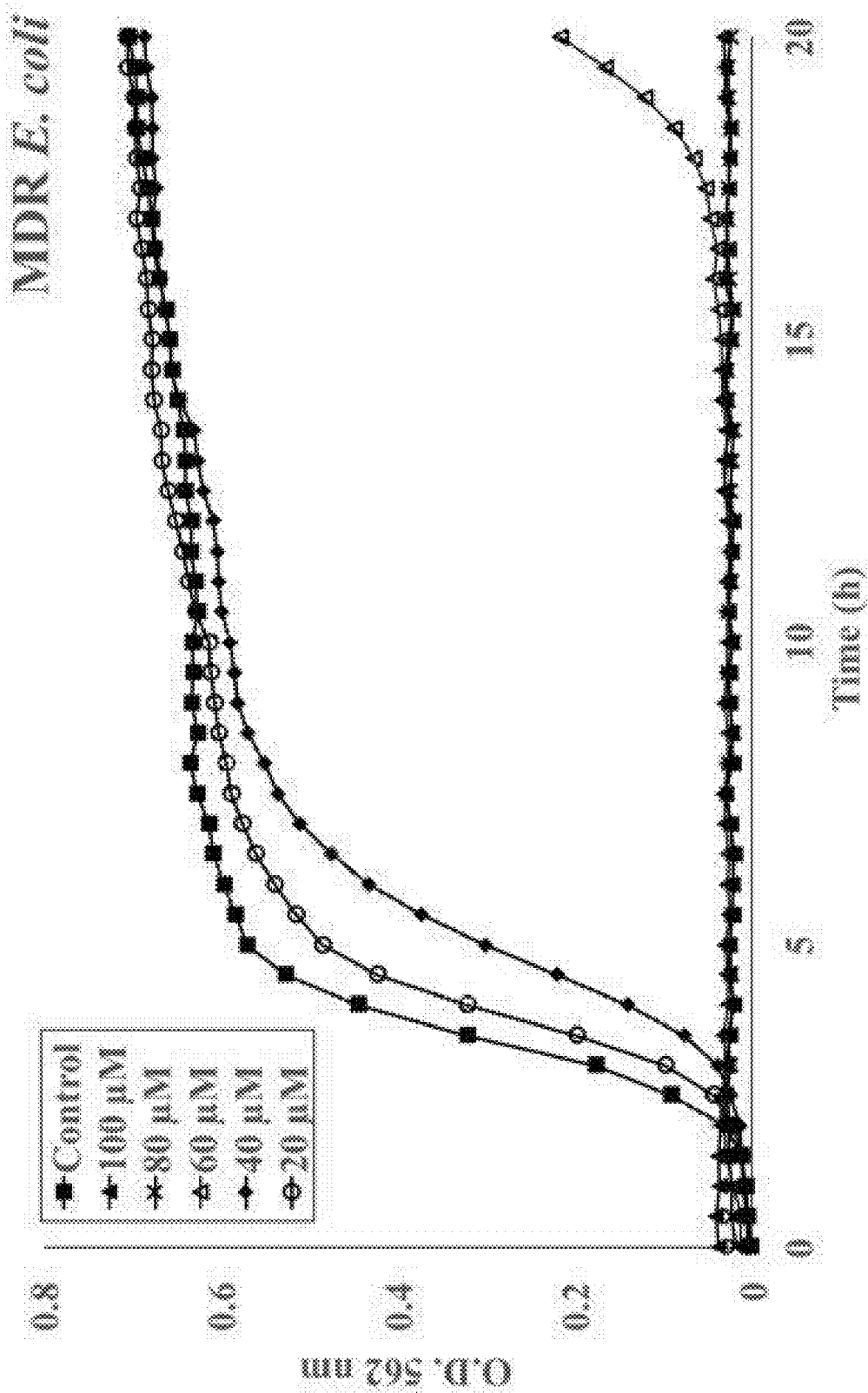
FIG. 5C depicts bacterial growth inhibition induced by an exemplary peptide, ACA-PA, against Gram-negative MDR E. coli.
Figure 5D:
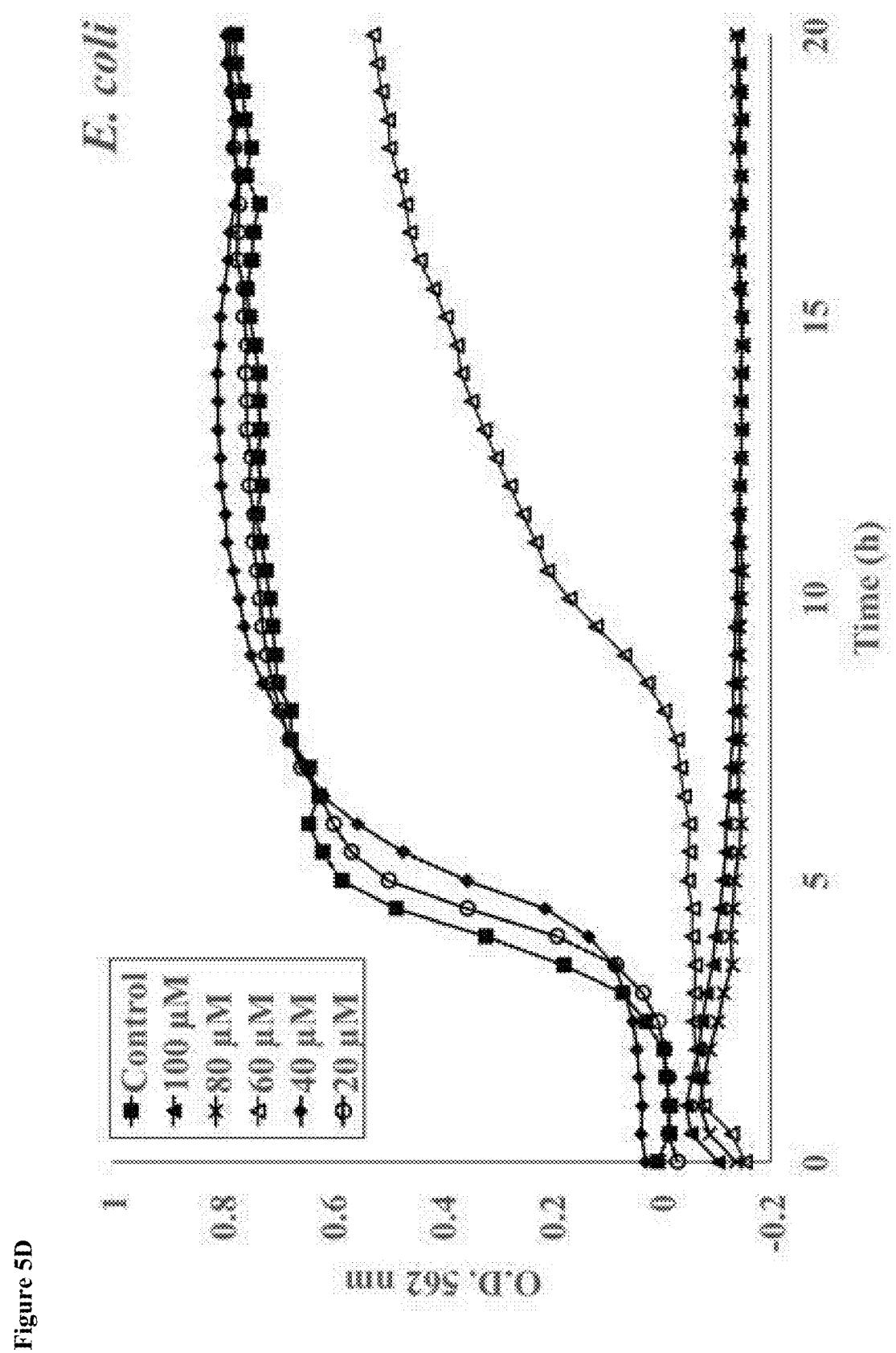
FIG. 5D depicts bacterial growth inhibition induced by an exemplary peptide, ACA-PA, against Gram-negative E. coli.
Figure 6A:
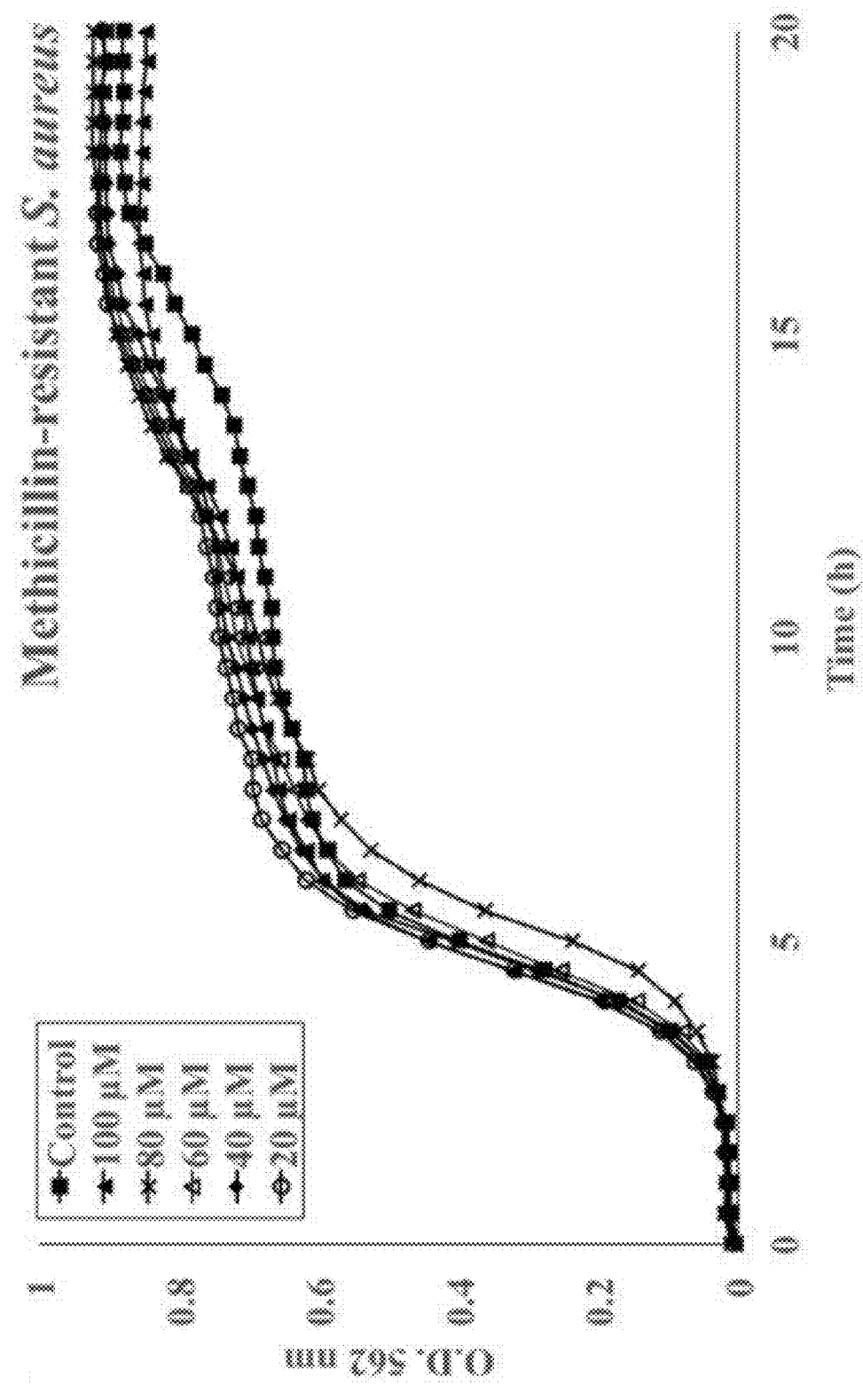
FIG. 6A depicts bacterial growth inhibition induced by Bi-Cardin against Gram-positive MRSA.
Figure 6B:
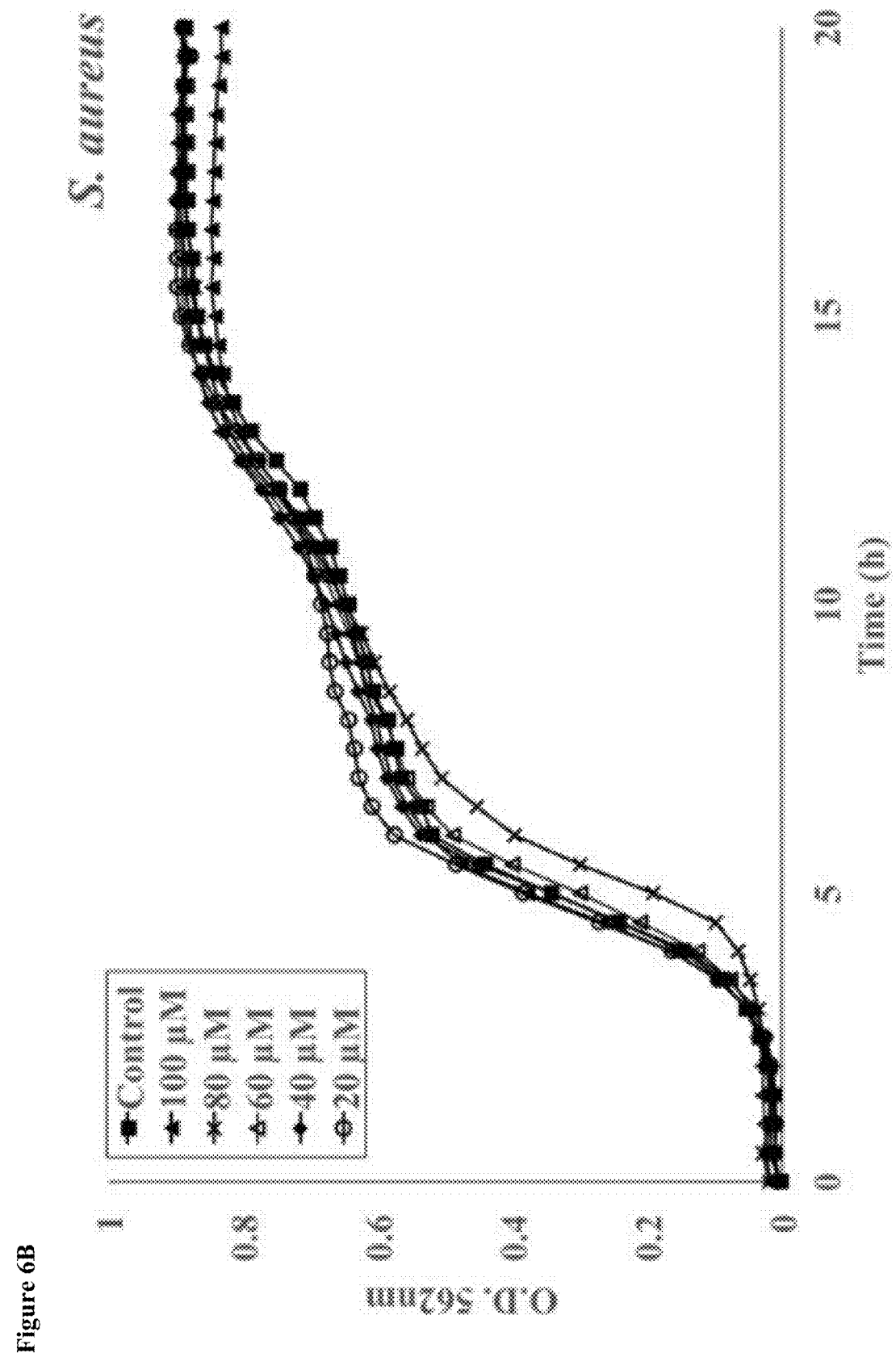
FIG. 6B depicts bacterial growth inhibition induced by Bi-Cardin against Gram-positive S. aureus.
Figure 6C:
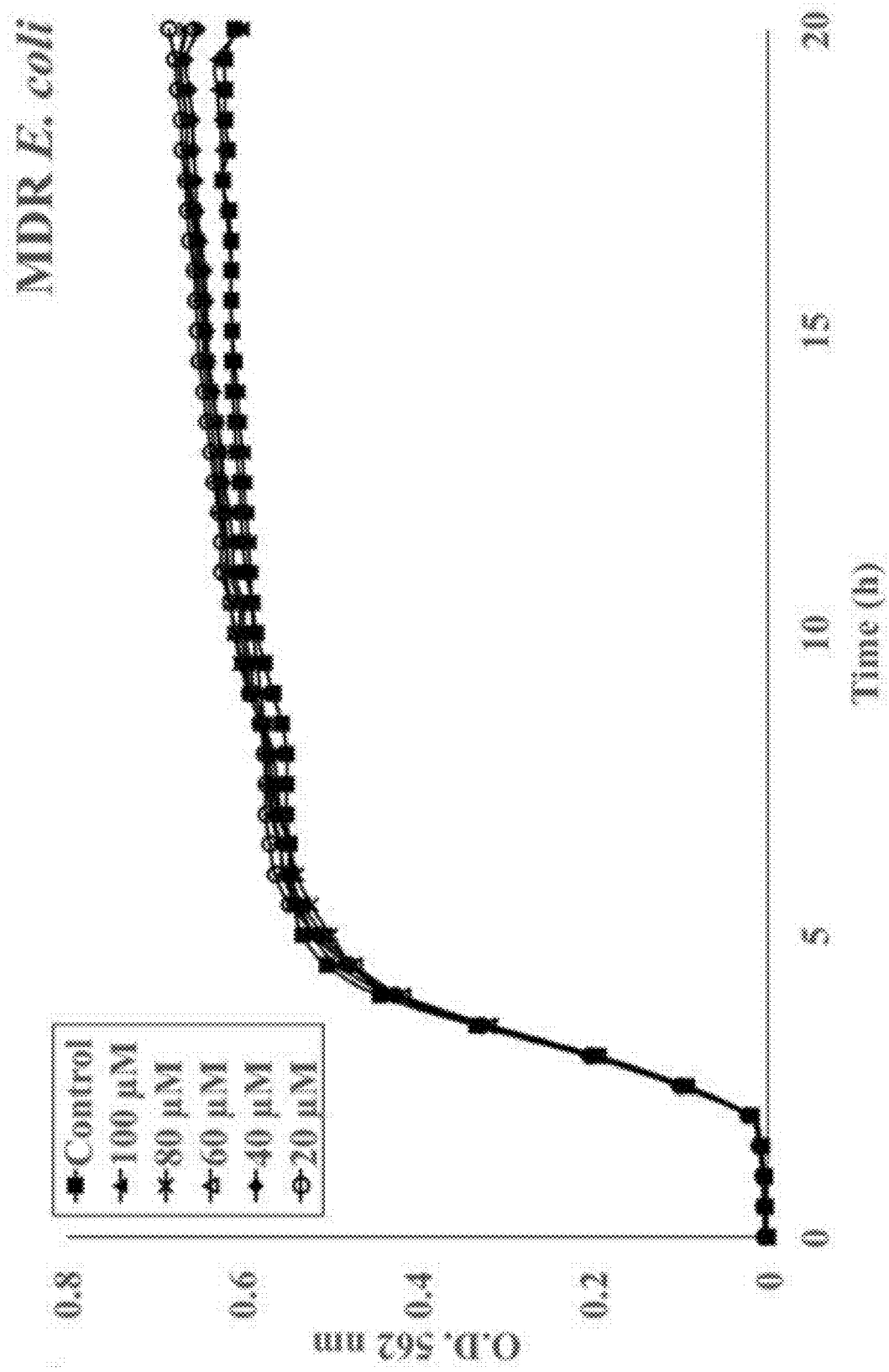
FIG. 6C depicts bacterial growth inhibition induced by Bi-Cardin against Gram-negative MDR E. coli.
Figure 6D:
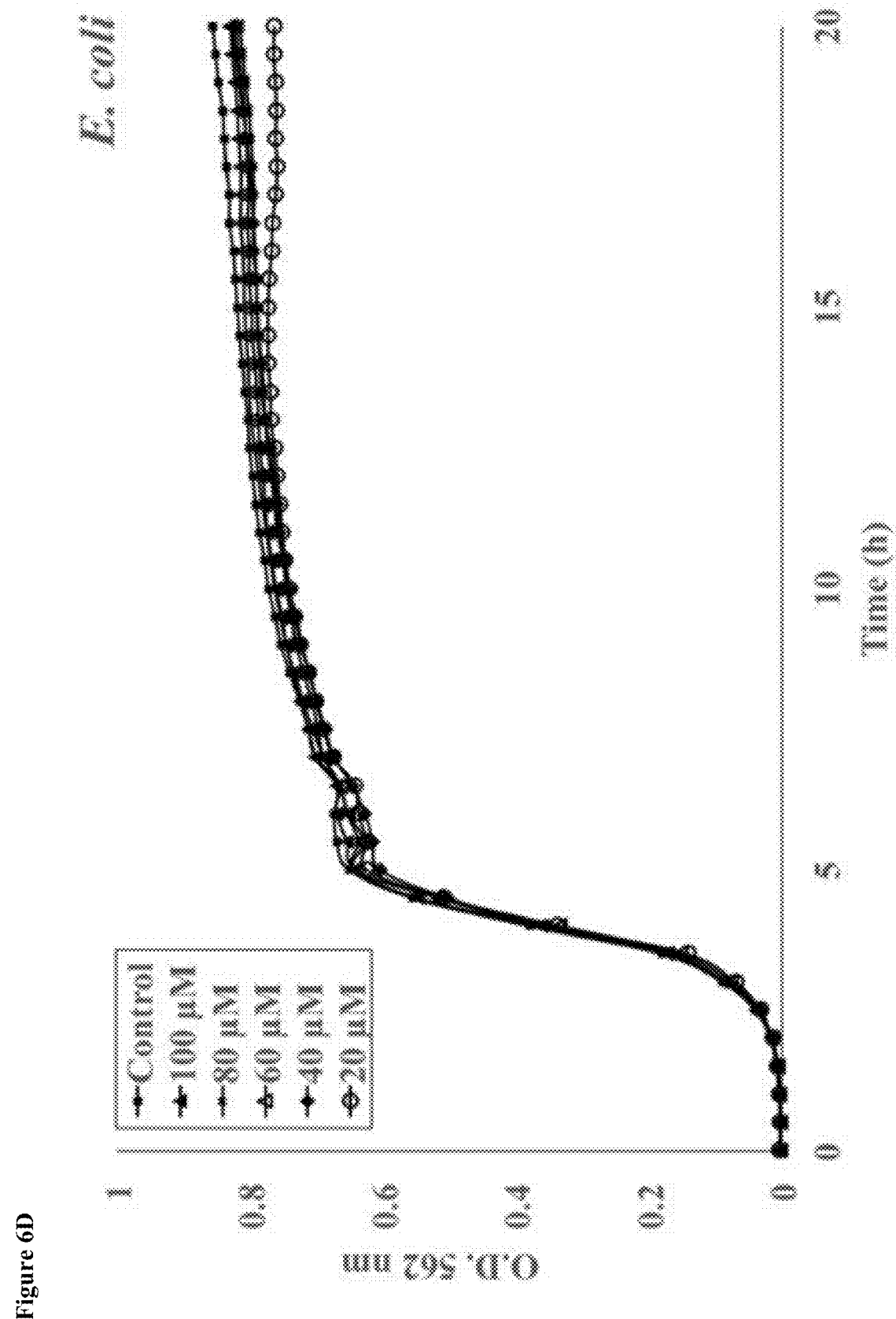
FIG. 6D depicts bacterial growth inhibition induced by Bi-Cardin against Gram-negative E. coli.
Figure 7A:
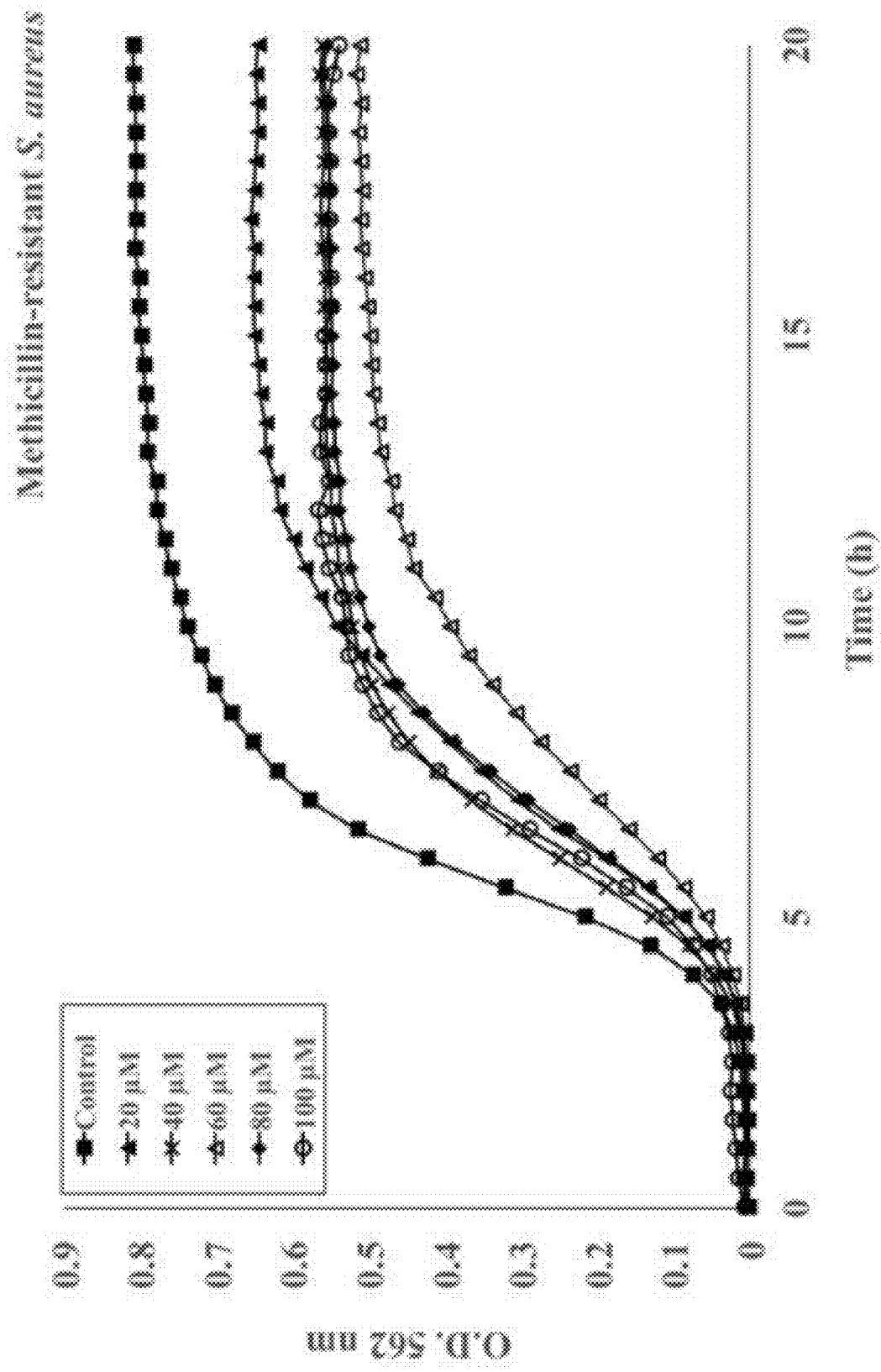
FIG. 7A depicts bacterial growth inhibition induced by a peptide, CVK-PA, against Gram-positive MRSA.
Figure 7B:
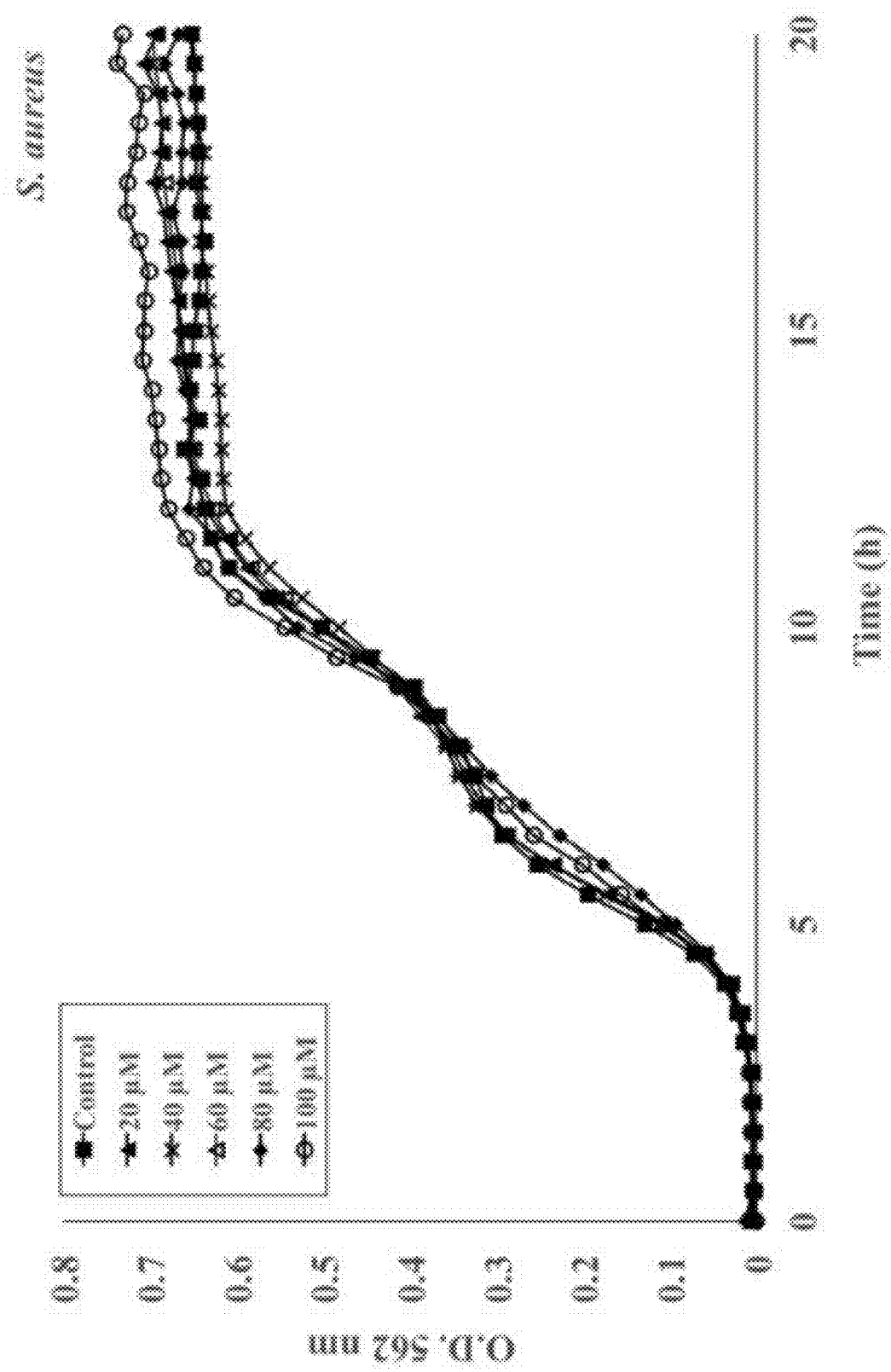
FIG. 7B depicts bacterial growth inhibition induced by a peptide, CVK-PA, against Gram-positive S. aureus.
Figure 7C:
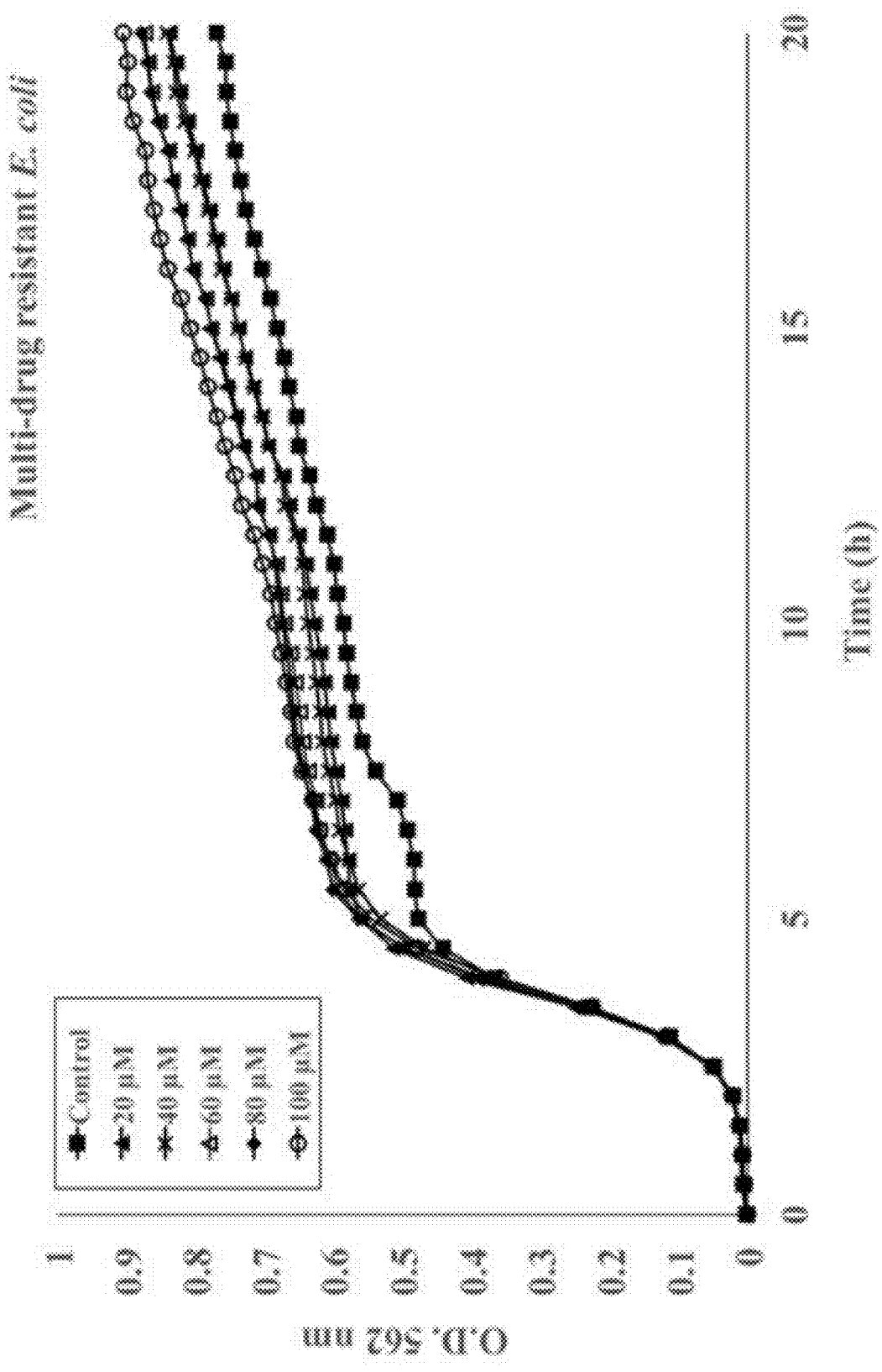
FIG. 7C depicts bacterial growth inhibition induced by a peptide, CVK-PA, against Gram-negative MDR E. coli.
Figure 7D:
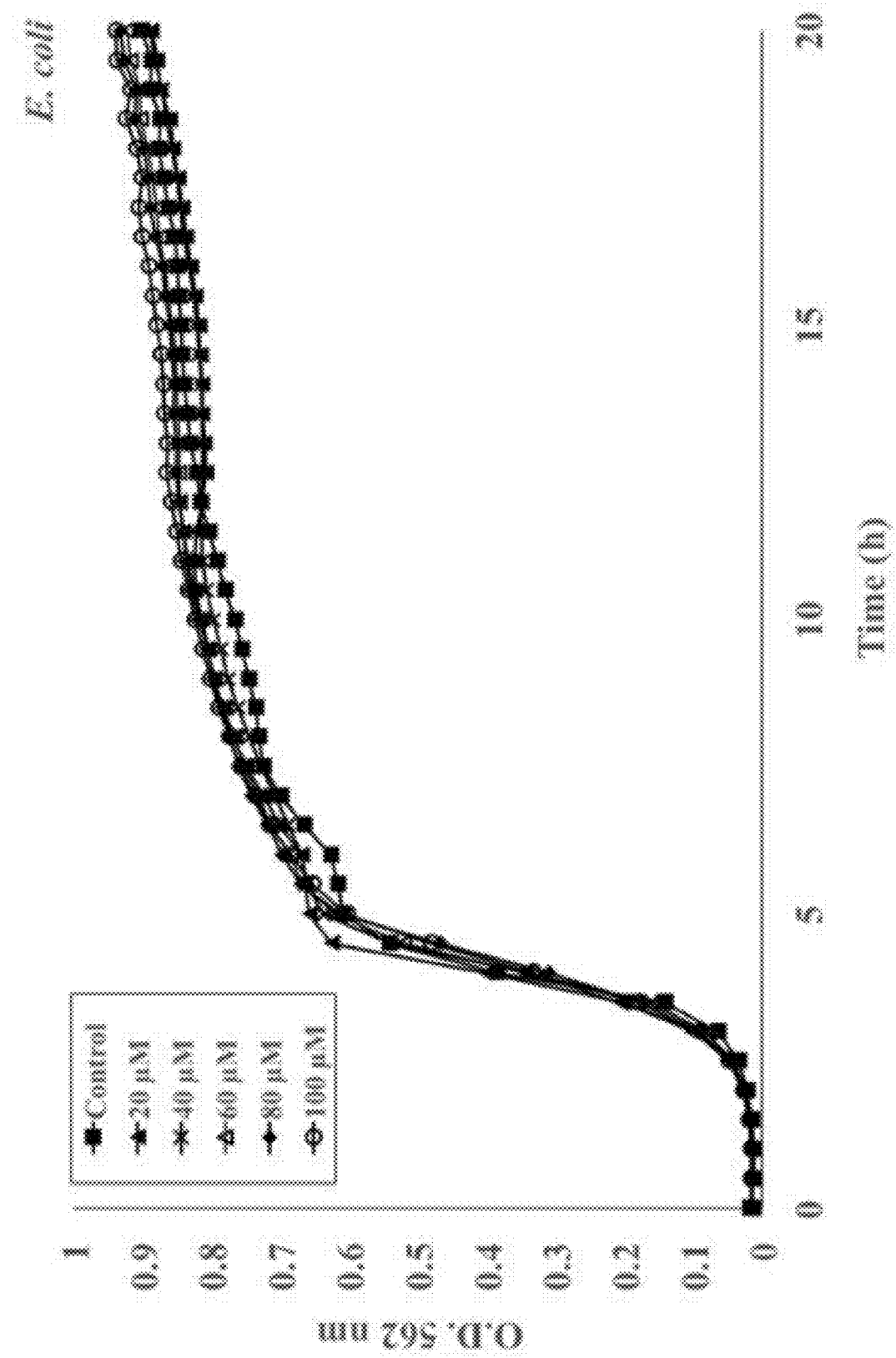
FIG. 7D depicts bacterial growth inhibition induced by a peptide, CVK-PA, against Gram-negative E. coli.

On the other hand, peptide self-assembly was shown to be critical factor for bacteria growth inhibition against Gram-negative *E. coli* and MDR *E. coli* bacteria. At concentrations higher than the CMC (60 µM to 100 µM), bacterial proliferation was significantly suppressed by the ACA-PA (FIGS. 5C and 5D). Specifically, no bacteria growth was observed for the MDR *E. coli* treated with ACA-PA over 80 µM, suggesting a bacteriostatic effect was induced by the self-assembled nanorods. As such, ACA-PA at concentrations lower than the CMC did not significantly inhibit bacterial growth. In addition, Bi-Cardin peptide was unable meaningfully to inhibit the proliferation of either Gram-positive or Gram-negative bacteria at any of the concentrations tested (FIGS. 6A-6D). CVK-PA peptide showed some inhibition of the proliferation of at least MRSA at the concentrations tested (FIGS. 7A-7D). The MIC values of ACA-PA towards drug-resistant bacteria were determined after 24 h of incubation (Table 2). The MIC results demonstrated that the antibacterial activities of ACA-PA were as effective as 78 U/mL and 625 U/mL of penicillin/streptomycin against MRSA and MDR *E. coli*, respectively.

TABLE 2

Minimum inhibitory concentration (MIC) values of ACA-PA to drug-resistant bacteria compared to penicillin-streptomycin (P/S).

| Bacterial Strain | P/S | ACA-PA |
| --- | --- | --- |
| MRSA | 78 U/mL | 300 µg/mL |
| MDR *E. coli* | 625 U/mL | 400 µg/mL |

ACA-PA achieved a significantly stronger antibacterial effect, as compared to CVK-PA with self-assembly backbone sequence and the non-self-assembling Bi-Cardin peptide. Without wishing to be bound by any theory, both heparin-binding groups and β-sheet forming self-assembly groups may be important to the antibacterial properties of the PA, which could be explained by the enhanced cationic charge, hydrophobicity and the formation of β-sheet structure of the ACA-PA. These physical and conformational characteristics of the amphiphilic peptide promote binding to the lipid acyl chains of the membrane and enhance membrane insertion [33]. Although the CVK-PA and Bi-Cardin peptide may interact with bacterial cell membranes via electrostatic interactions, the limited number of charged groups or hydrophobic residues may constrain their capability for membrane insertion.

Interestingly, the Gram-positive (*S. aureus* and MRSA) and Gram-negative (*E. coli* and MDR *E. coli*) strains responded differently to the ACA-PA treatment. Bacterial proliferation and the number of viable Gram-positive bacteria decreased proportionally to the increasing concentrations of ACA-PA. Even at concentrations below the CMC, the PA inhibited growth and promoted toxicity against the bacteria, which implied that the antibacterial property of the ACA-PA towards Gram-positive bacteria might not require peptide self-assembly. However, the results of bacterial studies towards Gram-negative bacteria indicated the low potency of ACA-PA at the concentrations lower than CMC. The dissociated PA had little antibacterial effect and, thus, peptide self-assembly was essential to kill Gram-negative bacteria. Once self-assembled, the ACA nanorods considerably suppressed Gram-negative bacterial growth and induced a remarkable reduction in cell viability.

This assay was performed to investigate the inhibitory effects of each peptide against Gram-positive *Staphylococcus aureus* (*S. aureus*, ATCC #25923) and methicillin-resistant *S. aureus* (MRSA, ATCC #43300), as well as Gram-negative *Escherichia coli* (*E. coli*, ATCC #25922), and multidrug-resistant *E. coli* (MDR *E. coli*, ATCC #BAA-2471). In all experiments, solutions of each peptide at the concentrations from 20 µM to 100 µM in 3% Tryptic Soy Broth (TSB) media were freshly prepared. A single colony of bacteria was isolated from a stock agar plate and cultured overnight in 4 mL of 3% TSB on a shaking incubator set at 200 rpm and 37° C. The bacteria culture was adjusted to an optical density at 562 nm ($OD_{562}$) to about 0.52 ($10^9$ cells/mL), and the resulting bacteria suspension was subsequently diluted to about $10^6$ colony forming units (CFU) per mL in each sample. The control samples were bacteria incubated in TSB media without peptides. The bacteria were incubated inside a spectrophotometer (Spectra-Max Paradigm, Molecular Devices, Sunnyvale, CA) at 37° C. under static conditions for 20 h, and the bacterial growth curves were measured in terms of turbidity at $OD_{562}$ every 2 minutes [24]. The normalized $OD_{562}$ values of samples were calculated by subtracting the experimental $OD_{562}$ values from the corresponding blank samples without bacteria.

The minimum inhibitory concentration (MIC) of ACA-PA was tested against drug-resistant bacteria and compared with conventional penicillin-streptomycin (10,000 U/mL, Thermo Fisher Scientific, Waltham, MA, USA) as well. Solutions of each antimicrobial agent at different concentrations were prepared by serial 2-fold dilutions in water. Bacteria (seeding density=$10^6$ CFU/mL) were then mixed with the antimicrobial solutions, and incubated for 24 h at 37° C. The $OD_{562}$ was measured at the end of treatment. The MIC value was determined as the lowest concentration of each antimicrobial agent that induced no increase in $OD_{562}$. All experiments were run in triplicate to demonstrate significance. Data are expressed as mean±standard error of the mean (S.E.M.) and a two-tailed Student t-test was used to evaluate differences between means, with $p<0.005$ being considered statistically significant.

Example 6: Evaluation of Bactericidal Property

Figure 8A:
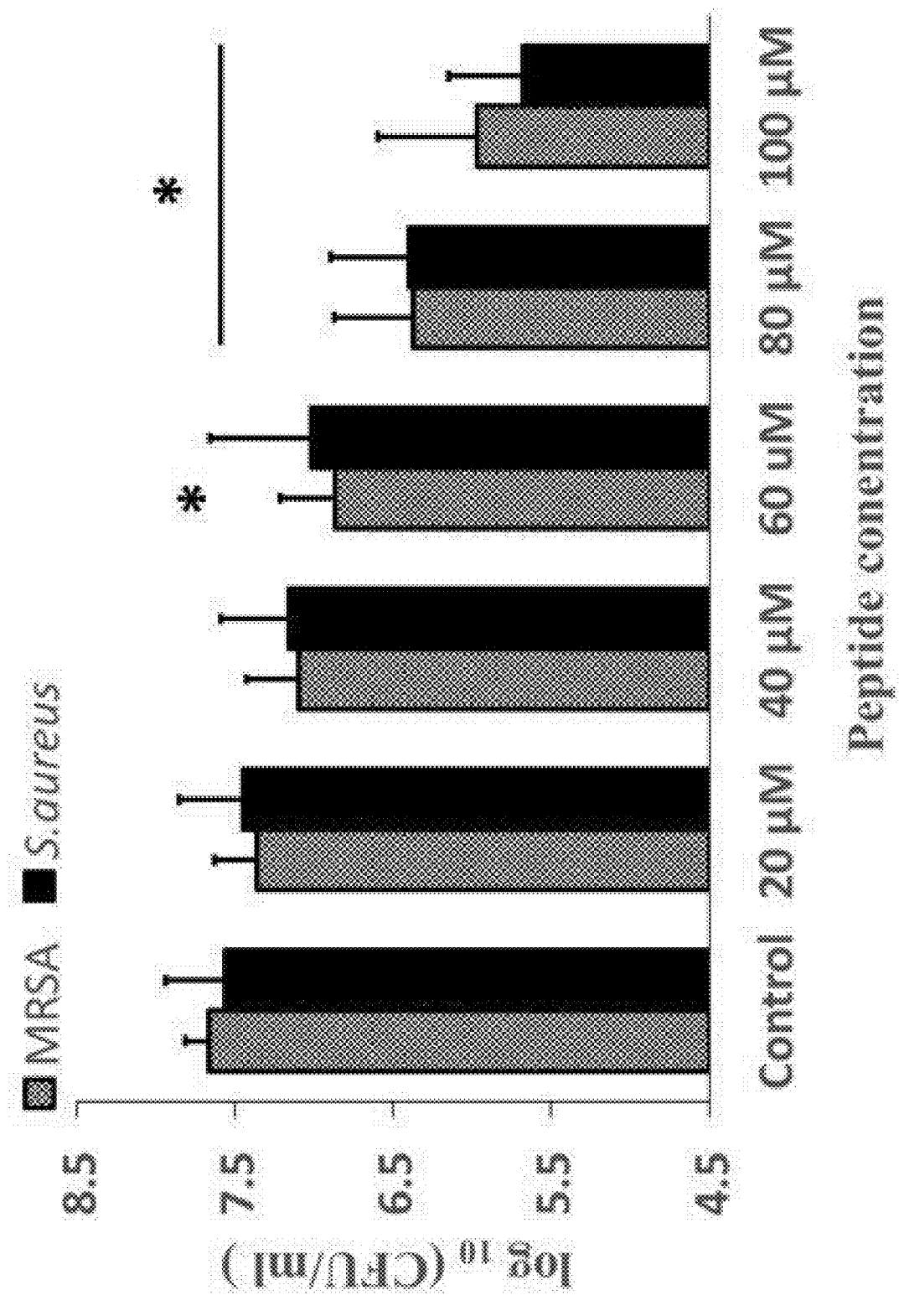
FIG. 8A depicts the bactericidal effect of an exemplary peptide, ACA-PA, against Gram-positive bacteria.
Figure 8B:
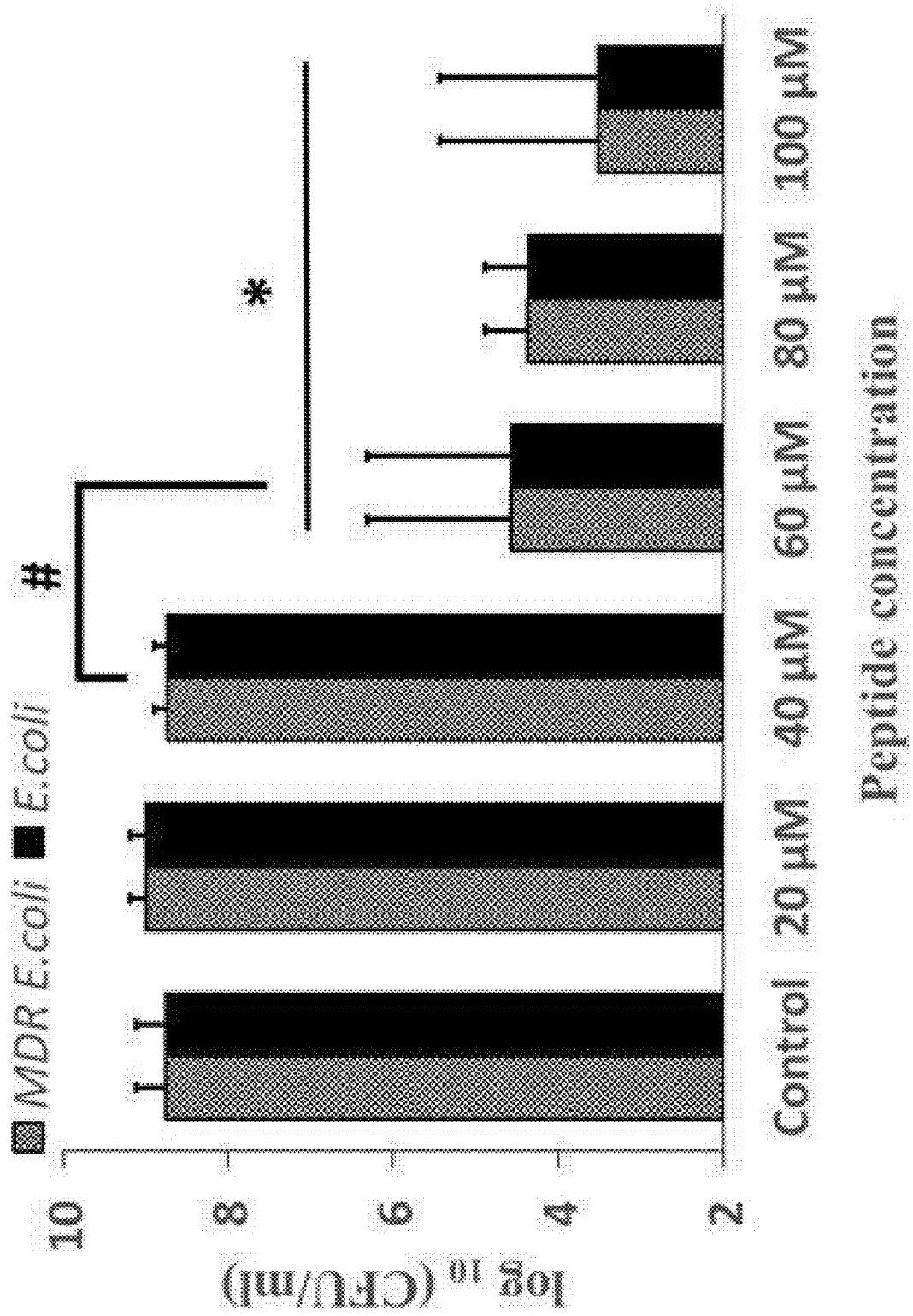
FIG. 8B depicts the bactericidal effect of an exemplary peptide, ACA-PA, against Gram-negative bacteria.

The bactericidal effects of the peptides were examined using a viable colony count assay as well as the live/dead staining assay. For the viable colony count assay, bacteria were treated with peptides for 4 h and the resulting viable bacterial density of each sample was expressed by $\log_{10}$ [CFU/mL]. For the Gram-positive bacteria tested, the decrease in bacterial density was dependent on the concentration of the ACA-PA (FIG. 8A). At concentrations over 80 µM, the ACA nanorods possessed significant bacteria toxicity which decreased colony forming units for both *S. aureus* and MRSA by two logs, which suggested a 100-fold decline in bacteria density. As for Gram-negative *E. coli* and MDR *E. coli* bacteria (FIG. 8B), the ACA nanorods, wherein the PA were added at a concentration above their CMC, had potent bactericidal effects. For example, the ACA nanorods at concentrations over 60 µM reduced the colony forming units of Gram-negative bacteria by about a five log unit reduction after 4 h compared with the untreated negative control sample. However, no significant reduction in Gram-negative bacteria density was observed in the samples treated with ACA-PA at concentrations lower than CMC. These results indicated that the self-assembly of the ACA nanorods enhanced the antibacterial activity against Gram-negative bacteria. Additionally, CVK-PA and Bi-Cardin peptide showed no bactericidal effects towards Gram-positive or Gram-negative bacteria in comparison to the ACA-PA. These results were consistent with the observations from the growth curves of the bacteria treated with PA.

Figure 9A:
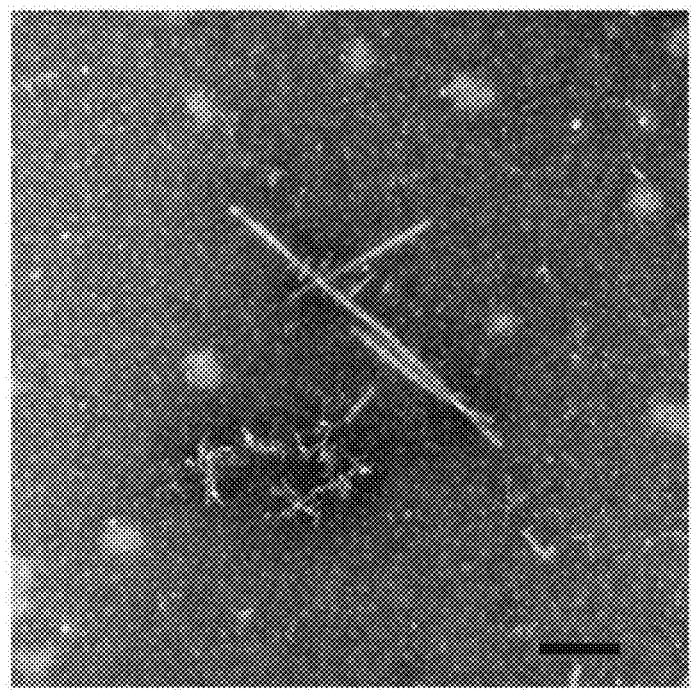
FIG. 9A depicts a TEM image of the self-assembled morphology of an exemplary peptide, ACA-PA, after mixing with heparin.
Figure 9B:
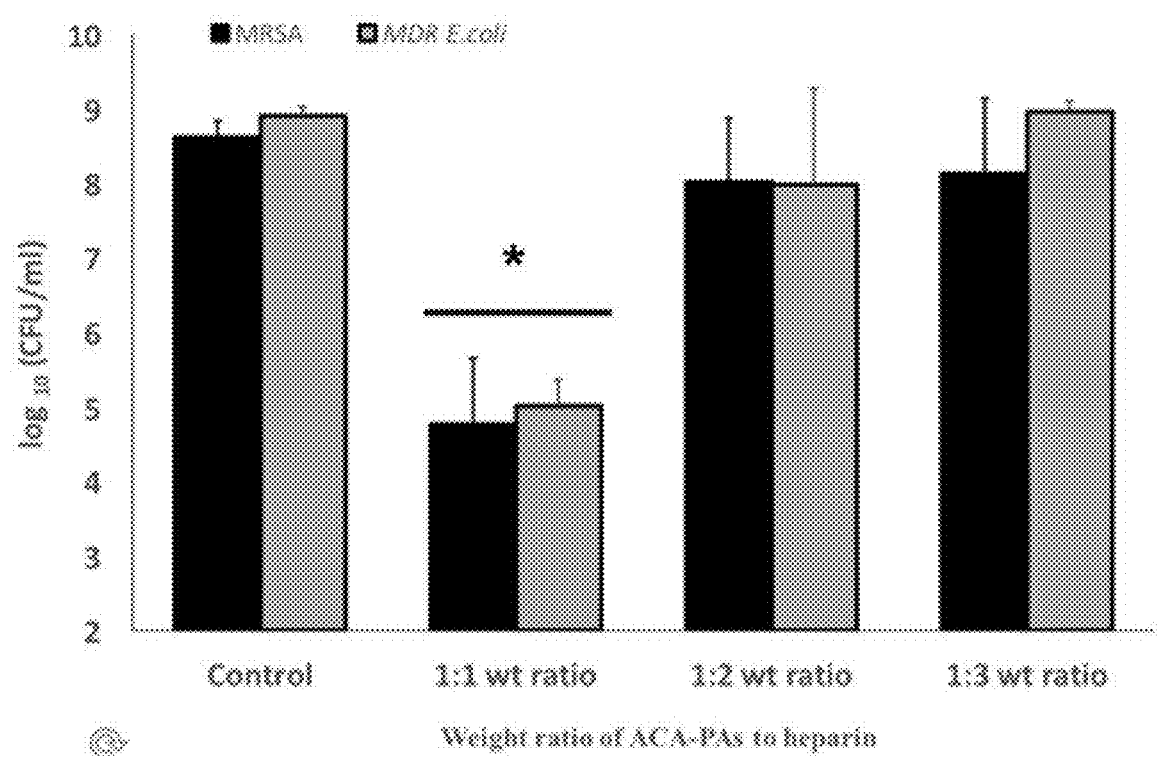
FIG. 9B depicts the bactericidal effect of an exemplary peptide, ACA-PA, against drug-resistant bacteria after mixing with heparin in various weight ratios.

In addition, ACA-PA were mixed with heparin at various weight ratios (1:1, 1:2, and 1:3 ACA-PA to heparin ratios) to block the Cardin motif groups on the PA. The ACA-PA concentration used to treat bacteria (MRSA and MDR $E.$ $coli$) was a constant 80 μM and only varied in the concentration of heparin. The results indicated that the number of viable bacteria colonies were positively proportional to the amount of heparin added to the ACA-PA, although the self-assembled structure of the ACA nanorods was not affected by the addition of heparin (FIGS. 9A and 9B). The ACA nanorods could be saturated at the 1:3 ACA-PA to heparin weight ratio as no toxicity towards bacteria was observed. Without wishing to be bound by any theory, these results suggested that the heparin-binding cationic Cardin-motifs participated in the antibacterial activity of the ACA nanorods.

The viable count assay was performed to quantify the bactericidal activity of each peptide [25]. Stock solutions of peptides were diluted in 3% TSB media to concentrations ranging from 20 μM to 100 μM immediately before experiments. Heparin-ACA-PA were also prepared by mixing the ACA-PA stock solution with heparin (sodium salt from porcine intestinal mucosa, Sigma, St. Louis, MO) to 1:1, 1:2 and 1:3 weight ratios in water, and a final concentration of ACA-PA in the heparin-ACA-PA at each heparin weight ratio was adjusted to 80 μM for each experiment. The bacteria ($10^6$ CFU/mL) were incubated with peptides at 37° C. for 4 h. After incubation, serial dilutions of samples were plated on TSB agar and then incubated at 37° C. overnight. The colonies from each spot were manually counted, and the CFU number for each sample was determined. Experiments were conducted in triplicate and results were expressed as the log 10 values of the CFU number in each sample. Data were expressed by stand error of the mean (±S.E.M.) and N=3, *$p<0.05$ compared with control samples and #$p<0.05$ compared with bacteria treated with 40 μM of ACA-PA.

Figure 10A:
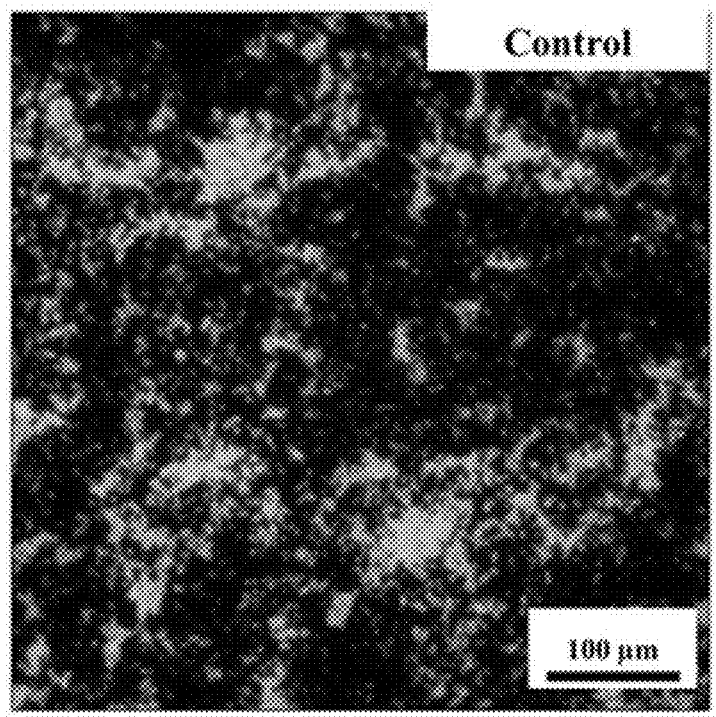
FIG. 10A depicts bacterial viability using a live/dead assay for untreated Gram-positive MRSA.
Figure 10B:
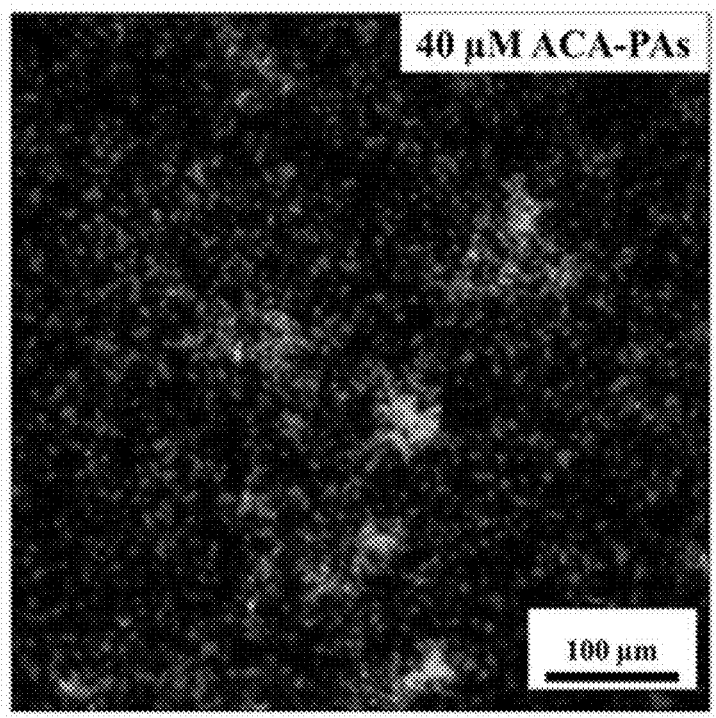
FIG. 10B depicts bacterial viability using a live/dead assay for Gram-positive MRSA with 40 μM of an exemplary peptide, ACA-PA.
Figure 10C:
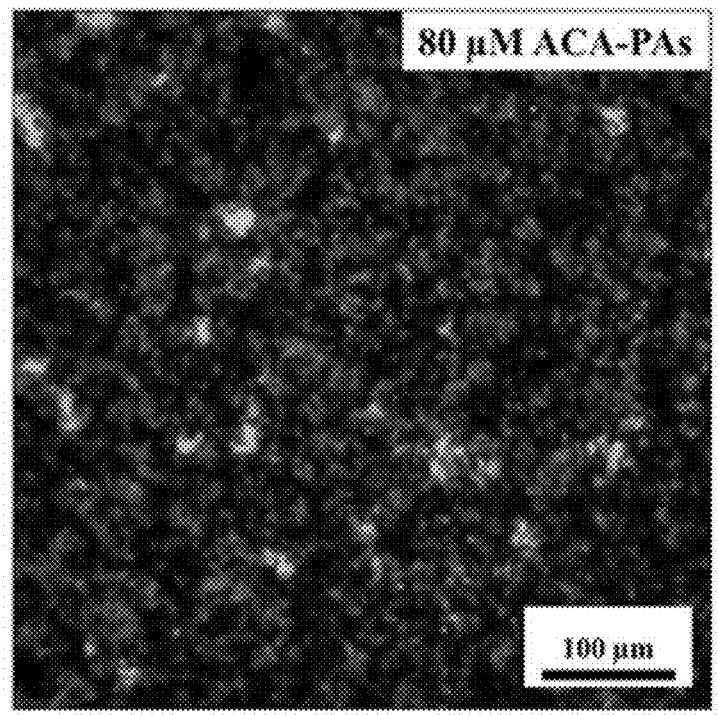
FIG. 10C depicts bacterial viability using a live/dead assay for Gram-positive MRSA with 80 μM of an exemplary peptide, ACA-PA.
Figure 10D:
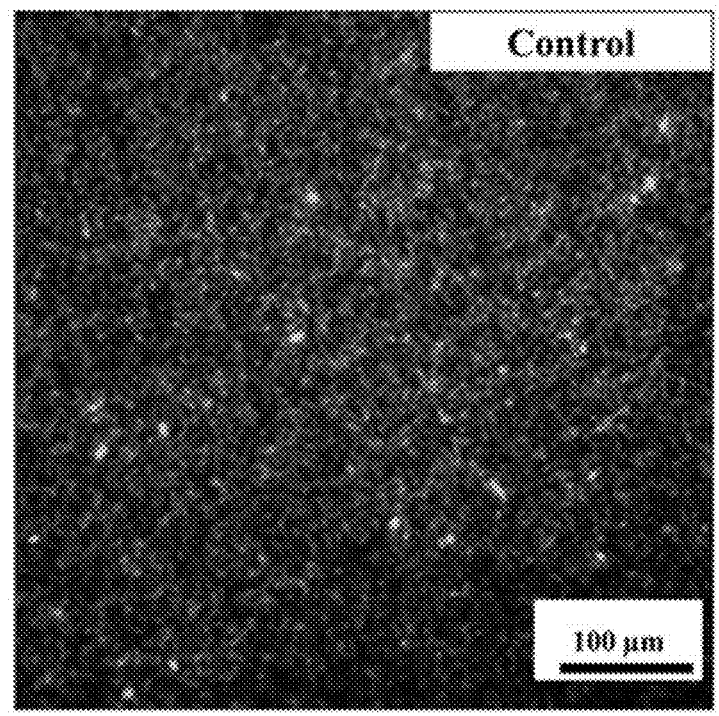
FIG. 10D depicts bacterial viability using a live/dead assay for untreated Gram-negative MDR E. coli.
Figure 10E:
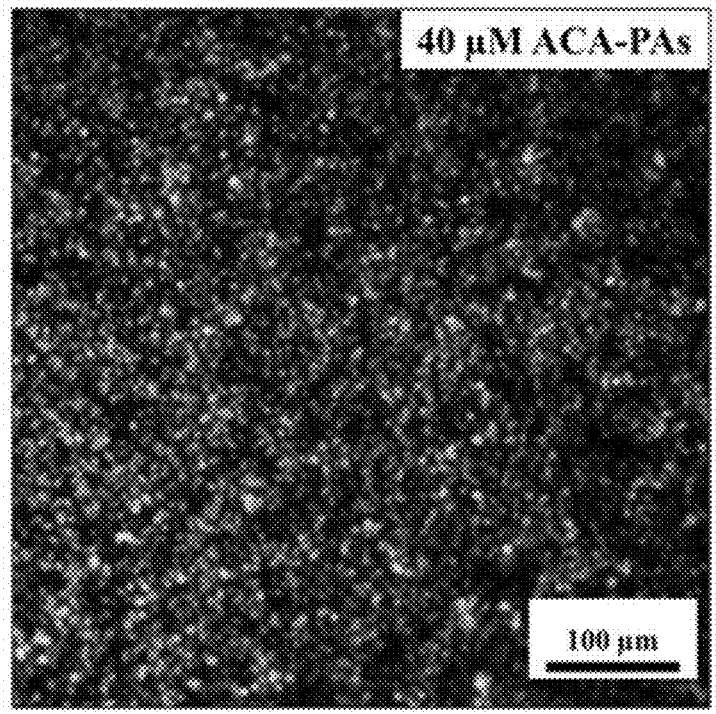
FIG. 10E depicts bacterial viability using a live/dead assay for Gram-negative MDR E. coli with 40 μM of an exemplary peptide, ACA-PA.
Figure 10F:
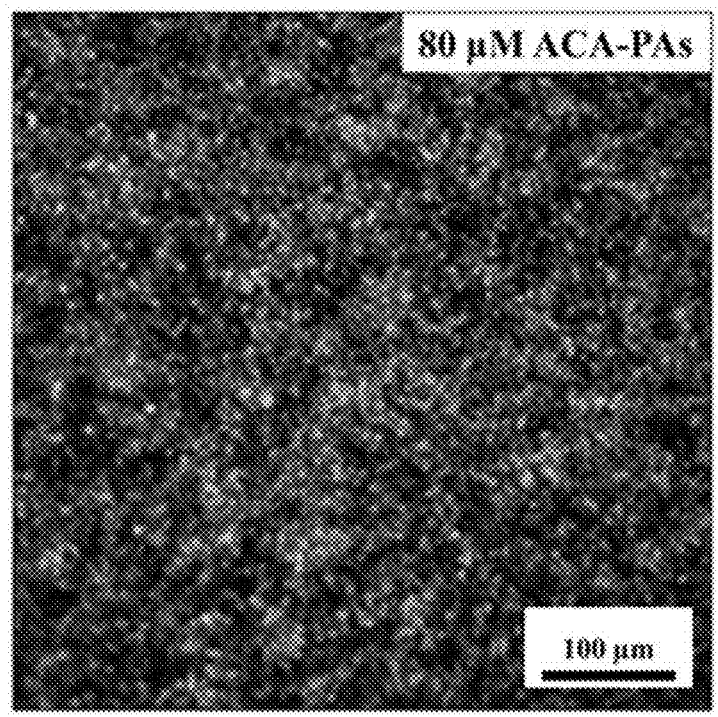
FIG. 10F depicts bacterial viability using a live/dead assay for Gram-negative MDR E. coli with 80 μM of an exemplary peptide, ACA-PA.

To further investigate bacteria viability after treatment with ACA-PA, the live/dead assay was used to confirm the antibacterial actions of ACA-PA. Dead bacteria with disrupted membrane were stained a first color, whereas live bacteria were stained with a second color fluorescence. A large amount of robust MRSA bacteria in the untreated control sample appeared a second color and in spherical shapes (FIG. 10A). Followed by treatment with 40 μM of ACA-PA for 4 h, the increase in a first color fluorescent spots and decreased number of second color fluorescent stained cells suggested markedly reduced MRSA viability (FIG. 10B). Interestingly, dead bacteria in a first color fluorescence tended to aggregate into bacterial clusters, which might result from the aggregation of de-stabilized bacterial cell membranes [25]. Furthermore, the coverage of dead bacteria increased with low density of live bacteria after being treated with 80 μM of ACA-PA (FIG. 10C). These results further confirmed that ACA-PA were capable of inducing Gram-positive bacterial cell death below their CMC. This antibacterial activity was dependent on the concentration of PA, yet was not determined by peptide self-assembly. Nonetheless, Gram-negative MDR $E.$ $coli$ responded to the treatment of ACA-PA differently from Gram-positive MRSA. The control MDR $E.$ $coli$ had a rod-shaped morphology (FIG. 10D). The treatment with 40 μM of ACA-PA was unable to induce considerable cell mortality (FIG. 10E). Above the CMC at 80 μM, the self-assembled ACA-PA enhanced the number of dead bacteria drastically (FIG. 10F), indicating a prominent improvement in the antibacterial property of the PA against Gram-negative bacteria upon peptide self-assembly.

The live/dead bacterial viability assay was conducted to further assess the bactericidal efficacy of ACA-PA using the LIVE/DEAD BacLight Bacterial Viability Kits (Kits 71007, Molecular Probes, Eugene, OR, USA). MRSA and MDR $E.$ $coli$ bacteria (100 μl, $10^6$ CFU/mL) were incubated with 80 μM and 40 μM of peptide in 3% TSB media at 37° C. for 4 h on a 96-well plate, and the control samples of bacteria were incubated in 3% TSB media only. At the end of treatment, the supernatant of each sample was carefully removed, and the bacteria on the bottom of the 96-well plate were stained with reagent solution that was prepared according to the manufacturer's instructions, and incubated at room temperature for 10 minutes Samples were observed in a fluorescent microscope using Alexa Fluor 488 (emission/excitation wavelength=500/519 nm) and PI (excitation emission=490/635 nm) filter sets. The live bacteria stained fluorescent a second color (SYTO9 nucleic acid stain), whereas the dead bacteria with disrupted membranes stained fluorescent a first color (propidium iodide, PI).

Example 7: Lipopolysaccharides (LPS) Binding Assay

Figure 11:
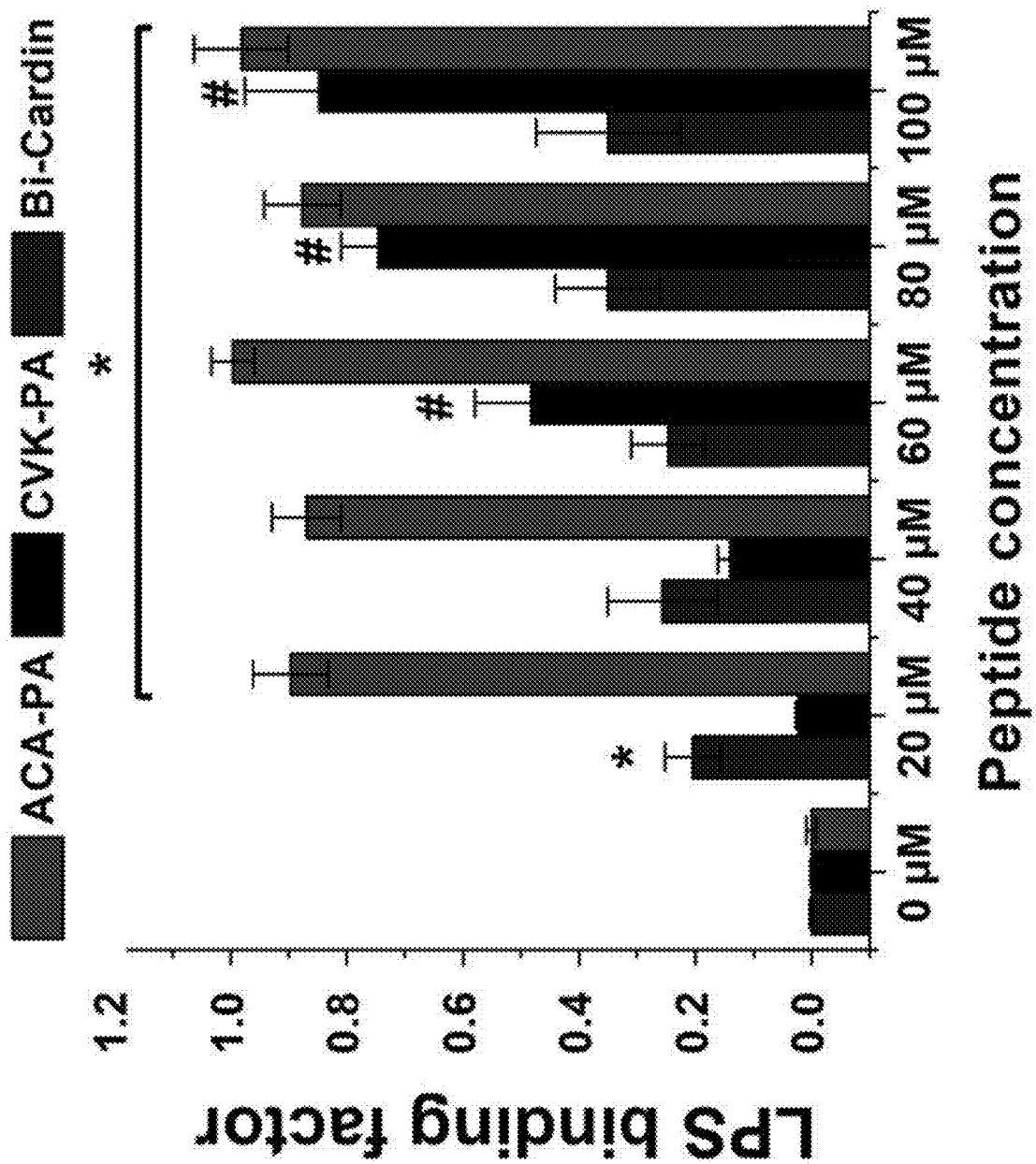
FIG. 11 depicts determination of LPS binding affinities of peptides using BC probe displacement assay.

The binding of each peptide at various concentrations to LPS was determined by the capability of displacing the BC probes bound with LPS. The fluorescent BC probe was used as a probe to determine the level of peptide bound with LPS. BC probe binds to native LPS and particularly target the lipid A portion. The fluorescent intensity of BC probe decreases as it binds to LPS. Nonetheless, once the cationic peptides that that have competitively stronger interactions with LPS, BC probes on LPS are displaced and thus exhibit fluorescent enhancement [26, 27]. As FIG. 11 reveals, all the peptides were able to replace the BC probe and caused enhanced fluorescent intensity of the probe compared to samples without peptides, which demonstrated their interactions with the negatively charged LPS. Moreover, the peptides displayed different binding activities with LPS. The LPS binding factor of Bi-Cardin peptide remained in similar levels and was irrespective of the increasing peptide concentration. The CVK-PA showed weak binding affinity to LPS at concentrations from 20 μM to 40 μM, but introduced significantly enhanced binding affinity at concentrations higher than CMC. For instance, the LPS binding factor of samples containing 60 μM of CVK-PA was as double as the 40 μM sample. The result indicated that self-assembly of CVK-PA at concentrations over its CMC can improve its interactions with LPS. Furthermore, the ACA-PA exhibited the highest LPS binding capability among the peptides investigated at all the concentrations. Nonetheless, no statistically significant difference was observed between peptide concentrations below and higher than CMC, suggesting the strong interactions of ACA-PA may be irrelative to peptide self-assembly.

LPS is one of the major components in the outer membrane of most Gram-negative bacteria, which is considered the extra protection to bacteria. The core region of LPS can protect the organism from hydrophobic antibiotics, whereas the mutations in porins can decrease the entry of hydrophilic antimicrobial compounds and result in drug resistance. Thus, antibacterial agents that can penetrate and destabilize LPS barrier can possibly inhibit resistance of bacteria [35]. To further investigate the interactions with LPS and mechanisms of antibacterial actions towards Gram-negative bacteria, LPS binding affinity of each peptide was analyzed in this study. The results showed that both Bi-Cardin peptide and CVK-PA can associate with LPS, although these two peptides had low antibacterial activities as observed in the bacterial studies. Interestingly, the binding affinity of CVK-PA to LPS dramatically enhanced when it self-assembled into supramolecular nanofibers beyond the CMC at about 50 µM. These findings suggest that self-assembly of peptide amphiphiles monomers into highly organized nanostructures can play a crucial role in association with LPS layer in bacteria, and also indicate the potential applications of incorporating self-assembling properties in peptide-based antibiotics for improved LPS destabilization. In addition, the ACA-PA exhibited the most effective LPS binding actions over all the concentrations investigated, which may result from the electrostatic interactions of the positively charged peptide with anionic LPS. Since the ACA-PA showed to have high LPS binding affinity even at concentrations lower than CMC, the electrostatic interactions of the peptide seemed to dominate over the effects of peptide self-assembly on LPS binding. This can be explained by the "self-promoted uptake pathway" in the interactions of bacterial LPS with cationic peptides. Peptides with strong affinities to LPS can competitively displace divalent cations (i.e. $Ca^{2+}$ and $Mg^{2+}$), resulting in disruption in the outer membrane. The antimicrobial peptides can further perpetrate into the cytoplasm membrane as the damaged outer membrane passively internalizes more molecules from the exterior [3, 36]. In summary, we have found that the potent antibacterial properties of ACA-PA against Gram-negative bacteria can be ascribed to its strong LPS binding affinity, and the peptide self-assembly as well as the positive charge may participate in the interactions with LPS.

The LPS binding affinity of peptide was examined with the BODIPY TR cadaverine (BC) fluorescent probe displacement assay as previously described [26, 27]. Stock solution of each peptide was diluted to predetermined concentrations with 10 mM HEPES buffer (pH=7.5, Thermo Fisher Scientific, Waltham, MA, USA). Peptide solutions were equilibrated for 10 minutes, and LPS (from *Escherichia coli* O111:B4, Sigma, St. Louis, MO, USA) solution in 10 mM HEPES buffer was added. The final peptide concentrations ranged from 20 µM to 100 µM, and the LPS concentration was 100 µg/mL. LPS only samples were solutions that only contained the same amount of LPS without peptide. Peptides were allowed to interact with LPS in room temperature for 15 minutes, and the BC probe solution in 10 mM HEPES buffer was added to achieve a final concentration of 10 µM. Followed by incubation for 15 minutes in room temperature, the fluorescent intensity was measured using a spectrophotometer at an excitation wavelength of 580 nm and an emission wavelength of 620 nm. Finally, the LPS binding factor of each sample was calculated using the equation:

$$LPS \text{ binding factor} = 1 - \frac{Fp - Fp, LPS}{Fp - FLPS}$$

where Fp is the fluorescent intensity of BC probe in each peptide solution, Fp,LPS is the fluorescent intensity of BC probe in the mixture of peptide/LPS solution, FLPS represents the fluorescent intensity of BC probe in solution containing LPS only.

When peptides bind to LPS and displace the BC probe, fluorescence intensity of the probe is increased. LPS binding affinity of each peptide was then analyzed by the fluorescent intensity of the displaced BC probe. Data were expressed by stand error of the mean (±S.E.M.) and N=3, *p<0.05 compared with 0 µM samples and #p<0.05 compared with 40 µM samples of the same peptide.

Example 8: Analysis of Bacterial Membrane Disruption Using TEM

Figure 12A:
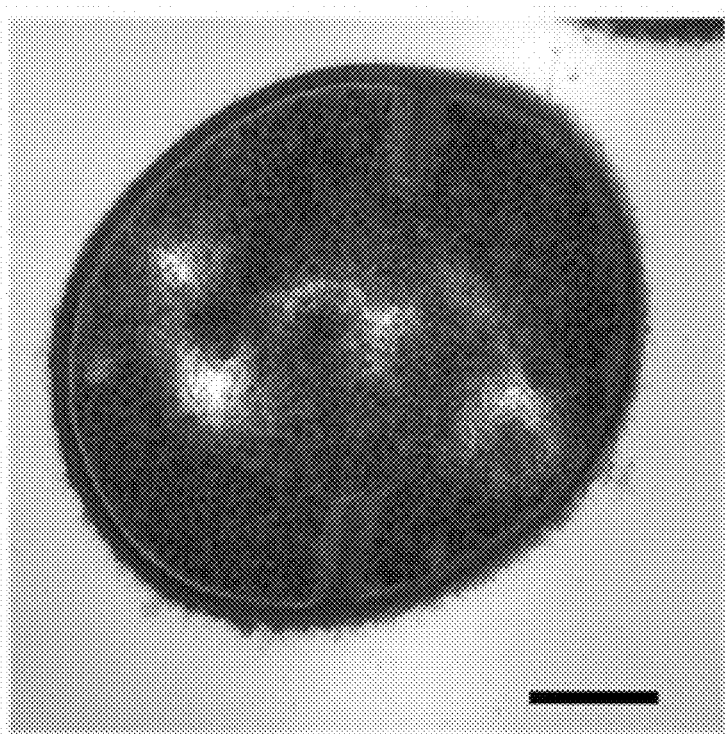
FIG. 12A depicts TEM image of ultra-thin sectioned untreated Gram-positive MRSA.

TEM was used to reveal the damage in bacterial cell envelopes caused by ACA-PA treatment. Drug-resistant bacterial strains (MRSA and MDR *E. coli*) were exposed to ACA-PA at concentrations below (40 µM) and above (80 µM) the CMC, and ultrathin sections of the bacterial cultures were visualized by TEM. FIG. 12A shows proliferating, untreated MRSA with an intact peptidoglycan thick layer as well as a lipid membrane, as characterized by the formation of a cross wall [30]. In the cytoplasmic region enclosed in the cell membrane, ribosomes appear in dark areas with high electron density while the nucleoid displayed lower electron density [31, 32].

Figure 12B:
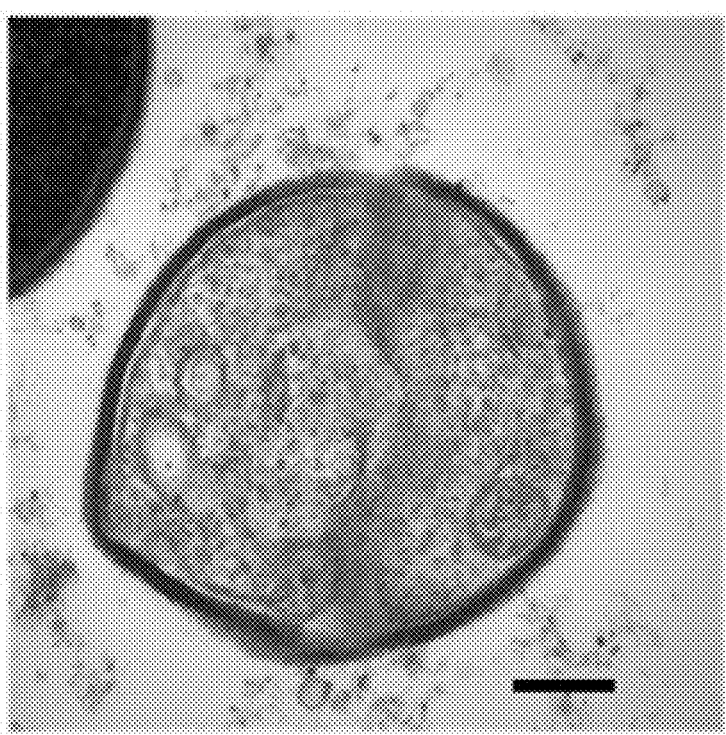
FIG. 12B depicts TEM image of ultra-thin sectioned Gram-positive MRSA treated with 40 μM of an exemplary peptide, ACA-PA.
Figure 12C:
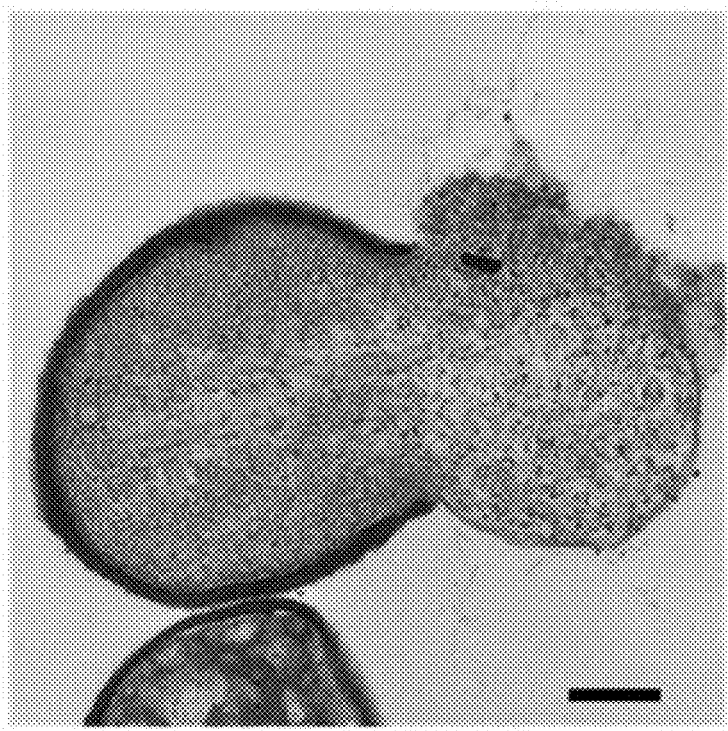
FIG. 12C depicts TEM image of ultra-thin sectioned Gram-positive MRSA treated with 80 μM of an exemplary peptide, ACA-PA.
Figure 12D:
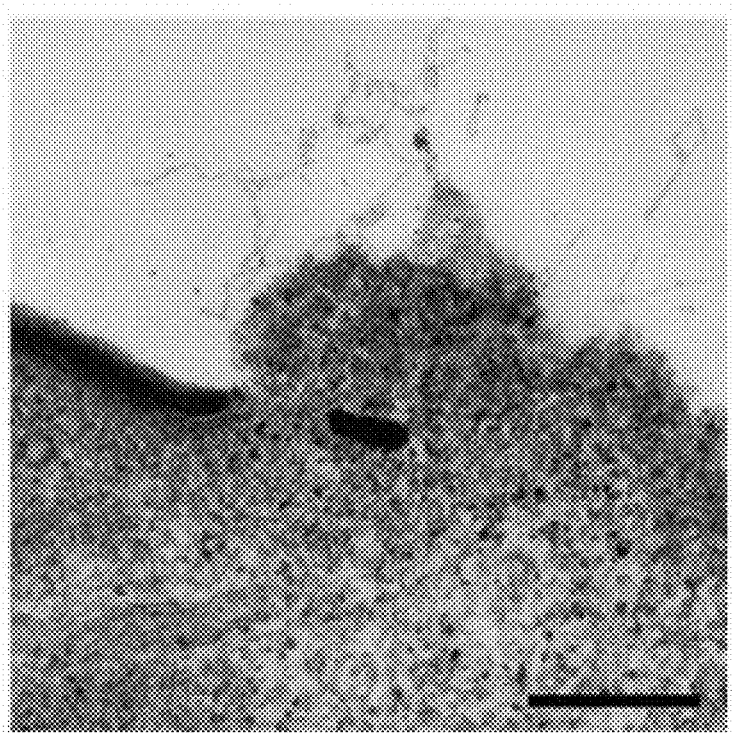
FIG. 12D depicts TEM image of ultra-thin sectioned Gram-positive MRSA treated with 80 μM of an exemplary peptide, ACA-PA.
Figure 12E:
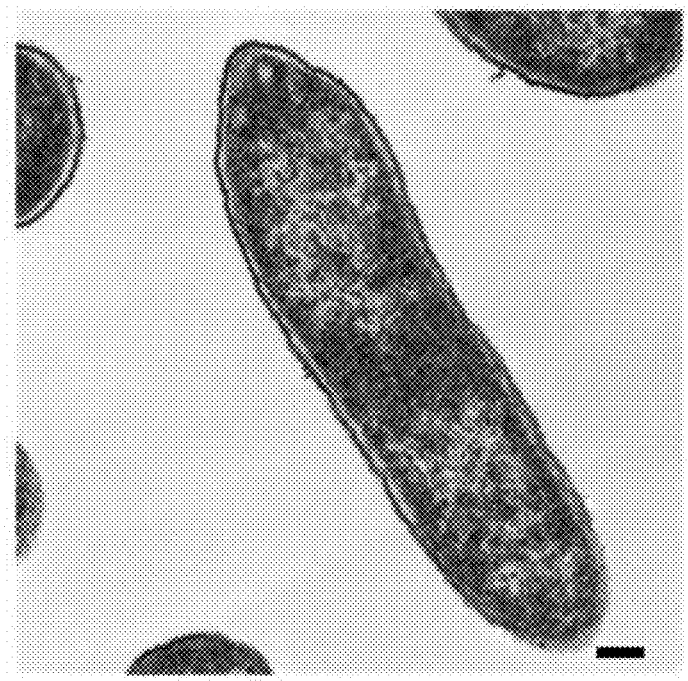
FIG. 12E depicts TEM image of ultra-thin sectioned untreated Gram-negative MDR E. coli.
Figure 12F:
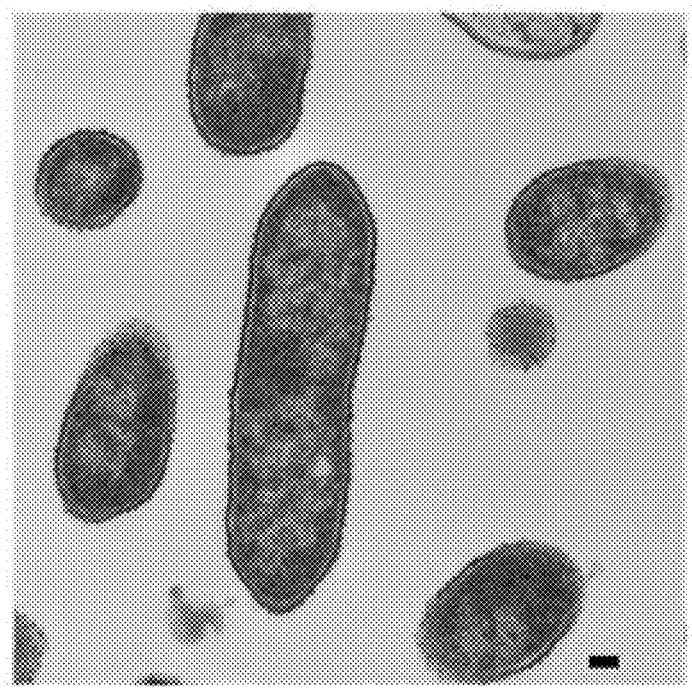
FIG. 12F depicts TEM image of ultra-thin sectioned Gram-negative MDR E. coli treated with 40 μM of an exemplary peptide, ACA-PA.
Figure 12G:
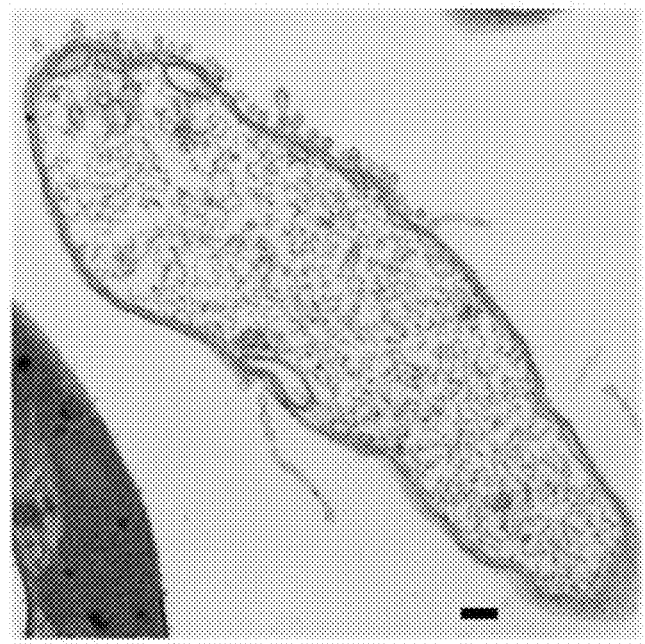
FIG. 12G depicts TEM image of ultra-thin sectioned Gram-negative MDR E. coli treated with 80 μM of an exemplary peptide, ACA-PA.
Figure 12H:
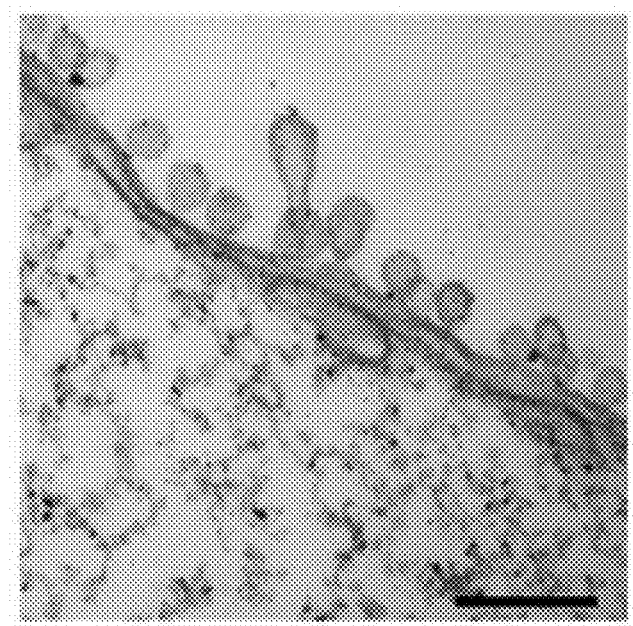
FIG. 12H depicts TEM image of ultra-thin sectioned Gram-negative MDR E. coli treated with 80 μM of an exemplary peptide, ACA-PA.

After treatment with 40 µM of ACA-PA, the thick layer of the peptidoglycan envelope of MRSA was partially damaged and the inner cytoplasmic membrane was no longer attached to the outer membrane, leading to cytoplasmic leakage (FIG. 12B), although the concentration of PA was insufficient for self-assembly. The disintegration of the bacterial cell wall became apparent with increasing concentrations of the ACA-PA (FIGS. 12C and 12D), which demonstrated localized disruption on the cell membrane and complete leakage of the cytoplasm. On the other hand, the control Gram-negative MDR *E. coli* bacteria possess a lipopolysaccharide (LPS) outer membrane that enclosed a thin peptidoglycan membrane followed by a cytoplasmic inner membrane (FIG. 12E). The 40 µM ACA-PA treatment caused blisters only on the outer cell walls of the Gram-negative bacteria (FIG. 12F), but the bacterial inner membranes were intact and the cytoplasm was enclosed. The ACA-PA at a concentration lower than CMC seemed to only influenced the outer bacteria membrane, but were inadequate to disrupt the inner bacteria membranes. However, in FIGS. 12G and 12H, disrupted bacteria envelopes with loosened and disconnected membranous structures were observed after treatment with 80 µM ACA nanorods.

Bacterial membrane disruption was observed from the ultrathin sectioned sample using TEM. The ACA-PA caused localized membrane disintegration on Gram-positive MRSA at both 40 and 80 µM, further indicating that the membrane disruption effects were independent of peptide self-assembly. Nonetheless, ACA-PA at 40 µM (below the CMC) only caused preliminary blisters on the outer membrane of Gram-negative bacteria and were inadequate to induce complete membrane disruption as the cell membranes were still able to enclose the cytoplasm. After treatment with 80 µM ACA nanorods, bacterial cell membranes were severely damaged with complete cytoplasm leakage. Both outer and inner membranes demonstrated disorganized structures throughout the bacterium. On the damaged membranes, blisters appeared to originate from the pores. This explains the reason for the different antibacterial activity of ACA-PA on Gram-negative bacteria compared to the concentration-dependent toxicity on Gram-positive bacteria. The cell envelope of Gram-positive has a cytoplasmic membrane surrounded by a thick peptidoglycan layer with lipoteichoic acid. The antibacterial ACA-PA could penetrate the Gram-positive bacterial membrane by charge and hydrophobicity, although the PA were in a dispersed, non-assembled form. However, such dispersed PA were not able to penetrate the outer membrane of Gram-negative bacteria. Without wishing to be bound by any theory, it is proposed that at concentrations higher than the CMC, ACA-PA induced bacterial cell lysis possibly by the formation of transmembrane pores through the outer and inner membranes, which can be supported by the toroidal model. In the toroidal model, insertion of antibacterial peptides induces a local bending in the membrane leaflets through the pores, resulting in unfavorable elastic tension and ultimately lead to membrane disintegration [9]. Since the formation of self-assembled peptide nanoparticles can increase the local density of the cationic charge [10], once the self-assembly occurred at concentrations over CMC, it is likely that the self-assembled nanorods with localized charge and their β-sheet structure can insert into the cell wall layers perpendicularly and form transmembrane pores, initiating membrane disintegration and cytoplasmic leakage.

To observe the effects of ACA-PA on the bacteria cell membranes, the treated drug-resistant bacteria (MRSA and MDR *E. coli*) were fixed, sectioned and visualized by TEM using methods previously described [25]. Briefly, MRSA and MDR *E. coli* bacteria ($10^7$ CFU/mL) were treated by ACA nanorods at 40 µM and 80 µM in TSB media for 4 h at 37° C. (the control samples were bacteria grown in TSB media at the same condition). The bacteria were centrifuged and then fixed with 2.5% glutaraldehyde in 0.1M sodium cacodylate buffer overnight at 4° C. After rinsing with the sodium cacodylate buffer three times, bacteria pellets were post-fixed with 1% osmium tetroxide for 2 h and dehydrated by gradient ethanol solutions (30%, 50%, 70%, 85%, 90% and 100%). Samples were infiltrated with squetol resin. The resins were polymerized at 55° C. for 24 h and thin-sectioned using an ultra-microtome (Reichert-Jung Ultracut E, Reichert Technologies, Buffalo, NY). The sectioned samples were mounted on 200-hex mesh copper-coated carbon grids and stained by 1.5% uranyl acetate before imaging.

Example 9: Cytotoxicity Assays

Figure 13:
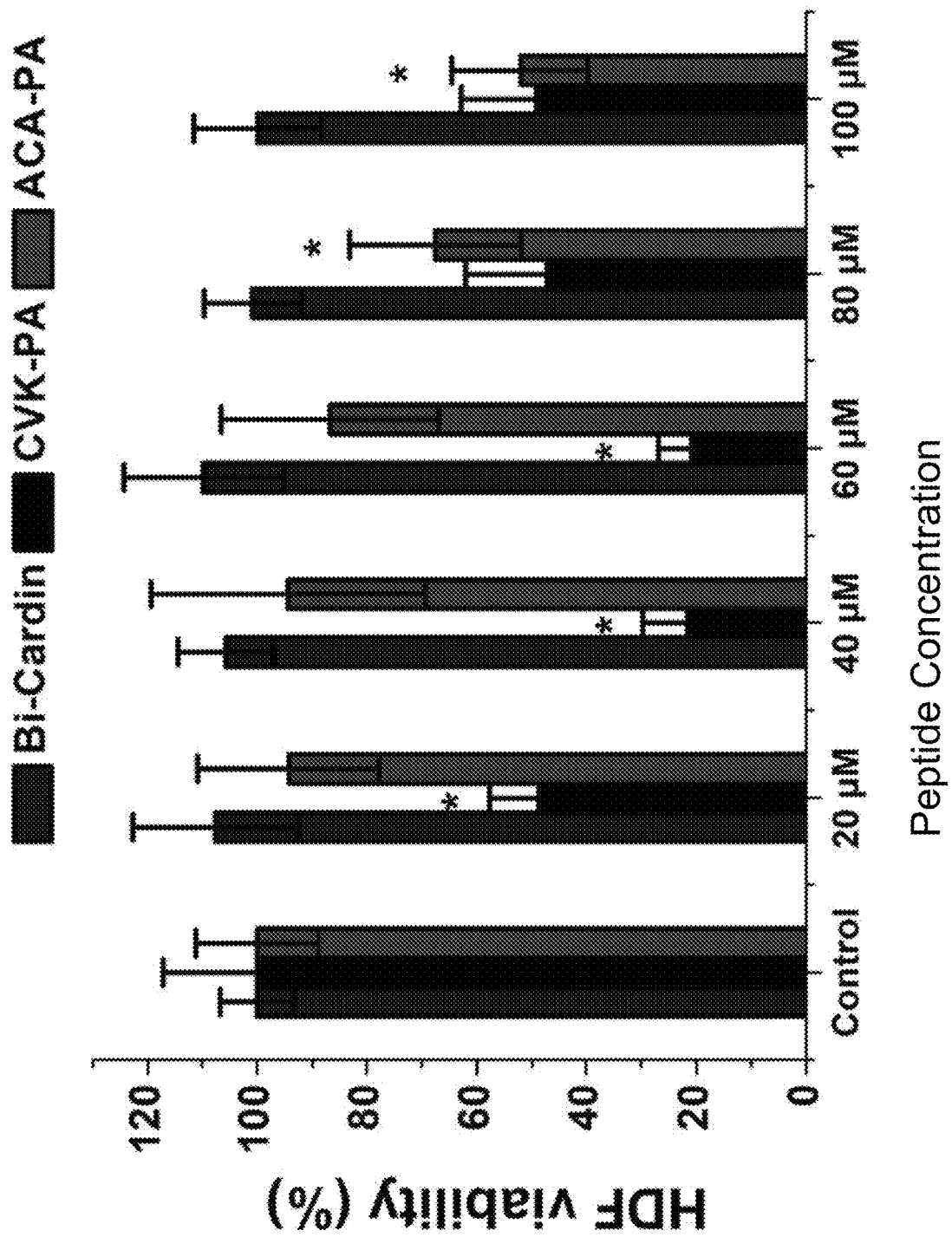
FIG. 13 depicts HDF cell viability after treatment with Bi-Cardin peptide, CVK-PA or ACA-PA.

To evaluate the cytotoxicity of the peptides, human dermal fibroblasts (HDF) were treated for 24 h, and cell viability was determined via MTS assays (FIG. 13). The ACA-PA had significantly lower toxicity towards HDF cells than that observed towards bacteria. At concentrations from 20 µM to 60 µM, the PA showed minimal cytotoxicity, and resulted in over 50% HDF viability at the highest concentration tested at 100 µM.

However, given that CVK-PA as well as ACA-PA showed noticeable toxicity towards HDF cells, biocompatibility of these peptide amphiphiles should be taken into consideration for their potential applications in clinical trials. Similar observation was also demonstrated by Newcomb et al. that nanofiber-forming peptide amphiphiles bearing β-sheet and serial lysine residues can have strong cytotoxicity [37]. The disclosed peptides showed toxicity and inhibitory effects towards drug-resistant bacteria.

Furthermore, although the self-assembled ACA-PA also had a moderate cytotoxicity at high concentrations, it was also significantly more effective against bacteria at concentrations from 60 to 100 µM than HDF cells. At this concentration range, the ACA nanorods induced about a 100-fold decrease in Gram-positive bacteria density, and a 10,000-fold decrease in Gram-negative bacteria density, but caused comparatively lower percentages of reduction (48%) in HDF cell viability. The Bi-Cardin peptide was shown to be non-cytotoxic at all the concentrations tested. The CVK-PA critically decreased the cell viability at concentrations higher than 20 µM, which induced over 40% of cell death.

Human dermal fibroblast cells (HDF, Detroit 551, ATCC #CCL-110) were cultured in Dulbecco's modified Eagle medium (DMEM; Fisher, Pittsburgh, PA) supplemented with 10% fetal bovine serum (FBS) and 1% penicillin/streptomycin for 24 h. All cells were cultured to 90% confluence in a 37° C., humidified, 5% $CO_2$/95% air environment. Cells at passage numbers of 4-7 were used in these experiments.

The MTS cell viability assay kit (Promega, Madison, WI, USA) was used to determine cytotoxicity of the peptides. First, HDF cells were seeded on a 96-well plate at a cell density of 5,000 cells/well (equal to 15,385 cells/cm$^2$), and were incubated overnight for cell adhesion. After overnight incubation, the cell medium in each well was replaced by 100 µL of cell culture medium containing various concentrations of peptides (20 µM to 100 µM). The control samples were cells incubated in cell culture medium only. After 24 h, the treatment medium in each well was removed. The cells were washed with phosphate buffered saline (PBS, pH=7.4, Fisher, PA, USA) and 100 µL of fresh cell culture medium was added to each well, followed by the addition of 20 µL of the MTS reagent. After the cells were incubated for 2.5 h, the absorbance was measured at a wavelength of 490 nm by a spectrophotometer (SpectraMax M3, Molecular Devices, Molecular Devices, Sunnyvale, CA, USA). To estimate the cell numbers in each well, a standard curve expressing the linear correlation between different cell densities and optical densities ($R^2$>0.95) was plotted, and the cell numbers were determined with this standard curve from the $OD_{490}$ value recorded in each sample. The cell viability of each sample was calculated by: Cell viability=[(cell density per mL of treated sample)/(cell density per mL of control sample)]× 100%. Data were expressed by standard error of the mean (±S.E.M.) and N=3, *p<0.05 compared with control samples.

A self-assembled ACA-PA functionalized with a heparin-binding (AKKARA)$_2$ (SEQ ID NO: 2) Cardin-motif sequence was designed to form nanoparticles with cylindrical shapes. At concentrations above the CMC (45 µM), the ACA-PA were found to self-assemble into nanorods about 7 to 10 nm in diameter. The ACA-PA was shown to have excellent antibacterial properties against both Gram-negative and Gram-positive bacteria in contrast to the CVK-PA and Bi-Cardin peptide. Antibacterial results demonstrated for the first time that ACA-PA had a concentration-dependent toxicity against Gram-positive bacteria (*S. aureus* and MRSA). For Gram-negative bacteria (*E. coli* and MDR *E. coli*), the ACA-PA possessed bactericidal effects only in self-assembled form, which indicated that self-assembly played a crucial role in antibacterial activity against Gram-negative bacteria. In all cases, the CVK-PA and Bi-Cardin peptide showed minimal antibacterial effect. With its strong interactions with LPS layer and formation of secondary structure on the prokaryotic membrane, the ACA-PA could target bacteria membranes and result in localized membrane disintegration against Gram-positive bacteria and blisters on the surface of Gram-negative bacteria, causing bacterial cytoplasmic leakage. Functionalization with a self-assembled PA effectively enhanced the antibacterial activity of the cationic Cardin-motif peptide sequence, and the resulting self-assembled nanorods are promising agents to combat infectious diseases caused by bacteria drug-resistance.

REFERENCES CITED

1. Centers of Disease Control and Prevention, (<http://www.cdc.gov/drugresistance/about.html> [Accessed Sep. 8, 2015].
2. Schmieder, R.; Edwards, R. Insights into Antibiotic Resistance through Metagenomic Approaches, *Future Microbiol.* 2011, 7, 73-89.
3. Zasloff, M. Antimicrobial Peptides of Multicellular Organisms, *Nature.* 2002, 415, 389-95.
4. Domingues, T. M.; Perez, K. R.; Miranda, A.; Riske, K. A. Comparative Study of the Mechanism of Action of the Antimicrobial Peptide Gomesin and Its Linear Analogue: The Role of the β-Hairpin Structure, *BBA-Rev Biomembranes.* 2015, 1848, 2414-21.
5. Juba, M. L.; Porter, D. K.; Williams, E. H.; Rodriguez, C. A.; Barksdale, S. M.; Bishop, B. M. Helical Cationic Antimicrobial Peptide Length and Its Impact on Membrane Disruption, *BBA-Rev Biomembranes.* 2015, 1848, 1081-91.
6. Teixeira, V.; Feio, M. J.; Bastos, M. Role of Lipids in the Interaction of Antimicrobial Peptides with Membranes, *Prog. Lipid Res.* 2012, 51, 149-77.
7. Yeaman, M. R.; Yount, N. Y. Mechanisms of Antimicrobial Peptide Action and Resistance, *Pharmacol Rev,* 2003, 55, 27-55.
8. Yin, L. M.; Edwards, M. A.; Li, J.; Yip; C. M.; Deber, C. M. Roles of Hydrophobicity and Charge Distribution of Cationic Antimicrobial Peptides in Peptide-Membrane Interactions, *J. Biol. Chem.* 2012, 287, 7738-45.
9. Ong, Z. Y.; Wiradharma, N.; Yang, Y. Y. Strategies Employed in the Design and Optimization of Synthetic Antimicrobial Peptide Amphiphiles with Enhanced Therapeutic Potentials, *Adv Drug Deliv Rev.* 2014, 78, 28-45.
10. Zhang, Y.; Algburi, A.; Wang, N.; Kholodovych, V.; Oh, D. O.; Chikindas, M.; Uhrich, K. E. Self-Assembled Cationic Amphiphiles as Antimicrobial Peptides Mimics: Role of Hydrophobicity, Linkage Type, and Assembly State, *Nanomed Nanotech BIOL MED.* 2016.
11. Yount, N. Y.; Bayer, A. S.; Xiong, Y. Q.; Yeaman, M. R. Advances in Antimicrobial Peptide Immunobiology, *J. Pept. Sci.* 2006, 84, 435-58.
12. Chu-Kung, A. F.; Nguyen, R.; Bozzelli, K. N.; Tirrell, M. Chain Length Dependence of Antimicrobial Peptide-Fatty Acid Conjugate Activity, *J. Colloid Interface Sci.* 2010, 345, 160-67.
13. Malmsten, M.; Kasetty, G.; PAupuleti, M.; Alenfall, J.; and Schmidtchen, A. Highly Selective End-Tagged Antimicrobial Peptides Derived from PRELP, *PLoS One.* 2011, 6, 1-13.
14. Ong, Z. Y.; Gao, S. J.; Yang, Y. Y. Short Synthetic β-Sheet Forming Peptide Amphiphiles as Broad Spectrum Antimicrobials with Antibiofilm and Endotoxin Neutralizing Capabilities, *Adv. Funct. Mater.* 2013, 23, 3682-92.
15. Chen, C.; Pan, F.; Zhang, S.; Hu, J.; Cao, M.; Wang, J.; Xu, H.; Zhao, X.; Lu, J. R. Antibacterial Activities of Short Designer Peptides: A Link between Propensity for Nanostructuring and Capacity for Membrane Destabilization, *Biomacromolecules.* 2010, 11, 402-11.
16. Brogden, K. A. Antimicrobial Peptides: Pore Formers or Metabolic Inhibitors in Bacteria?, *Nat Rev Micro.* 2005, 3, 238-50.
17. Webber, M. J.; Berns, E. J.; Stupp, S. I. Supramolecular Nanofibers of Peptide Amphiphiles for Medicine, *Isr. J. Chem.* 2013, 53, 530-54.
18. Stephanopoulos, N.; Ortony, J. H.; Stupp, S. I. Self-Assembly for the Synthesis of Functional Biomaterials, *Acta Mater.* 2013, 61, 912-30.
19. Chen, Y.; Gan, H. X.; Tong, Y. W. pH-Controlled Hierarchical Self-Assembly of Peptide Amphiphile, *Macromolecules.* 2015, 48, 2647-53.
20. Luo, J.; Tong, Y. W. Self-Assembly of Collagen-Mimetic Peptide Amphiphiles into Biofunctional Nanofiber, *ACS Nano.* 2011, 5, 7739-47.
21. Cardin, A. D.; Weintraub, H. J. Molecular Modeling of Protein-Glycosaminoglycan Interactions, *Arterioscler Thromb Vasc Biol.* 1989, 9, 21-32.
22. Andersson, E.; Rydengård, V.; Sonesson, A.; Mörgelin, M.; Björck, L.; Schmidtchen, A. Antimicrobial Activities of Heparin-Binding Peptides, *Eur J Biochem.* 2004, 271, 1219-26.
23. Ringstad, L.; Schmidtchen, A.; Malmsten, M. Effect of Peptide Length on the Interaction between Consensus Peptides and DOPC/DOPA Bilayers, *Langmuir.* 2006, 22, 5042-50.
24. Geilich, B. M.; van de Ven, A. L.; Singleton, G. L.; Sepulveda, L. J.; Sridhar, S.; Webster, T. J. Silver Nanoparticle-Embedded Polymersome Nanocarriers for the Treatment of Antibiotic-Resistant Infections, *Nanoscale.* 2015, 7, 3511-9.
25. Pulido, D.; Prats-Ejarque, G.; Villalba, C.; Albacar, M.; Gonzalez-Lopez, J. J.; Torrent, M.; Moussaoui, M.; Boix, E. A Novel Rnase 3/Ecp Peptide for *Pseudomonas Aeruginosa* Biofilm Eradication That Combines Antimicrobial, Lipopolysaccharide Binding, and Cell-Agglutinating Activities, *Antimicrob. Agents Chemother.* 2016, 60, 6313-25.
26. Torrent, M.; Navarro, S.; Moussaoui, M.; Nogués, M. V.; Boix, E. Eosinophil Cationic Protein High-Affinity Binding to Bacteria-Wall Lipopolysaccharides and Peptidoglycans, *Biochemistry.* 2008, 47, 3544-55.
27. Welsh, D. J.; Posocco, P.; Pricl, S.; Smith, D. K. Self-Assembled Multivalent RGD-Peptide Arrays—Morphological Control and Integrin Binding, *Org. Biomol. Chem.* 2013, 11, 3177-86.
28. Shao, H.; Parquette, J. R. Controllable Peptide-Dendron Self-Assembly: Interconversion of Nanotubes and Fibrillar Nanostructures, *Angew. Chem. Int. Ed.* 2009, 48, 2525-28.
29. Ramanathan, M; Shrestha, K. L.; Mori, T.; Ji, Q.; Hill, J. P.; Ariga, K. Amphiphile Nanoarchitectonics: From Basic Physical Chemistry to Advanced Applications, *Phys. Chem. Chem. Phys.* 2013, 15, 10580-10611.
30. Yun-mi, K., Samuel, R. F., and Ronald, H. B. Membrane Damage of Bacteria by Silanols Treatment, *Electron. J. Biotechnol.* 2007, 2, 252-259.
31. Stahlberg, H.; Kutejová, E.; Muchová, K.; Gregorini, M.; Lustig, A.; Müller, S. A.; Olivieri, V.; Engel, A.; Wilkinson, A. J.; Barák, I. Oligomeric Structure of the Bacillus Subtilis Cell Division Protein Diviva Determined by Transmission Electron Microscopy, *Mol MicrobioL* 2004, 52, 1281-90.

32. Kim, T.; Han, J. I. Fast Detection and Quantification of *Escherichia Coli* Using the Base Principle of the Microbial Fuel Cell, *J Environ Manage.* 2013, 130, 267-75.

33. Hancock, R. E. W.; Chapple, D. S. (1999), Peptide Antibiotics, *Antimicrob Agents Chemother.* 1999, 43, 1317-23.

34. Manzo, G.; Scorciapino, M. A.; Wadhwani, P.; Burck, J.; Montaldo, N. P.; Pintus, M.; Sanna, R.; Casu, M.; Giuliani, A.; Pirri, G.; Luca, V.; Ulrich, A. S.; Rinaldi, A. C. Enhanced Amphiphilic Profile of a Short Beta-Stranded Peptide Improves Its Antimicrobial Activity, *PloS one.* 2015, 10, e0116379.

35. Delcour. A. H. Outer Membrane Permeability and Antibiotic Resistance, *Biochim Biophys Acta.* 2009, 61A, 1794, 808-816.

36. Hancock, R. E. W. Peptide Antibiotics, *The Lancet.* 1997, 349, 418-22.

37. Newcomb, C. J.; Sur, S.; Ortony, J. H.; Lee, O. S.; Matson, J. B.; Boekhoven, J.; Yu, J. M.; Schatz, G. C.; Stupp, S. I. Cell Death Versus Cell Survival Instructed by Supramolecular Cohesion of Nanostructures, *Nat. Commun.* 2014, 5, 3321.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

---

We claim:

1. A method of preventing or suppressing growth of a bacterium on a surface, comprising:
applying to the surface a plurality of polypeptides represented by:

$R^1\text{-}y^1\text{-}y^2$ wherein
$R^1\text{-}y^1$ is an amphiphilic backbone;
$y^2$ is a cationic heparin-binding Cardin motif peptide;
$R^1$ is an alkyl group or an alkenyl group; and
$y^1$ has the sequence $V_4K_4$ (SEQ ID NO: 1) or $V_4K_4G$ (SEQ ID NO: 4)
thereby preventing or suppressing growth of the bacterium on the surface.

2. The method of claim 1, wherein $R^1$ is selected from the group consisting of $C_{12}$, $C_{14}$, $C_{16}$, C16:1, $C_{18}$, C18:1, C18:2, C18:3, $C_{20}$, C20:1, C20:4, C20:5, $C_{22}$, C22:1, and C22:6.

3. The method of claim 1, wherein $y^2$ has the following sequence (SEQ ID NO: 5):

$\text{-(WZZWZW)}_m$ wherein
W is A or G;
Z is K or R; and
m is 2, 3, 4, 5, 6, 7, 8, 9, or 10.

4. The method of claim 3, wherein W is A.

5. The method of claim 3, wherein Z is K.

6. The method of claim 3, wherein m is 2.

7. The method of claim 3, wherein $y^2$ has the sequence $\text{-(AKKARA)}_m$ (SEQ ID NO: 6).

8. The method of claim 1, wherein the bacterium on the surface is a Gram-negative bacterium.

9. The method of claim 8, wherein the Gram-negative bacterium on the surface is Gram-negative *Escherichia coli*.

10. The method of claim 8, wherein the Gram-negative bacterium on the surface is Gram-negative multidrug-resistant *Escherichia coli*.

11. The method of claim 1, wherein the bacterium on the surface is a Gram-positive bacterium.

12. The method of claim 11, wherein the Gram-positive bacterium on the surface is a Gram-positive *Staphylococcus aureus*.

13. The method of claim 11, wherein the Gram-positive bacterium on the surface is a Gram-positive Methicillin-resistant *Staphylococcus aureus* (MRSA).

* * * * *

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Val Val Val Lys Lys Lys Lys
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Lys Lys Ala Arg Ala Ala Lys Lys Ala Arg Ala
1               5                   10

<210> SEQ ID NO 3
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Ile, Leu, or Val
<220> FEATURE:
<221> NAME/KEY: MISC_FEATURE
<222> LOCATION: (1)..(10)
<223> OTHER INFORMATION: This region may encompass 2-10 residues
<220> FEATURE:
<221> NAME/KEY: MOD_RES
<222> LOCATION: (11)..(20)
<223> OTHER INFORMATION: Lys or Arg
<220> FEATURE:
<221> NAME/KEY: MISC_FEATURE
<222> LOCATION: (11)..(20)
<223> OTHER INFORMATION: This region may encompass 2-10 residues
<220> FEATURE:
<221> NAME/KEY: MOD_RES
<222> LOCATION: (21)..(21)
<223> OTHER INFORMATION: Ala, Gly, or absent
<220> FEATURE:
<223> OTHER INFORMATION: See specification as filed for detailed
      description of substitutions and preferred embodiments

<400> SEQUENCE: 3

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Val Val Val Lys Lys Lys Lys Gly
1               5

<210> SEQ ID NO 5
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ala or Gly
<220> FEATURE:
<221> NAME/KEY: MOD_RES
<222> LOCATION: (2)..(3)
<223> OTHER INFORMATION: Lys or Arg
<220> FEATURE:
<221> NAME/KEY: MOD_RES
<222> LOCATION: (4)..(4)
<223> OTHER INFORMATION: Ala or Gly
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(7)
```

```
<223> OTHER INFORMATION: Ala or Gly
<220> FEATURE:
<221> NAME/KEY: MOD_RES
<222> LOCATION: (8)..(9)
<223> OTHER INFORMATION: Lys or Arg
<220> FEATURE:
<221> NAME/KEY: MOD_RES
<222> LOCATION: (10)..(10)
<223> OTHER INFORMATION: Ala or Gly
<220> FEATURE:
<221> NAME/KEY: MOD_RES
<222> LOCATION: (11)..(11)
<223> OTHER INFORMATION: Lys or Arg
<220> FEATURE:
<221> NAME/KEY: MOD_RES
<222> LOCATION: (12)..(13)
<223> OTHER INFORMATION: Ala or Gly
<220> FEATURE:
<221> NAME/KEY: MOD_RES
<222> LOCATION: (14)..(15)
<223> OTHER INFORMATION: Lys or Arg
<220> FEATURE:
<221> NAME/KEY: MOD_RES
<222> LOCATION: (16)..(16)
<223> OTHER INFORMATION: Ala or Gly
<220> FEATURE:
<221> NAME/KEY: MOD_RES
<222> LOCATION: (17)..(17)
<223> OTHER INFORMATION: Lys or Arg
<220> FEATURE:
<221> NAME/KEY: MOD_RES
<222> LOCATION: (18)..(19)
<223> OTHER INFORMATION: Ala or Gly
<220> FEATURE:
<221> NAME/KEY: MOD_RES
<222> LOCATION: (20)..(21)
<223> OTHER INFORMATION: Lys or Arg
<220> FEATURE:
<221> NAME/KEY: MOD_RES
<222> LOCATION: (22)..(22)
<223> OTHER INFORMATION: Ala or Gly
<220> FEATURE:
<221> NAME/KEY: MOD_RES
<222> LOCATION: (23)..(23)
<223> OTHER INFORMATION: Lys or Arg
<220> FEATURE:
<221> NAME/KEY: MOD_RES
<222> LOCATION: (24)..(25)
<223> OTHER INFORMATION: Ala or Gly
<220> FEATURE:
<221> NAME/KEY: MOD_RES
<222> LOCATION: (26)..(27)
<223> OTHER INFORMATION: Lys or Arg
<220> FEATURE:
<221> NAME/KEY: MOD_RES
<222> LOCATION: (28)..(28)
<223> OTHER INFORMATION: Ala or Gly
<220> FEATURE:
<221> NAME/KEY: MOD_RES
<222> LOCATION: (29)..(29)
<223> OTHER INFORMATION: Lys or Arg
<220> FEATURE:
<221> NAME/KEY: MOD_RES
<222> LOCATION: (30)..(31)
<223> OTHER INFORMATION: Ala or Gly
<220> FEATURE:
<221> NAME/KEY: MOD_RES
<222> LOCATION: (32)..(33)
<223> OTHER INFORMATION: Lys or Arg
<220> FEATURE:
<221> NAME/KEY: MOD_RES
<222> LOCATION: (34)..(34)
<223> OTHER INFORMATION: Ala or Gly
<220> FEATURE:
<221> NAME/KEY: MOD_RES
<222> LOCATION: (35)..(35)
<223> OTHER INFORMATION: Lys or Arg
<220> FEATURE:
<221> NAME/KEY: MOD_RES
```

```
<222> LOCATION: (36)..(37)
<223> OTHER INFORMATION: Ala or Gly
<220> FEATURE:
<221> NAME/KEY: MOD_RES
<222> LOCATION: (38)..(39)
<223> OTHER INFORMATION: Lys or Arg
<220> FEATURE:
<221> NAME/KEY: MOD_RES
<222> LOCATION: (40)..(40)
<223> OTHER INFORMATION: Ala or Gly
<220> FEATURE:
<221> NAME/KEY: MOD_RES
<222> LOCATION: (41)..(41)
<223> OTHER INFORMATION: Lys or Arg
<220> FEATURE:
<221> NAME/KEY: MOD_RES
<222> LOCATION: (42)..(43)
<223> OTHER INFORMATION: Ala or Gly
<220> FEATURE:
<221> NAME/KEY: MOD_RES
<222> LOCATION: (44)..(45)
<223> OTHER INFORMATION: Lys or Arg
<220> FEATURE:
<221> NAME/KEY: MOD_RES
<222> LOCATION: (46)..(46)
<223> OTHER INFORMATION: Ala or Gly
<220> FEATURE:
<221> NAME/KEY: MOD_RES
<222> LOCATION: (47)..(47)
<223> OTHER INFORMATION: Lys or Arg
<220> FEATURE:
<221> NAME/KEY: MOD_RES
<222> LOCATION: (48)..(49)
<223> OTHER INFORMATION: Ala or Gly
<220> FEATURE:
<221> NAME/KEY: MOD_RES
<222> LOCATION: (50)..(51)
<223> OTHER INFORMATION: Lys or Arg
<220> FEATURE:
<221> NAME/KEY: MOD_RES
<222> LOCATION: (52)..(52)
<223> OTHER INFORMATION: Ala or Gly
<220> FEATURE:
<221> NAME/KEY: MOD_RES
<222> LOCATION: (53)..(53)
<223> OTHER INFORMATION: Lys or Arg
<220> FEATURE:
<221> NAME/KEY: MOD_RES
<222> LOCATION: (54)..(55)
<223> OTHER INFORMATION: Ala or Gly
<220> FEATURE:
<221> NAME/KEY: MOD_RES
<222> LOCATION: (56)..(57)
<223> OTHER INFORMATION: Lys or Arg
<220> FEATURE:
<221> NAME/KEY: MOD_RES
<222> LOCATION: (58)..(58)
<223> OTHER INFORMATION: Ala or Gly
<220> FEATURE:
<221> NAME/KEY: MOD_RES
<222> LOCATION: (59)..(59)
<223> OTHER INFORMATION: Lys or Arg
<220> FEATURE:
<221> NAME/KEY: MOD_RES
<222> LOCATION: (60)..(60)
<223> OTHER INFORMATION: Ala or Gly
<220> FEATURE:
<221> NAME/KEY: MISC_FEATURE
<222> LOCATION: (1)..(60)
<223> OTHER INFORMATION: This sequence may encompass 2-10 "WZZWZW"
      repeating units, wherein W is Ala or Gly and Z is Lys or Arg
<220> FEATURE:
<223> OTHER INFORMATION: See specification as filed for detailed
      description of substitutions and preferred embodiments

<400> SEQUENCE: 5

Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
    50                  55                  60

<210> SEQ ID NO 6
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(60)
<223> OTHER INFORMATION: This sequence may encompass 2-10 "AKKARA"
      repeating units

<400> SEQUENCE: 6

Ala Lys Lys Ala Arg Ala Ala Lys Lys Ala Arg Ala Ala Lys Lys Ala
1               5                   10                  15

Arg Ala Ala Lys Lys Ala Arg Ala Ala Lys Lys Ala Arg Ala Ala Lys
            20                  25                  30

Lys Ala Arg Ala Ala Lys Lys Ala Arg Ala Ala Lys Lys Ala Arg Ala
        35                  40                  45

Ala Lys Lys Ala Arg Ala Ala Lys Lys Ala Arg Ala
    50                  55                  60

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Val Val Val Lys Lys Lys Lys Gly Ala Lys Lys Ala Arg Ala Ala
1               5                   10                  15

Lys Lys Ala Arg Ala
            20

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Val Val Lys Lys Lys
1               5
```